United States Patent
Tamai et al.

(10) Patent No.: US 12,304,933 B2
(45) Date of Patent: May 20, 2025

(54) DISEASE TREATMENT DRUG BASED ON MESENCHYMAL-STEM-CELL MOBILIZATION

(71) Applicants: StemRIM Inc., Osaka (JP); OSAKA UNIVERSITY, Osaka (JP)

(72) Inventors: Katsuto Tamai, Osaka (JP); Takashi Shimbo, Osaka (JP); Takehiko Yamazaki, Osaka (JP)

(73) Assignees: STEMRIM INC., Osaka (JP); OSAKA UNIVERSITY, Osaka (JP)

( * ) Notice: Subject to any disclaimer, the term of this patent is extended or adjusted under 35 U.S.C. 154(b) by 249 days.

(21) Appl. No.: 17/282,872

(22) PCT Filed: Apr. 10, 2019

(86) PCT No.: PCT/JP2019/039231
§ 371 (c)(1),
(2) Date: Apr. 5, 2021

(87) PCT Pub. No.: WO2020/071519
PCT Pub. Date: Apr. 9, 2020

(65) Prior Publication Data
US 2021/0347839 A1 Nov. 11, 2021

(30) Foreign Application Priority Data
Oct. 5, 2018 (JP) .................. 2018-190089

(51) Int. Cl.
| C07K 14/47 | (2006.01) |
| A61K 38/00 | (2006.01) |
| A61P 1/00 | (2006.01) |
| A61P 17/06 | (2006.01) |
| A61P 37/06 | (2006.01) |

(52) U.S. Cl.
CPC ............ *C07K 14/4713* (2013.01); *A61P 1/00* (2018.01); *A61P 17/06* (2018.01); *A61P 37/06* (2018.01); *A61K 38/00* (2013.01); *C07K 2319/09* (2013.01)

(58) Field of Classification Search
CPC ............ C07K 14/4713; C07K 2319/09; A61P 17/06; A61P 37/06; A61P 1/00; A61K 38/00
See application file for complete search history.

(56) References Cited

U.S. PATENT DOCUMENTS

| 3,896,810 | A | 7/1975 | Akiyama |
| 4,732,155 | A | 3/1988 | Zetter et al. |
| 5,133,755 | A | 7/1992 | Brekke |
| 5,661,127 | A | 8/1997 | Bhatnagar et al. |
| 5,760,261 | A | 6/1998 | Guttag |
| 5,851,986 | A | 12/1998 | Takada et al. |
| 5,902,799 | A | 5/1999 | Herrmann et al. |
| 6,723,319 | B1 | 4/2004 | Ito et al. |
| 6,905,874 | B2 | 6/2005 | Berenson et al. |
| 7,220,723 | B2 | 5/2007 | Tracey et al. |
| 7,288,250 | B2 | 10/2007 | Newman et al. |
| 7,446,100 | B2 | 11/2008 | Pilarski |
| 7,470,538 | B2 | 12/2008 | Laughlin et al. |
| 7,585,504 | B2 | 9/2009 | Wu et al. |
| 7,632,802 | B2 | 12/2009 | Tessier et al. |
| 7,749,959 | B2 | 7/2010 | Tracey et al. |
| 7,829,097 | B2 | 11/2010 | Tsung et al. |
| 7,833,975 | B2 | 11/2010 | Okazawa |
| 7,939,057 | B2 | 5/2011 | Battista et al. |
| 8,114,668 | B2 | 2/2012 | Stolen et al. |
| 8,119,121 | B2 | 2/2012 | Fraser et al. |
| 8,551,470 | B2 | 10/2013 | Son et al. |
| 8,673,580 | B2 | 3/2014 | Tamai et al. |
| 9,623,078 | B2 | 4/2017 | Tamai et al. |
| 9,688,733 | B2 | 6/2017 | Tamai et al. |

(Continued)

FOREIGN PATENT DOCUMENTS

| AU | 2003228099 A1 | 1/2004 |
| AU | 2004203732 A1 | 7/2004 |

(Continued)

OTHER PUBLICATIONS

Shi et al, Nucleocapsid Interacts with NPM1 and Protects it from Proteolytic Cleavage, Enhancing Cell Survival, and is Involved in PEDV Growth, Scientific Reports, 2017, pp. 1-16.*
Ko et al, SERPINA3 is a key modulator of HNRNP-K transcriptional activity against oxidative stress in HCC, Redox Biology, 2019, 24, pp. 1-10.*
Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
De Meyer et al, Extracellular Chromatin Is an Important Mediator of Ischemic Stroke in Mice, Arterioscler Thromb Vasc Biol, 2012, 32, pp. 1884-1891.*

(Continued)

*Primary Examiner* — Li N Komatsu
(74) *Attorney, Agent, or Firm* — SALIWANCHIK, LLOYD & EISENSCHENK

(57) ABSTRACT

The present inventors identified many nuclear proteins contained in the extract of skin tissue by mass spectrometry, randomly selected multiple partial amino acid sequences of the nuclear proteins, chemically synthesized peptides consisting of the partial amino acid sequences, and examined their activity of mobilizing mesenchymal stem cells. As a result, it was found that these multiple peptides show the activity of mobilizing mesenchymal stem cells into peripheral blood, even though their amino acid sequences are completely different from each other. The inventors also found that fragment peptides of the nuclear proteins have therapeutic effects on diseases characterized by inflammation and abnormalities of the immune system (e.g., inflammatory bowel disease and psoriasis). Based on these findings, a new regenerative medicine technology that can overcome the problems of cell transplantation therapy is provided.

5 Claims, 5 Drawing Sheets

Specification includes a Sequence Listing.

(56) References Cited

U.S. PATENT DOCUMENTS

| | | |
|---|---|---|
| 9,919,010 B2 | 3/2018 | Tamai et al. |
| 10,364,276 B2 | 7/2019 | Tamai et al. |
| 10,393,762 B2 | 8/2019 | Fuhrmann et al. |
| 10,595,530 B2 | 3/2020 | Goodman et al. |
| 10,626,153 B2 | 4/2020 | Bianchi et al. |
| 2003/0003482 A1 | 1/2003 | Halle et al. |
| 2003/0060410 A1 | 3/2003 | Tracey et al. |
| 2004/0028681 A1 | 2/2004 | Ito et al. |
| 2004/0031072 A1 | 2/2004 | La Rosa et al. |
| 2004/0156851 A1 | 8/2004 | Newman |
| 2004/0191246 A1 | 9/2004 | Connelly et al. |
| 2004/0242481 A1 | 12/2004 | Bianchi et al. |
| 2004/0249448 A1 | 12/2004 | Gault |
| 2004/0265971 A1 | 12/2004 | Sato et al. |
| 2005/0014255 A1 | 1/2005 | Tang et al. |
| 2005/0101564 A1 | 5/2005 | Pilarski |
| 2006/0003312 A1 | 1/2006 | Blau et al. |
| 2006/0035851 A1 | 2/2006 | Bianchi et al. |
| 2006/0039896 A1 | 2/2006 | Kleinsek et al. |
| 2006/0069064 A1 | 3/2006 | Khaldoyanidi |
| 2006/0111287 A1 | 5/2006 | Bianchi |
| 2006/0183667 A1 | 8/2006 | Jonassen et al. |
| 2007/0154529 A1 | 7/2007 | Bullerdiek |
| 2007/0238663 A1 | 10/2007 | Capogrossi et al. |
| 2008/0038309 A1 | 2/2008 | Fumero et al. |
| 2008/0064065 A1 | 3/2008 | Kim et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2010/0040608 A1 | 2/2010 | Wahren-Herlenius et al. |
| 2010/0280493 A1 | 11/2010 | Nayak |
| 2011/0097309 A1 | 4/2011 | Tamai et al. |
| 2012/0237504 A1 | 9/2012 | Brooks et al. |
| 2012/0251510 A1 | 10/2012 | Tamai et al. |
| 2014/0206619 A1 | 7/2014 | Tamai et al. |
| 2016/0032248 A1 | 2/2016 | Short et al. |
| 2018/0055886 A1 | 3/2018 | Tamai et al. |
| 2018/0072785 A1 | 3/2018 | Tamai et al. |
| 2019/0343924 A1 | 11/2019 | Tamai et al. |
| 2020/0038486 A1 | 2/2020 | Tamai et al. |
| 2020/0291359 A1 | 9/2020 | Tamai et al. |
| 2020/0369736 A1 | 11/2020 | Tamai et al. |
| 2021/0024594 A1 | 1/2021 | Tamai et al. |
| 2021/0163552 A1 | 6/2021 | Nihashi et al. |
| 2022/0009976 A1 | 1/2022 | Tamai et al. |
| 2022/0380420 A1 | 12/2022 | Tamai et al. |
| 2023/0212241 A1 | 7/2023 | Tamai et al. |
| 2023/0241159 A1 | 8/2023 | Tamai et al. |

FOREIGN PATENT DOCUMENTS

| | | |
|---|---|---|
| AU | 2007315073 A1 | 5/2008 |
| AU | 2012248676 A1 | 11/2013 |
| CA | 2325226 A1 | 5/2001 |
| CA | 2512512 A1 | 7/2004 |
| CA | 2636788 A1 | 5/2008 |
| CN | 1193092 C | 3/2005 |
| CN | 1671742 A | 9/2005 |
| CN | 1878793 A | 12/2006 |
| CN | 101132811 A | 2/2008 |
| CN | 101291955 A | 10/2008 |
| CN | 100447154 C | 12/2008 |
| CN | 101366728 A | 2/2009 |
| CN | 101374538 A | 2/2009 |
| CN | 101528266 A | 9/2009 |
| CN | 101641372 A | 2/2010 |
| CN | 102076350 A | 5/2011 |
| CN | 102247392 A | 11/2011 |
| CN | 102443064 A | 5/2012 |
| CN | 103687946 A | 3/2014 |
| CN | 102711777 B | 4/2015 |
| CN | 104884076 A | 9/2015 |
| CN | 1049555470 A | 9/2015 |
| CN | 105026553 A | 11/2015 |
| CN | 107188948 A | 9/2017 |
| CN | 110494154 A | 11/2019 |
| EP | 1114862 A2 | 7/2001 |
| EP | 1459759 A1 | 9/2004 |
| EP | 0791601 B1 | 4/2005 |
| EP | 2039367 A1 | 3/2009 |
| EP | 2055308 A1 | 6/2009 |
| EP | 2284255 A1 | 2/2011 |
| EP | 2301559 A1 | 3/2011 |
| EP | 2301560 A1 | 3/2011 |
| EP | 2601971 A1 | 6/2013 |
| EP | 2703487 A1 | 3/2014 |
| EP | 2913059 A1 | 9/2015 |
| EP | 2913058 B1 | 12/2017 |
| EP | 2494977 B1 | 6/2018 |
| EP | 3556378 A1 | 10/2019 |
| EP | 3358011 B1 | 3/2020 |
| EP | 3719117 A1 | 10/2020 |
| EP | 3750553 A1 | 12/2020 |
| JP | 3018313 B2 | 3/2000 |
| JP | 2003505506 A | 2/2003 |
| JP | 3421741 B2 | 6/2003 |
| JP | 2005508913 A | 4/2005 |
| JP | 2005512507 A | 5/2005 |
| JP | 2005537253 A | 12/2005 |
| JP | 2006510619 A | 3/2006 |
| JP | 2006517537 A | 7/2006 |
| JP | 2006523085 A | 10/2006 |
| JP | 2008507505 A | 3/2008 |
| JP | 2008511300 A | 4/2008 |
| JP | 2010503630 A | 2/2010 |
| JP | 4982739 B2 | 7/2012 |
| JP | 5134772 B2 | 1/2013 |
| JP | 5814549 B2 | 11/2015 |
| KR | 10 2005 0054907 A | 6/2005 |
| KR | 20090078304 A | 7/2009 |
| KR | 101448800 B1 | 10/2014 |
| KR | 10 2015 0103660 A | 9/2015 |
| KR | 101636139 B1 | 7/2016 |
| RU | 2005102593 A | 10/2005 |
| RU | 2410125 C2 | 1/2011 |
| RU | 2010148785 A | 6/2012 |
| RU | 2599448 C2 | 10/2016 |
| WO | 0108683 A1 | 2/2001 |
| WO | 0234292 A1 | 5/2002 |
| WO | 02074337 A1 | 9/2002 |
| WO | 02088181 A2 | 11/2002 |
| WO | 02092004 A2 | 11/2002 |
| WO | 03026691 A2 | 4/2003 |
| WO | 03043651 A1 | 5/2003 |
| WO | 2004004763 A2 | 1/2004 |
| WO | 2004004770 A1 | 1/2004 |
| WO | 2004044001 A1 | 5/2004 |
| WO | 2004046345 A2 | 6/2004 |
| WO | 2004061456 A2 | 7/2004 |
| WO | 2005025604 A2 | 3/2005 |
| WO | 2005074984 A1 | 8/2005 |
| WO | 2005087797 A1 | 9/2005 |
| WO | 2006008779 A1 | 1/2006 |
| WO | 2006010628 A1 | 2/2006 |
| WO | 2006024547 A2 | 3/2006 |
| WO | 2006047820 A1 | 5/2006 |
| WO | 2006077614 A1 | 7/2006 |
| WO | 2006080434 A1 | 8/2006 |
| WO | 2006100651 A1 | 9/2006 |
| WO | 2006114805 A2 | 11/2006 |
| WO | 2007015546 A1 | 2/2007 |
| WO | 2007031100 A1 | 3/2007 |
| WO | 2007061762 A2 | 5/2007 |
| WO | 2007076200 A2 | 7/2007 |
| WO | 2007130725 A2 | 11/2007 |
| WO | 2008018641 A1 | 2/2008 |
| WO | 2008031612 A1 | 3/2008 |
| WO | 2008053892 A1 | 5/2008 |
| WO | 2008104090 A1 | 9/2008 |
| WO | 2008155659 A2 | 12/2008 |
| WO | 2009133939 A1 | 11/2009 |
| WO | 2009133940 A1 | 11/2009 |
| WO | 2009133943 A1 | 11/2009 |
| WO | 2011046570 A1 | 4/2011 |

(56) References Cited

FOREIGN PATENT DOCUMENTS

| | | |
|---|---|---|
| WO | 2011052668 A1 | 5/2011 |
| WO | 2012147470 A1 | 11/2012 |
| WO | 2014065347 A1 | 5/2014 |
| WO | 2014065348 A1 | 5/2014 |
| WO | 2014191364 A1 | 12/2014 |
| WO | 2016184795 A1 | 11/2016 |
| WO | 2016185476 A1 | 11/2016 |
| WO | 2018139562 A1 | 8/2018 |
| WO | 2018186480 A1 | 10/2018 |
| WO | 2018199107 A1 | 11/2018 |
| WO | 2019107530 A1 | 6/2019 |
| WO | 2019107566 A1 | 6/2019 |
| WO | 2019156137 A1 | 8/2019 |
| WO | 2020071520 A1 | 4/2020 |
| WO | 2020158924 A1 | 8/2020 |
| WO | 2021201260 A1 | 10/2021 |

OTHER PUBLICATIONS

SPT16 (D7I2K) Rabbit Monoclonal Antibody, from https://www.cellsignal.com/products/primary-antibodies/spt16-d7i2k-rabbit-mab/12191?N=572536551+4294956287&Nrpp=100&No=%7Boffset%7D&fromPage=plp, pp. 1-5, accessed Nov. 1, 2023.*

Kolundzic et al, FACT Sets a Barrier for Cell Fate Reprogramming in Caenorhabditis elegans and Human Cells, Developmental Cell, 2018, 46, pp. 611-626.*

Leenaars et al, Critical Steps in the Production of Polyclonal and Monoclonal Antibodies: Evaluation and Recommendations, ILAR Journal, 2005, 46, pp. 269-279.*

Li, Z. et al., "Heat-Shock Proteins," Current Protocols in Immunology, 2003, Supplement 58, A.IT.1-A.IT.6.

Li, Y. et al., "Advancement of Human Multiply, Sex health and Reproductive Medical Science," Peking University Medical Press, Mar. 2007, 1st Edition, pp. 270-271.

Li, L., et al., "Emerging Role of HMGB 1 in Fibrotic Diseases." Journal of Cellular and Molecular Medicine, 2014, 18(12): 2331-2339.

Limana, F. et al., "Exogenous High-Mobility Group Box 1 Protein Induces Myocardial Regeneration After Infarction via Enhanced Cardiac C-Kit+ Cell Proliferation and Differentiation," Circulation Research, 2005, 97(8): e73-83.

Limana, F., et al., "HMGB1 Attenuates Cardiac Remodelling in the Failing Heart via Enhanced Cardiac Regeneration and miR-206-Mediated Inhibition of TIMP-3." PLoS One, 2011, 6(6): e19845, pp. 1-11.

Lin, S. et al., "The isolation of novel mesenchymal stromal cell chemotactic factors from the conditioned medium of tumor cells." Experimental Cell Research, 2008, 314(17): 3107-3117.

Liotta, F. et al., "Toll-Like Receptors 3 and 4 Are Expressed by Human Bone Marrow-Derived Mesenchymal Stem Cells and Can Inhibit Their T-Cell Modulatory Activity by Impairing Notch Signaling." Stem Cells, 2008, 26(1): 279-289.

Liu, K.et al., "Human Placental Extract Stimulates Liver Regeneration in Rats," Biological and Pharmaceutical Bulletin, 1998, 21(1): 44-49.

Lonza BenchGuides_Poietics hMSC Human Mesenchymal Stem Cells and Media (Document # TS-PT-212-7 Apr. 2008), 2008, Walkersville, MD, USA.

Lund, L., et al., "The Registry of the International Society for Heart and Lung Transplantation: Thirty-Third Adult Heart Transplantation Report—2016; Focus Theme: Primary Diagnostic Indications for Transplant." The Journal of Heart and Lung Transplantation, 2016, 35(10): 1158-1169.

Mansbridge, J. et al., "Skin Tissue Engineering," J. Biomater, Sci. Polymer, Ed., Aug. 1, 2008, 19(8): 955-968.

Maron, B.J., et al., "Contemporary Definitions and Classification of the Cardiomyopathies—An American Heart Association Scientific Statement from the Council on Clinical Cardiology, Heart Failure and Transplantation Committee; Quality of Care and Outcomes Research and Functional Genomics and Translational Biology Interdisciplinary Working Groups; and Council on Epidemiology and Prevention." Circulation, 2006, 113: 1807-1816.

Martin-Murphy, B.V. et al., "The Role of Damage Associated Molecular Pattern Molecules in Acetaminophen-Induced Liver Injury in Mice," Toxicol Lett, Feb. 2010, 192(3): 1-20.

Maruyama, I., "Inflammation and HMGB1/RAGE system," Kekkan Igaku, 2005, 6(5): 519-525 (English translation attached).

Matsumoto, K., et al., "Up-Regulation of Hepatocyte Growth Factor Gene Expression by Inerleukin-1 in Human Skin Fibrosis," Biochemical and Biophysical Research Communications, 1992, 188(1): 235-243.

Meng, E. et al., "HMGB1 induces migration of human bone marrow-derived mesenchymal stem cells," Bulletin of the Academy of Military Medical Sciences, 2006, 30(3): 213-216 (English translation attached).

Meng, E. et al., "High Mobility Group Box 1 Protein Inhibits the Proliferation of Human Mesenchymal Stem Cells and Promotes Their Migration and Differentiation along Osteoblastic Pathway," Stem Cells and Development, 2008, 17(4): 805-814.

Merenmies, J. et al., "30-kDa Heparin-binding Protein of Brain (Amphoterin) Involved in Neurite Outgrowth," Journal of Biological Chemistry 1991, 266(25): 16722-16729.

Mistry, A.R. et al., "Recombinant HMG1 Protein Produced in Pichia pastoris: A Nonviral Gene Delivery Agent," Biotechniques, 1997, 22(4): 718-729.

Mori, T. et al., "Stem Cells/ES cells—Mesenchymal Stem Cells—Human Bone Marrow Derived Mesenchymal Stem Cells," Saisei Iryou—Regenerative Medicine, 2005, 4(3): 421-429, 351.

Morosetti, R. et al., "MyoD expression restores defective myogenic differentiation of human mesoangioblasts from Inclusion-body myositis muscle," PNAS, Nov. 7, 2006, 103(45): 16995-17000.

Mouse care guidance from the Institutional Animal Care and Use Committee at University of California, San Francisco; iacuc.ucsf.edu/Policies/BloodCollectionMice.doc; accessed May 15, 2014.

Muhamed, J. et al., "Phenotypic Modulation of Cell Types around Implanted Polyethylene Terephthalate Fabric in Rabbit Muscle." Toxicologic Pathology, 2013, 41: 497-507.

Muhammad, S. et al., "The HMGB1 Receptor RAGE Mediates Ischemic Brain Damage." The Journal of Neuroscience, Nov. 12, 2008, 28(46): 12023-12031.

Müller, S. et al., "The double life of HMGB1 chromatin protein: architectural factor and extracellular signal," EMBO Journal, 2001, 20(16): 4337-4340.

Musumeci, D., et al., "An overview on HMGB1 inhibitors as potential therapeutic agents in HMGB1-related pathologies." Pharmacology & Therapeutics, 2014, 141: 347-357.

Nakajima et al., "Dynamics and Role of High Mobility Group Box-1 (HMGB-1) in Injured Spinal Cord," Nihon Seikei Geka Gakkai Zasshi (J. Jpn. Orthop. Assoc.), 2010, 84(8): S1050.

Nakamura, K. et al., "p38 Mitogen-Activated Protein Kinase Functionally Contributes to Chondrogenesis Induced by Growth/Differentiation Factor-5 in ATDC5 Cells," Experimental Cell Research, 1999, 250(2): 351-363.

Nakanishi, S., et al., "Membrane Potential-Regulated Ca2+ Signalling in Development and Maturation of Mammalian Cerebellar Granule Cells." J. Physiol., 2006, 575(2): 389-395.

Narumi, T., et al., "High-Mobility Group Box 1-Mediated Heat Shock Protein Beta 1 Expression Attenuates Mitochondrial Dysfunction and Apoptosis." Journal of Molecular and Cellular Cardiology, 2015, 82: 1-12.

Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science ), 2015, 33(2): 126-127. http://www.lib.yamagata-u.ac.jp/alllib/elib/kiyou/kiyoum/kiyoum-33-2/image/kiyoum-33-2-125to131.pdf.

NCBI, "Old myocardial infarction." MedGen UID: 57612, retrieved from internet Jan. 19, 2022, <https://www.ncbi.nlm.nih.gov/medgen/57612>.

Nickoloff, B. J., et al., "Recent Insights into the Immunopathogenesis of Psoriasis Provide new Therapeutic Opportunities." J. Clin. Invest., 2004, 113(12): 1664-1675.

(56) References Cited

OTHER PUBLICATIONS

NPM_Human, Accession No. P06748, accessed Jan. 19, 2022.
O'Callaghan, A., et al., "HMGB1 as a Key Mediator of Tissue Response to Injury: Roles in Inflammation and Tissue Repair." European Surgery, 2006, 38: 283-292.
Opitz, C.E. et al., "Toll-Like Receptor Engagement Enhances the Immunosuppressive Properties of Human Bone Marrow-Derived Mesenchymal Stem Cells by Inducing Indoleamine-2, 3-dioxygenase-1 via Interferon-β and Protein Kinase R," Stem Cells, 2009, 27(4): 909-919.
Otsuru, S. et al., "BMP-2 mobilizes robust bone marrow mesenchymal progenitor cells to the circulating blood in pone regeneration," The 28th Meeting of the Molecular Biology Society of Japan, 2005, 733(3P-1012) (translated English abstract attached).
Ozaki, Y. et al., "Comprehensive Analysis of Chemotactic Factors for Bone Marrow Mesenchymal Stem Cells," Stem Cells and Development, 2007, 16(1): 119-129.
PA2G4_Human, Accession No. Q9UQ80, Apr. 2001.
Palumbo, R. et al., "Extracellular HMGB1, a signal of tissue damage, induces mesoangioblast migration and proliferation," The Journal of Cell Biology, 2004, 164(3): 441-449.
Palumbo, R. et al., "High mobility group box 1 protein, a cue for stem cell recruitment," Biochemical Pharmacology, 2004, 68(6): 1165-1170.
Palumbo, R. et al., "Cells migrating to sites of tissue damage in response to the danger signal HMGB1 require NF-κB activation," Journal of Cell Biology, 2007, 179(1): 33-40.
Pandya, N.M., et al., "Angiogenesis—A New Target for Future Therapy." Vascular Pharmacology, 2006, 44: 265-274.
Panepucci, R.A. et al., "Abstract # 4427: Comparison of Gene Expression of Mesenchymal Stem Cells from the Umbilical Cord and from the Bone Marrow," Blood, Nov. 2003, 16(102): Abstract.
Panepucci, R. A. et al., "Comparison of Gene Expression of Umbilical Cord Vein and Bone Marrow-Derived Mesenchymal Stem Cells." Stem Cells, Dec. 2004, 22(7): 1263-1278.
Pankov, R. et al., Fibronectin at a glance, J. Cell Sci., Oct. 2002, 115(20): 3861-3863.
Park, J., et al., "Involvement of Toll-Like Receptors 2 and 4 in Cellular Activation by High Mobility Group Box 1 Protein." Journal of Biological Chemistry, 2004, 279(9): 7370-7377.
Paul, S.R. et al., "Stromal Cell-Associated Hematopoiesis: Immortalization and Characterization of a Primate Bone Marrow-Derived Stromal Cell Line," Blood, 1991, 77(8): 1723-1733.
Pevsner-Fischer, M. et al., "Toll-like receptors and their ligands control mesenchymal stem cell functions," Blood, 2007, 109(4): 1422-1432.
PFD5_Human, Accession No. Q99471, Nov. 1997.
Telusma, G. et al., "Dendritic cell activating peptides induce distinct cytokine profiles," International Immunology, 2006, 18(11): 1563-1573.
Teoh, N., et al., "Low-Dose TNF-Alpha Protects Against Hepatic Ischemia-Reperfusion Injury In Mice: Implications for Preconditioning." Hepatology, 2003, 37(1): 118-128.
Thorey, I.S. et al., "The Ca2+-binding Proteins S100A8 and S100A9 Are Encoded by Novel Injury-regulated Genes*," Journal of Biological Chemistry, 2001, 276(38): 35818-35825.
Tokuriki, N., et al., "Stability Effects of Mutations and Protein Evolvability." Current Opinion in Structural Biology, 2009, 19: 596-604.
Tsung, A., et al., "Hepatic Ischemia/Reperfusion Injury Involves Functional TLR4 Signaling in Nonparenchymal Cells." The Journal of Immunology, 2005, 175(11): 7661-7668.
Türker, S. et al., "Nasal route and drug delivery systems," Pharmacy World and Science, 2004, 26: 137-142.
Uchida et al., "Nihon Seikei Geka Gakkai Zasshi," The Journal of Japanese Orthopaedic Surgical Society, 2005, 79(8): S832, 1-P6-6. (English translation attached, titled "The chemotactic activity of PDGF-bb BMP-2, and FGF-2 towards committed and uncommitted mesenchymal stem cells").
Ueta, M., et al., "Intracellularly Expressed TLR2s and TLR4s Contribution to an Immunosilent Environment at the Ocular Mucosal Epithelium." The Journal of Immunology, 2004, 173(5): 3337-3347.
Ulloa, L. et al., "High-mobility group box 1 (HMGB1) protein: Friend and foe," Cytokine & Growth Factor Reviews, 2006, 17: 189-201.
Uronen-Hansson, H., et al., "Toll-like Receptor 2 (TLR2) and TLR4 are Present Inside Human Dendritic Cells, Associated with Microtubules and the Golgi Apparatus but are not Detectable on the Cell Surface: Integrity of Microtubules is Required for Interleukin-12 Production in Response to Internalized Bacteria." Immunology, 2004, 111: 173-178.
User Manual for StemCell Technologies, "Enumeration, Expansion, and Differentiation of Human Mesenchymal Progenitor Cells Using MesenCult." StemCell Technologies, Oct. 2007, Version 2.2.0.
Vandal, K. et al., "Blockade of S100A8 and S100A9 Suppresses Neutrophil Migration in Response to Lipopolysaccharide." The Journal of Immunology, Sep. 1, 2003, 171(5): 2602-2609.
Venereau, E. et al., "Mutually exclusive redox forms of HMGB1 promote cell recruitment or proinflammatory cytokine release." The Journal of Experimental Medicine, 2012, 209(9): 1519-1528.
Walfish, A.E., et al., "Crohn Disease (Regional Enteritis; Granulomatou Ileitis; Granulomatous Ileocolitis)," Merck Manual Professional Version, 2020, pp. 1-7.
Walfish, A.E., et al., "Overview of Inflammatory Bowel Disease," Merck Manual Professional Version, 2020, pp. 1-3.
Walfish, A.E., et al., "Ulcerative Colitis," Merck Manual Professional Version, 2020, pp. 1-8.
Wang, H. et al., "HMG-1 as a Late Mediator of Endotoxin Lethality in Mice," Science, 1999, 285(5425): 248-251.
Wang, L. et al., "Ischemic cerebral tissue and MCP-1 enhance rat bone marrow stromal cell migration in interface culture," Experimental Hematology, 2002, 30: 831-836.
Wang, H. et al., "Kansaibou no riron to gijutu," Science Press, Mar. 2005, 5: 58-61 (English translation attached, titled "Theories and Technologies for Stem Cells").
Wang, H.L. et al., "High mobility group protein B1 and the research progress of its biological effect," Journal of Chinese Modern Surgery, 2006, 3(22): 1806-1809 (English translation attached).
Wang, H. Y., et al., "Rate of Evolution in Brain-Expressed Genes in Humans and Other Primates." PLoS Biol., 2007, 5(2): e13.
Wang, Y., "Biology of hematopoietic stem cell and the research method therof," Science Press, Mar. 2007, 1st Edition, pp. 56-58.
Wang, W. et al., "Intravenous administration of bone marrow mesenchymal stromal cells is safe for the lung in a chronic myocardial infarction model," Regen Med, Mar. 2011, 6(2): 179-190.
Wang, F.-C., et al., "Overexpression of HMGB1 A-box reduced lipopolysaccharide-induced intestinal inflammation via HMGB1/ TLR4 signaling in vitro." World J Gastroenterol, Jul. 7, 2015, 21(25): 7764-7776.
Watanabe, T., et al., "The Role of HMGB-1 on the Development of Necrosis During Hepatic Ischemia and Hepatic Ischemia/ Reperfusion Injury in Mice." Journal of Surgical Research, 2005, 124: 59-66.
Weintraub, R. G., et al. "Dilated cardiomyopathy." The Lancet 390.10092 (2017): 400-414.
Wexler, S. et al., "Adult Bone Marrow is a Rich Source of Human Mesenchymal 'Stem' Cells but Umbilical Cord and Mobilized Adult Blood are Not," British Journal of Haematology, 2003, 121(2): 368-374.
Whisstock, J. C., et al., "Prediction of Protein Function from Protein Sequence and Structure." Quarterly Reviews of Biophysics, 2003, 36(3): 307-340.
Wilgus, T. A., et al. "Neutrophils and wound repair: positive actions and negative reactions." Advances in wound care 2.7 (2013): 379-388.
Witkowski, A., et al., "Conversion of a B-Ketoacyl Synthase to a Malonyl Decarboxylase by Replacement of the Active-Site Cysteine with Glutamine." Biochemistry, 1999, 38: 11643-11650.
Wolf, G. et al., "From the Periphery of the Glomerular Capillary Wall Toward the Center of Disease," Diabetes, Jun. 2005, 54(6): 1626-1634.

(56) References Cited

OTHER PUBLICATIONS

Woodbury, D. et al., "Adult Rat and Human Bone Marrow Stromal Cells Differentiate into Neurons," Journal of Neuroscience Research, Aug. 15, 2000, 61(4): 364-370.
Wu, Y. et al., "Mesenchymal Stem Cells Enhance Wound Healing Through Differentiation and Angiogenesis," Stem Cells, 2007, 25(10): 2648-2659. Epub Jul. 5, 2007.
Yamada, T. et al., "Regulation of osteoclast development by Notch signaling directed to osteoclast precursors and through stromal cells," Blood, Mar. 2003, 101(6): 2227-2234.
Yamaoka, S., et al., "1043 Systemic delivery of HMGB1 peptide ameliorates imiquimod-induced psoriasis-like dermatitis." Journal of Investigative Dermatology, 2018, 138(5): S177.
Yang, D. et al., "High mobility group box-1 protein induces the migration and activation of human dendritic cells and acts as an alarmin," Journal of Leukocyte Biology, 2007, 81(1): 59-66. Epub Sep. 11, 2006.
Yang, H., et al., "Reversing established sepsis with antagonists of endogenous high-mobility group box 1." Proceedings of the National Academy of Sciences, 2004, 101(1): 296-301.
Yang, S., et al., "Does Pretreatment of Bone Marrow Mesenchymal Stem Cells with 5-Azacytidine or Double Intravenous Infusion Improve Their Therapeutic Potential for Dilated Cardiomyopathy?" Medical Science Monitor Basic Research, 2013, 19: 20-31.
YBOX1_Human, Accession No. P67809, accessed Nov. 10, 2021.
Youn, J.H. et al., "High Mobility Group Box 1 Protein Binding to Lipopolysaccharide Facilitates Transfer of Lipopolysaccharide to CD14 and Enhances Lipoplysaccharide-Mediated TNF-α Production in Human Monocytes," Journal of Immunology, 2008, 180(7): 5067-5074.
Yu, Q., et al., "Impact of Repeated Intravenous Bone Marrow Mesenchymal Stem Cells Infusion on Myocardial Collagen Network Remodeling in a Rat Model of Doxorubicin-Induced Dilated Cardiomyopathy." Molecular and Cellular Biochemistry, 2014: 279-285.
Yuan, Y. et al., "Differentiation of Mesenchymal Stem Cells in Cardiomyogenic Cells Under the Induction of Myocardial Cell Lysate," Chinese Journal of Cardiology, 2005, 33(2): 170-173.
Zheng, X., et al., "Adeno-associated virus-mediated colonic secretory expression of HMGB1 A box attenuates experimental colitis in mice." J Gene Med, 2016, 18(10): 261-272.
Zhou, X. et al., "Exogenous High-Mobility Group Box 1 Protein Injection Improves Cardiac Function after Myocardial Infarction: Involvement of Wnt Signaling Activation," Journal of Biomedicine and Biotechnology, 2012, vol. 2012, pp. 1-5.
Zhou, X., et al., "Section 2 The translation process of genetic information." Molecular Genetics, 1992, pp. 141-143.
Zhou, Y.-H., et al., "High mobility group box 1 protein attenuates myocardial ischemia reperfusion injury via inhibition of the p38 mitogen-activated protein kinase signaling pathway." Experimental and Therapeutic Medicine, 2017, 14: 1582-1588.
Gueukdjian S.A., "Intra-Arterial Injections in the Treatment of Peripheral Vascular Disease," Postgrad Medical Journal, Jan. 1955, 31(351): 30-31.
Guillot, L., et al., "Response of Human Pulmonary Epithelial Cells to Lipopolysaccharide Involves Toll-like Receptor 4 (TLR4)-dependent Signaling Pathways." Journal of Biological Chemistry, Jan. 2004, 279(4): 2712-2718.
Guo, J., et al., "Monocyte Chemotactic Protein-1 Promotes the Myocardial Homing of Mesenchymal Stem Cells in Dilated Cardiomyopathy." International Journal of Molecular Sciences, 2013, 14: 8164-8178.
Harris, H.E., et al., "Alarmin(g) news about danger," EMBO Reports, 2006, 7(8): 774-778.
Harrison, C.A., et al., "Oxidation Regulates the Inflammatory Properties of the Murine S100 Protein S100A8." J. Biol. Chem., 1999, 274(13): 8561-8569.
Healthwise Staff, "Age-related Macular Degeneration," University of Michigan Health System, Aug. 2015, https:www.uofmhealth.org/health-library/hw176039.

He, Y.T., et al., "HMGB1 Ameliorates Inflammatory Bowel Disease by Inducing Circulating Mesenchymal Stem Cells." The 17th Congress of the Japanese Society for Regenerative Medicine, 2018, 34, Abstract.
Heil, M. et al., "An engineered heparin-binding form of VEGF-E (hbVEGF-E)," Angiogenesis, 2003, 6(3): 201-211.
Herrera, M.B. et al., "Exogenous mesenchymal stem cells localize to the kidney by means of CD44 following acute tubular injury," Kidney International, 2007, 72: 430-441.
Hiratsuka S. et al., "Tumour-mediated upregulation of chemoattractants and recruitment of myeloid cells predetermines lung metastasis," Natural Cell Biology, Dec. 2006, 8(12): 1369-1375.
Himgbiotech, "BoxA from HMGB1, human & mouse, LPS-free." HMGBiotech Srl, 2008, C.F. e P.IVA 04942740962, http://www.hmgbiotech.com/products.php?ID=91, ,accessed Jan. 27, 2017 from internet>.
HMGBiotech, "BoxA from HMGB1, human & mouse, LPS-free-Datasheet." HMGBiotech Srl, 2008, Via Moretto da Brescia 25, 20133—Milano, Italy, http://www.hmgbiotech.com/upload/documenti/0515122144_boxa.
"HNRPK_Human", NCBI_TaxID=9606, Accession No. P61978, Jun. 2004.
Hori, O. et al., "The Receptor for Advanced Glycation End Products (RAGE) Is a Cellular Binding Site for Amphoterin," Journal of Biological Chemistry, 1995, 270(43): 25752-25761.
Hornef, M.W., et al., "Toll-like Receptor 4 Resides in the Golgi Apparatus and Colocalizes with Internalized Lipopolysaccharide in Intestinal Epithelial Cells." J. Exp. Med., 2002, 195(5): 559-570.
Hruby, V.J., "Designing Peptide Receptor Agonists and Antagonists." Nature Reviews Drug Discovery, 2002, 1: 847-858.
Hu, Z., et al. "Role of high-mobility group box 1 protein in inflammatory bowel disease." Inflammation Research 64.8(2015): 557-563.
Huttunen, H.J. et al., "Receptor for Advanced Glycation End Products-binding COOH-terminal Motif of Amphoterin Inhibits Invasive Migration and Metastasis," Cancer Research, 2002, 62: 4805-4811.
Ichinose, K., et al., "Antiangiogenic Endostatin Peptide Ameliorates Renal Alterations in the Early Stage of a Type 1 Diabetic Nephropathy Model." Diabetes, Oct. 2005, 54(10): 2891-2903.
Instruction Manual of HiTrap chelating HP (Amersham Biosciences), 2003, pp. 1-6.
Ishikane, S., "Therapeutic application of allogenic fetal membrane-derived mesenchymal stem cells transplantation in regenerative medicine," Pharmaceutical Bulletin of Fukuoka University, Mar. 2011, 11(0): 17-25.
Ishikane, Shin, et al., "Development of multi-growth factor secreted fetal membrane-derived mesenchymal stem cell sheets." Grants-in-Aid for Scientific Research, 2014, pp. 1-6.
Jansen, J. et al., "Transplantation of hematopoietic stem cells from the peripheral blood," Journal of Cellular and Molecular Medicine, 2005, 9(1): 37-50.
Jayaraman, L. et al., "High mobility group protein-1 (HMG-1) is a unique activator of p53," Genes & Development, 1998, 12(4): 462-472.
Jiang, Y. et al., "Pluripotency of mesenchymal stem cells derived from adult marrow," Nature, 2002, 418(6893): 41-49.
Jiao, C. et al., "Researchers find nerve damage may precede diabetic retinopathy," EurekAlert! Science News, Apr. 2016, https://www.eurekalert.org/pub_releases/2016-04/uoih-rfv042616.php.
Jin, Y., "Isolating culture and induced differentiation of marrow mesenchyma stem cells," Principles and Protocols of Tissue Engineering, Jun. 2004, 277-278 (English translation attached).
Kaneda, et al., "Tissue repair mechanism by bone-marrow-derived stem cells." Experimental Mediciner, 2013, 31(5): 655-661.
Kassis, I. et al., "Isolation of mesenchymal stem cells from G-CSF mobilized human peripheral blood using fibrin microbeads," Bone Marrow Transplantation, 2006, 37(10): 967-976.
Kawabata, H. et al., "High Mobility Group Box 1 Is Upregulated After Spinal Cord Injury and Is Associated With Neuronal Cell Apoptosis," Spine, 2010, 35(11): 1109-1115.

(56) References Cited

OTHER PUBLICATIONS

Kern, S. et al., "Comparative Analysis of Mesenchymal Stem Cells from Bone Marrow, Umbilical Cord Blood, or Adipose Tissue," Stem Cells, 2006, 24(5): 1294-1301.

Kessler, M.W. et al., "Tissue Engineering and Cartilage," Organogenesis, Jan. 2008, 4(1): 28-32.

Kido, T., et al., "Abstract 15756: The Administration of High-morbidity Group Box 1 Fragment Prevents Deterioration of Cardiac Performance by Enhancement of Bone-marrow Mesenchymal Stem Cells Homing in the Delta-sarcoglycan-deficient Hamster." Circulation, Nov. 2017, 136(Suppl 1): Abstract.

Kikuchi, K. et al., "HMGB1 as a therapeutic target in spinal cord injury: A hypothesis for novel therapy development (Review)," Experimental and Therapeutic Medicine, 2011, 2: 767-770.

Kikuchi, K. et al., "Systemic administration of HMGB1 improves bleomycin-induced skin fibrosis by locally accumulating bone marrow mesenchymal stem cells." Regenerative Medicine, Feb. 1, 2017, 16: 422.

Kim, S. et al., "Skin Regeneration Using Keratinocytes and Dermal Fibroblasts Cultured on Biodegradable Microspherical Polymer Scaffolds," Journal of Biomedical Materials Research Part B: Applied Biomaterials, 2005, 75(2): 369-377.

Kirov, S.A. et al., "In Vivo 2-Photon Microscopy Reveals G-CSF Enhanced Mobilization and Targeting of Neo-Endogenous Bone Marrow Stromal Cells to Stroke Injury Sites," Stroke, Apr. 2009, 40(4): 1-2, e133, Abstract No. 107.

Kitahara, T. et al., "High-Mobility Group Box 1 Restores Cardiac Function After Myocardial Infarcation in Transgenic Mice," Cardiovascular Research, European Society of Cardiology, Oct. 1, 2008, 80: 40-46.

Koc, O. et al., "Mesenchymal Stem Cells: Heading into the Clinic," Bone Marrow Transplantation, 2001, 27(3): 235-239.

Kohno, T. et al., "High Mobility Group Box 1 Protein is Associated With Post-Infarction Healing Process and Left Ventricular Remodeling," Circ. J., 2008, 72, Supplement 1, P J-004: 510-511.

Kokkola, R., et al., "Rage is the Major Receptor for the Proinflammatory Activity of HMGB1 in Rodent Macrophages." Scandinavian Journal of Immunology, 2005, 61: 1-9.

Komurasaki, Y., et al., "555 Systemic HMGB1 Administration Ameliorated Bleomycin-Induced Skin Fibrosis by Promoting Accumulation of Bone Marrow-Derived Mesenchymal Stem Cells to the Lesion." Journal of Investigative Dermatology, 2016, 136(9): S255.

Komurasaki, Y., et al., "HMGB1 Ameliorates Bleomycin-Induced Skin Fibrosis by Promoting Accumulation of Mesenchymal Stem Cells to the Lesion." The 48th Annual Meeting of the Japanese Society of Matrix Biology and Medicine, 2016: 78.

Koren-Morag, N., et al., "White Blood Cell Count and the Incidence of Ischemic Stroke in Coronary Heart Disease Patients." The American Journal of Medicine, 2005, 118: 1004-1009.

Laflamme, M. et al., "Regenerating the heart," Nature Biotechnology, Jul. 2005, 23(7): 845-856.

Lanza, R. et al., "Essentials of Stem Cell Biology—Chapter 27, Mesenchymal Stem Cells," Elsevier Academic Press, 2006, pp. 205-210.

La Rosa, T.J. et al., "Glycine max protein SEQ ID No. 211221," Geneseq Accession No. AFQ20044, 2007.

Lemp, M.A., et al., "The Definition and Classification of Dry Eye Disease: Report of the Definition and Classification Subcommittee of the International Dry Eye Workshop (2007)." The Ocular Surface, Apr. 2007, 5(2): 75-92, Abstract only.

Liao, D., et al. "Vascular smooth cell proliferation in perfusion cluture of porcine carotid arteries." Biochemical and biophysical research communications 372.4 (2008): 668-673.

Li, S. et al., "Millennium Review, Nonviral gene therapy: promises and challenges," Gene Ther., 2000, 7: 31-34.

Ahrens, N., et al. "Mesenchymal Stem Cell Content of Human Vertebral Bone Marrow." Transplantation 78(6): 925-929, (Year: 2004).

Aikawa, E., et al. "HMGB1 accelerates skin regeneration by inducing bone marrow mesenchymal stromal cells." Journal of Dermatological Science 84(1): 1-14, (Year: 2016).

Alshorafa, A. K., et al. "Psoriasis is associated with low serum levels of hydrogen sulfide, a potential anti-inflammatory molecule." The Tohoku Journal of Experimental Medicine 228.4 (2012): 325-332.

Andersson, U. et al. "HMGB1 is a Therapeutic Target for Sterile Inflammation and Infection." Annu Rev Immunol. 29: 139-162 (Year: 2011).

Andrassy, M., et al. "High-Mobility Group Box-1 in Ischemia-Reperfusion Injury of the Heart." Circulation 117(25): 3216-3226, (Year: 2008).

Baer, P. C. et al. "Comprehensive Phenotypic Characterization of Human Adipose-Derived Stromal/Stem Cells and Their Subsets by a High Throughput Technology." Stem Cells and Development 00(00):1-10, (Year: 2012).

Bhattacharya, R. et al. "Impact of genetic variation on three dimensional structure and function of proteins." PloS one, 12(3): 1-22, Mar. 15, 2017.

Bigazzi, P. E., et al. "Introduction to Review Series on Animal Models of Human Disease." Clinical Immunology and Immunopathology, 74(1): 1, (Year: 1995).

Bretag, A. "Too much hype, not enough hope: Are balanced reporting and proper controls too much to expect from therapeutic studies in animal models of neuromuscular diseases that presage clinical trials in humans?" Neuromuscular Disorders 17:203-205 (Year: 2007).

Charles River Laboratories Ineternational, Inc., Research Models, C57BL/6 Mice, Nomenclature: C57BL/6NCrl, 2019. Retrieved from: https://www.criver.com/sites/default/files/resources/doc_a/C57BL6MouseModelInformationSheet.pdf.

Del Buono, M. G., et al. "Ischemic Cardiomyopathy and Heart Failure After Acute Myocardial Infarction." Current Cardiology Reports, 24(10): 1505-1515, Aug. 16, 2022.

Fenton, A. W. et al. "Rheostat positions: a new classification of protein positions relevant to pharmacogenomics." Medicinal Chemistry Research 29:1133-1146, (Year: 2020).

Freitag, J., et al. "The effect of autologous adipose derived mesenchymal stem cell therapy in the treatment of a large osteochondral defect of the knee following unsuccessful surgical intervention of osteochondritis dissecans—a case study." BMC Musculoskeletal Disorders 18(298):1-11, (Year: 2017).

Funayama, A., et al. "Cardiac nuclear high mobility group box 1 prevents the development of cardiac hypertrophy and heart failure." Cardiovascular Research 99(4): 657-664, (Year: 2013).

Goodman, W. A., et al. "IL-6 signaling in psoriasis prevents immune suppression by regulatory T cells." The Journal of Immunology 183.5 (2009): 3170-3176.

Grossman, R. M., et al. "Interleukin 6 is expressed in high levels in psoriatic skin and stimulates proliferation of cultured human keratinocytes." Proceedings of the National Academy of Sciences 86.16 (1989): 6367-6371.

Guo, H. H., et al. "Protein tolerance to random amino acid change." Proceedings of the National Academy of Sciences 101(25):9205-9210, Jun. 22, 2004.

He, Y., et al. "Exogenous High-Mobility Group Box 1 Protein Prevents Postinfarction Adverse Myocardial Remodeling Through TGF-β/Smad Signaling Pathway." Journal of Cellular Biochemistry 114: 1634-1641, (Year: 2013).

Hinderer, S., et al. "Cardiac fibrosis—A short review of causes and therapeutic strategies." Advanced drug delivery reviews 146 (2019): 77-82.

Justice, M. J., et al. "Using the mouse to model human disease: increasing validity and reproducibility." Dis Model Mech. 9(2):101-103, Feb. 1, 2016.

Kaneko, M., et al. "Abstract 11250: Bone Marrow Mononuclear Cell Transplantation Improves Cardiac Function in Ischemic Cardiomyopathy via High Mobility Group Box 1 Released from Dead Donor Cells." Circulation 126:A11250, Mar. 28, 2018.

Kwak, M. S., et al. "Immunological significance of HMGB1 post-translational modification and redox biology." Frontiers in immunology 11 (2020): 1-16.

(56) References Cited

OTHER PUBLICATIONS

Lee, S.-A., et al. "The role of high mobility group box 1 in innate immunity." Yonsei medical journal 55.5 (2014): 1165-1176.
Lee, G., et al. "Fully reduced HMGB1 accelerates the regeneration of multiple tissues by transitioning stem cells to Galert." Proceedings of the National Academy of Sciences, 115(19): E4463-E4472, Apr. 19, 2018.
Li, D. C. J. "Research progress on the mechanism and induction methods for the differentiation of mesenchymal stem cells." Infect Inflamm Rep, vol. 12, No. 1, Mar. 2011: 62-64.
Lotze, M., et al. "High-mobility group box 1 protein (HMGB1): Nuclear weapon in the immune arsenal." Nature Reviews Immunology 5(4):331-342, (Year: 2005).
Morikawa, S., et al. "Prospective identification, isolation, and systemic transplantation of multipotent mesenchymal stem cells in urine bone marrow." The Journal of Experimental Medicine 206(11):2483-2496, (Year: 2009).
Narumi, T., et al. "Abstract 15265: Cardiac-specific Overexpression of High-Mobility Group Box 1 Protects Cardiomyocyte from Apoptosis During the Pathogenesis of Doxorubicin Cardiomyopathy." Circulation, 126:A15265, Mar. 28, 2018.
Neuner, P., et al. "Increased IL-6 production by monocytes and keratinocytes in patients with psoriasis." Journal of Investigative Dermatology 97.1 (1991): 27-33.
Nojiri, S., et al. "Synthesized HMGB1 peptide attenuates liver inflammation and suppresses fibrosis in mice." Inflammation and Regeneration 41(28):1-15, (Year: 2021).
Paola, R. D., et al. "S-acetyl-glutathione attenuates carbon tetrachloride-induced liver injury by modulating oxidative imbalance and inflammation." International journal of molecular sciences 23.8 (2022): 4429.
PROCR gene—Protein C Receptor. Downloaded from https://www.genecards.org/cgi-bin/carddisp.pl?gene=PROCR, accessed Mar. 31, 2023.
Scholten, D., et al. "The carbon tetrachloride model in mice." Laboratory animals 49.1_suppl (2015): 4-11.
Shedoeva, A., et al. "Wound healing and the use of medicinal plants." Evidence-Based Complementary and Alternative Medicine: 1-31 (2019).
Sidney, L. E. "Concise Review: Evidence for CD34 as a Common Marker for Diverse Progenitors." Stem Cells 32(6): 1380-1389, Feb. 4, 2014.
Sisakian, H. S. et al. "Dilated Cardiomyopathy: Evoltion of Pathogenesis Concepts and Potential for New Therapies." New Armenian Medical Journal 9(1):4-18, (Year: 2015).
Suchacki, K. J. "Bone marrow adipose tissue: formation, function and regulation." Current opinion in Pharmacology 28:50-56, (Year: 2016).
Tamai, K. et al. U.S. Appl. No. 18/152,249, "Pharmaceuticals That Promote Functional Regeneration of Damaged Tissues." filed Jan. 10, 2023.
Tamai, K. et al. "179 Systemic administration of HMGB1 peptide drastically improves survival of the RDEB model mice by mobilizing multipotent stem/progenitor cells from bone marrow", Journal of Investigative Dermatology, vol. 137, No. 10, Supplement 2, 2017: S223.
Taniguchi, N. et al. "Stage-Specific Secretion of HMGB1 in Cartilage Regulates Endochondral Ossification." Molecular and Cellular Biology, 27(16):5650-5664, (Year:2007).
WHO Drug Information, vol. 32, No. 1, Appendix 5, p. 155, (Year: 2018).
Wynn, T. A., et al. "Mechanisms of fibrosis: therapeutic translation for fibrotic disease." Nat Med. 18(7): 1028-1040, (Year: 2013).
Yang, H. et al. "The many faces of HMGB1: molecular structure-functional activity in inflammation, apoptosis, and chemotaxis." J. Leukoc Biol. 93(6): 865-873, (Year: 2013).
Yang, Y.-H. K., et al. "Changes in phenotype and differentiation potential of human mesenchymal stem cells aging in vitro." Stem cell research & therapy 9 (2018): 1-14.
Younis, S., et al. "Tumor necrosis factor-associated palmoplantar pustular psoriasis treated with interleukin 6 blocker." The Journal of Rheumatology 39.10 (2012): 2055-2056.
Zandarashvili, L., et al. "Real-time kinetics of high-mobility group box 1 (HMGB1) oxidation in extracellular fluids studied by in situ protein NMR spectroscopy." Journal of Biological Chemistry 288. 17 (2013): 11621-11627.
Zhao, J., et al. "The Study Progression of the Role of HMGBI in Ichemic Heart Failure." Molecular Cardiology of China, pp. 1169-1171, Dec. 25, 2014.
Pittenger, M. et al., "Multilineage Potential of Adult Human Mesenchymal Stem Cells," Science, 1999, 284(5411): 143-147.
NPM_Human, Accession No. P06748, Jan. 1988.
Popovic, K. et al., "Increased Expression of the Novel Proinflammatory Cytokine High Mobility Group Box Chromosomal Protein 1 in Skin Lesions of Patients With Lupus Erythematosus," Arthritis & Rheumatism, 2005, 52(11): 3639-3645.
PRS6A_Human, Accession No. P17980, Nov. 1990.
Pusterla, T. et al., "High mobility group B2 is secreted by myeloid cells and has mitogenic and chemoattractant activities similar to high mobility group B1," Autoimmunity, 2009, 42(4): 308-310.
Quertainmont, R. et al., "Mesenchymal Stem Cell Graft Improves Recovery after Spinal Cord Injury in Adult Rats through Neurotrophic and Pro-Angiogenic Actions," PLoS One, Jun. 2012, 7(6): 1-15, e39500.
Racanelli, V., et al., "The Liver as an Immunological Organ." Hepatology, 2006, 43(2): Suppl. 1—S54-S62.
Rahimi-Movaghar, V. et al., "Effect of Decompression on Complete Spinal Cord Injury in Rats," International Journal of Neuroscience, 2008, 118: 1359-1373.
Raicevic, G. et al., "Inflammation modifies the pattern and the function of Toll-like receptors expressed by human mesenchymal stromal cells," Human Immunology, 2010, 71(3): 235-244.
Raucci, A., et al., "The Janus Face of HMGB1 in Heart Disease: A Necessary Update." Cellular and Molecular Life Sciences, 2019, 76: 211-229.
Robinson, M.J. et al., "The S100 Family Heterodimer, MRP-8/14, Binds with High Affinity to Heparin and Heparan Sulfate Glycosaminoglycans on Endothelial Cells," Journal of Biological Chemistry, 2002, 277(5): 3658-3665.
Ross, M.H., et al., "Histology: a Text and Atlas: With Correlated Cell and Molecular Biology." Lippincott Williams & Wilkins, 2018.
Ryckman, S. et al., "Proinflammatory Activities of S100: Proteins S100A8, S100A9, and S100A8/A9 Induce Neutrophil Chemotaxis and Adhesion." J. Immunol., 2003, 170(6): 3233-3242.
Santamaria-Kisiel, L. et al., "Calcium-dependent and -independent interactions of the S100 protein family." Biochem. J., 2006, 396: 201-214.
Sasaki, M. et al., "Mesenchymal Stem Cells Are Recruited into Wounded Skin and Contribute to Wound Repair by Transdifferentiation into Multiple Skin Cell Type." The Journal of Immunology, Feb. 15, 2008, 180(4): 2581-2587.
Saver, J.L., "Time Is Brain-Quantified." Stroke, Jan. 2006, 37: 263-266.
Schaffer, M. R. et al., "Wound Fluid Inhibits Wound Fibroblast Nitric Oxide Synthesis." Journal of Surgical Research, 2004, 122(1): 43-48.
Schon, M. P., Boehncke, W. H., "Medical Progress: Psoriasis." The New England Journal of Medicine, May 2005, 352(18): 1899-1912.
Scoote, M., et al., "Chapter 19—Pathophysiology of Heart Failure." Essential Cardiology: Principles and Practice, 2006, 2nd Edition, Chapter 19, pp. 347-369.
Seffernick, J. L., "Melamine Deaminase and Atrazine Chlorohydrolase: 98 Percent Identical but Functionally Different." Journal of Bacteriology, 2001, 183(8): 2405-2410.
Selected cardiac diagnoses and ICD-10 codes, 2021, 1 page.
Seong, YS., Matzinger, P., "Hydrophobicity: an ancient damage-associated molecular pattern that initiates innate immune responses." Nature Reviews: Immunology, Jun. 2004, 4(6): 469-478.
Shibata, F. et al., "Fibroblast growth-stimulating activity of S100A9 (MRP-14)." Eur. J. Biochem., Feb. 2004, 271(11): 2137-2143.

(56) References Cited

OTHER PUBLICATIONS

Shing, Y et al., "Heparin Affinity: Purification of a Tumor-Derived Capillary Endothelial Cell Growth Factor." Science, Mar. 23, 1984, 223: 1296-1299.
Simard, A. R., et al., "Bone Marrow-Derived Microglia Play a Critical Role in Restricting Senile Plaque Formation in Alzheimer's Disease." Neuron, 2006, 49(4): 489-502.
Slater, M. et al., "Endometriotic cells exhibit metaplastic change and oxidative DNA damage as well as decreased function, compared to normal endometrium." Journal of Molecular Histology, 2005, 36(4): 257-263.
Somia, N., Verma, I. M., "Reviews, Gene Therapy: Trials and Tribulations." Nature Reviews: Genetics, Nov. 2000, 1(2): 91-99.
Soo, E.T.L. et al., "Heat Shock Proteins as Novel Therapeutic Targets in Cancer." in vivo, 2008, 22(3): 311-315.
SP16H_Human, Accession No. Q9Y5B9, Jul. 2006.
Straino, S. et al., "High-Mobility Group Box 1 Protein in Human and Murine Skin: Involvement in Wound Healing." Journal of Investigative Dermatology, Jan. 2008, 128: 1545-1553.
Sun, S. et al., "Isolation of Mouse Marrow Mesenchymal Progenitors by a Novel and Reliable Method." Stem Cells, 2003, 21(5): 527-535.
Tagami, K. et al., "Elevation of serum high-mobility group box 1 protein during granulocyte colony-stimulating factorinduced peripheral blood stem cell mobilisation." British Journal of Haematology, 2006, 135(4): 567-569.
Tagliafico, E. et al., "TGFB/BMP activate the smooth muscle/bone differentiation programs in mesoangioblasts." Journal of Cell Science, Apr. 2004, 117(19): 4377-4388.
Takahashi, Kunihiko, et al., "Modulated Inflammation by Injection of High-Mobility Group Box 1 Recovers Post-Infarction Chronically Failing Heart." Circulation, Sep. 2008, 118(14 Suppl): S106-S114.
Takahashi, K. et al., "Effects of HMGB1 on PostInfarction Chronic Heart Failure—Novel Mechanism Regarding Therapeutic Effects of Cell Therapy." Supplement, 2011, 27 I-E-19:S189.
Takami, Y. et al., "Synergistic induction of hepatocyte growth factor in human skin fibroblasts by the inflammatory cytokines interleukin-1 and interferon-y." Biochemical and Biophysical Research Communications, 2005, 327: 212-217.
Takeishi, Yasuchika et al., "Importance of Inflammation and Immune Response in Heart Failure—Toll-Like Receptor-Mediated Signaling Pathway and Ventricular Remodeling After Myocardial Infarction." Journal of Clinical and Experimental Medicine, Jan. 30, 2010, 232(5):378-385.
Tamai, K. et al., U.S. Appl. No. 11/997,475, "Mesenchymal Stem Cell Inducer, Tissue Regeneration Promoter and Method of Preparing Mesenchymal Stem Cell." filed on Jan. 31, 2008.
Tamai et al., "Nihon Hiuka Gakkai Zasshi," Japanese Journal of Dermatology, 2008, 118(4): 645 (#EL28-4) (translated English abstract attached, titled "New Wave of Wound Healing").
Tamai, K. et al., "PDGFRα-positive cells in bone marrow are mobilized by high mobility group box 1 (HMGB1) to regenerate inured epithelia," Proceedings of the National Academy of Sciences, 2011, 108(16): 6609-6614.
Tamai, K. et al., "Development and Outlook of Internal Regeneration-Inducing Pharmaceuticals that use in vivo Bone Marrow Mesenchymal Stem / Progenitor Cell-Mobilizing Factors," Gene & Medicine MOOK, Jul. 22, 2012, pp. 207-212.
Tamai, K., "Development of Regeneration-Inducing Medicine Utilizing Molecular Mechanism for in vivo tissue Regeneration by Circulating Mesenchymal Stem Cells." BIO Clinica, 2016, 31(10): 1042-1046.
Tamai, K. et al., U.S. Appl. No. 17/517,967, "Agents for Promoting Tissue Regeneration by Recruiting Bone Marrow Mesenchymal Stem Cells and/or Pluripotent Stem Cells into Blood ." filed on Nov. 3, 2021.
Tamai, K. et al., U.S. Appl. No. 16/768,654, "Therapeutic Agent for Inflammatory Bowel Disease." filed May 30, 2020.
Tamilselvi, E., et al., "Association of Disease Severity with IL-1 Levels in Methotrexate-Treated Psoriasis Patients." Scandinavian Journal of Immunology, 2013, 78: 545-553.
Tang, L., Eaton, J. W., "Fibrin(ogen) Mediates Acute Inflammatory Responses to Biomaterials." J. Exp. Med., Dec. 1993, 178: 2147-2156.
Tang, D. et al., "High-Mobility Group Box 1, Oxidative Stress, and Disease." Antioxidants & Redox Signaling, 2011, 14(7): 1315-1335.
Tao, A., et al., "Cardiomyocyte-Fibroblast Interaction Contributes to Diabetic Cardiomyopathy in Mice: Role of HMGB1/TLR4/IL-33 Axis." Biochimica et Biophysica Acta, 2015, 1852: 2075-2085.
Tatsumi, R. et al., "HGF/SF Is Present in Normal Adult Skeletal Muscle and Is Capable of Activating Satellite Cells," Developmental Biology, 1998, 194: 114-128.
Alden, T. D., et al., "In Vivo Endochondral Bone Formation Using a Bone Morphogenetic Protein 2 Adenoviral Vector." Human Gene Therapy, Sep. 1999, 10(13): 2245-2253.
Andersson, U. et al., "HMGB1 as a DNA-binding cytokine." Journal of Leukocyte Biology, 2002, 72: 1084-1091.
Arminan, A. et al., "Mesenchymal Stem Cells Provide Better Results Than Hematopoietic Precursors for the Treatment of Myocardial Infarction." Journal of the American College of Cardiology, 2010, 55(20): 2244-2253.
Arnau, J. et al., "Current Strategies for the use of Affinity Tags and Tag Removal for the Purification of Recombinant Proteins." Protein Expression and Purification, 2006, 48: 1-13.
Asch, F.M., et al., "Lack of sensitivity of the electrocardiogram for detection of old myocardial infarction: A cardiac magnetic resonance imaging study." American Heart Journal, Oct. 2006, 152(4): 742-748.
Ball, S.G., et al., "Mesenchymal stem cells and neovascularization: role of platelet-derived growth factor receptors." J. Cell. Mo. Med., 2007, 11(5): 1012-1030.
Basso, D. M. et al., "Basso Mouse Scale for Locomotion Detects Differences in Recovery after Spinal Cord Injury in Five Common Mouse Strains." Journal of Neurotrauma, 2006, 23(5): 635-659.
Berry, M. F. et al., "Mesenchymal stem cell injection after myocardial infarction improves myocardial compliance." Am. J. Physiol. Heart Circ. Physiol., Jun. 2006, 290(6): H2196-H2203.
Bianchi, M. E., "High mobility group 1 protein (HMGB1) N-terminal peptide." Geneseq Accession No. ADO80180, Aug. 12, 2004.
Bianchi, M. E. et al., "The DNA binding site of HMG1 protein is composed of two similar segments (HMG boxes), both of which have counterparts in other eukaryotic regulatory proteins." The EMBO Journal, Mar. 1992, 11(3): 1055-1063.
Bittira, B. et al., "Mobilization and homing of bone marrow stromal cells in myocardial infarction." European Journal of Cardio-thoracic Surgery, 2003, 24(3): 393-398.
Blain, A.M., et al., "δ-Sarcoglycan-deficient muscular dystrophy: from discovery to therapeutic approaches." Skeletal Muscle, 2011, 1(13): 1-13.
Brunner, S., et al., "Erythropoientin Administration After Myocardial Infarction in Mice Attenuates Ischemic Cardiomyopathy Associated with Enhanced Homing of Bone Marrow-Derived Progenitor Cells Via the CXCR-4/SDF-1 Axis." The FASEB Journal, 2009, 23: 351-361.
"BTF3_Human", NCBI_TaxID=9606, Accession No. P20290, Feb. 1991.
Bustin, M., "Regulation of DNA-Dependent Activities by the Functional Motifs of the High-Mobility-Group Chromosomal Proteins." Mol. Cell. Biol., 1999, 19(8): 5237-5246.
Cairo, M. S. "Results of a Phase I/II Trial of Recombinant Human Granulocyte-Macrophage Colony-Stimulating Factor in Very Low Birthweight Neonates: Significant Induction of Circulatory Neutrophils, Monocytes, Platelets, and Bone Marrow Neutrophils." Blood, 1995, 86(7): 2509-2515.
"Cardiomegaly" Merriam Webster, 2015 archived page, accessed via Wayback Machine [online] [accessed at https://web.archive.org/web/20150107154504/https://www.merriam-webster.com/medical/cardiomegaly on May 21, 2020]. (Year: 2015).
"Cardiomyopathy: Symptoms, diagnosis and treatment." Harvard Health Publishing Harvard Medical School, Dec. 29, 2014.

(56) References Cited

OTHER PUBLICATIONS

Castro, R. F. et al., "Failure of Bone Marrow Cells to Transdifferentiate into Neural Cells in Vivo." Science, Aug. 2002, 297(5585): 1299.
Chamberlain, G. et al., "Concise Review: Mesenchymal Stem Cells: Their Phenotype, Differentiation Capacity, Immunological Features, and Potential for Homing." Stem Cells, 2007, 25: 2739-2749.
Chan, J. K., et al. "Alarmins: awaiting a clinical response." The Jounral of clinical investigation 122.8 (2012): 2711-2719.
Charoonpatrapong, K. et al., "HMGB1 Expression and Release by Bone Cells." Journal of Cellular Physiology, 2006, 207(2): 480-490.
Chen, X. et al., "Human Bone Marrow Stromal Cell Cultures Conditioned by Traumatic Brain Tissue Extracts: Growth Factor Production." Journal of Neuroscience Research, 2002, 69: 687-691.
Chen, Y. et al., "Coaxing bone marrow stromal mesenchymal stem cells towards neuronal differentiation: progress and uncertainties." Cellular and Molecular Life Sciences, 2006, 63(14): 1649-1657.
Chen, T., et al., "Involvement of high mobility group box-1 in imiquimod-induced psoriasis-like mice model." Journal of Dermatology, 2017, 44: 573-581.
Chopp, M., Li, Y., "Treatment of neural injury with marrow stromal cells." The Lancet Neurology, Jun. 2002, 1(2): 92-100.
Chou, D.K.H. et al., "Identity of nuclear high-mobility-group protein, HMG-1, and sulfoglucuronyl carbohydrate-binding protein, SBP-1, in brain." Journal of Neurochemistry, 2001, 77(1): 120-131.
Cole, J.S.III, "Pharmacologic Mobilization of Mesenchymal Stem Cells for Enhanced Bone Formation." Colby College, Rush University, 2009, Thesis, UMI No. 1466383, 1-82.
Degryse, B. et al., "The High Mobility Group (HMG) Boxes of the Nuclear Protein HMG1 Induce Chemotaxis and Cytoskeleton Reorganization in Rat Smooth Muscle Cells." The Journal of Cell Biology, Mar. 2001, 152(6): 1197-1206.
Delarosa, O., Lombardo, E., "Modulation of Adult Mesenchymal Stem Cells Activity by Toll-Like Receptors: Implications on Therapeutic Potential." Mediators of Inflammation, 2010 vol. 2010, Article ID: 865601, pp. 1-9.
Desai, N. P., Hubbell, J. A., "Tissue response to intraperitoneal implants of polyethylene oxide-modified polyethylene terephthalate." Biomaterials, 1992, 13(8): 505-510, Abstract only.
Desantis, S. et al., "TNFα Deficiency Results in Increased IL-1ß in an Early Onset of Spontaneous Murine Colitis." Cell Death and Disease, 2017, 8: e2993, pp. 1-7.
De Souza, A.W.S. et al., "HMGB1 in vascular diseases: its role in vascular inflammation and atherosclerosis." Autoimmunity Reviews, 2012, 11: 909-917.
Dong, Y. et al., "HMGB1 Protein Does Not Mediate the Inflammatory Response in Spontaneous Spinal Cord Regeneration." The Journal of Biological Chemistry, Jun. 11, 2013, 288(25): 18204-18218.
Eckert, R.L. et al., "S100 Proteins in the Epidermis." The Journal of Investigative Dermatology, 2004, 123(1): 23-33.
Ehrchen, J.M. et al., "The endogenous Toll-like receptor 4 agonist S100A8/S100A9 (calprotectin) as innate amplifier of infection, autoimmunity, and cancer." Journal of Leukocyte Biology, Sep. 2009, 86: 557-566.
Erlandsson, H. et al., "The nuclear protein HMGB1 as a proinflammatory mediator," European Journal of Immunology, 2004, 34(6): 1503-1512.
Esposito, E. et al., "Melatonin reduces stress-activated/mitogen-activated protein kinases in spinal cord injury." J. Pineal. Res., 2009, 46: 79-86.
Fang, P. et al., "HMGB1 Contributes to Regeneration After Spinal Cord Injury in Adult Zebrafish." Mol. Neurobio., 2014, 49: 472-483.
Forte, G. et al., "Hepatocyte Growth Factor Effects on Mesenchymal Stem Cells: Proliferation, Migration, and Differentiation." Stem Cells, 2006, 24: 23-33.
Frankel, A.E., et al., "Characterization of Diphtheria Fusion Proteins Targeted to the Human Interleukin-3 Receptor." Protein Engineering, 2000, 13(8): 575-581.
Fritsch, A., et al., "A Hypomorphic Mouse Model of Dystrophic Epidermolysis Bullosa Reveals Mechanisms of Disease and Response to Fibroblast Therapy." The Journal of Clinical Investigation, May 2008, 118(5): 1669-1679.
Fujii, M. et al., "Roles of Bone Morphogenetic Protein Type I Receptors and Smad Proteins in Osteoblast and Chondroblast Differentiation." Molecular Biology of the Cell, Nov. 1999, 10(11): 3801-3813.
Fukushima, N., et al., "Registry Report on Heart Transplantation in Japan (Jun. 2016)." Circulation Journal, 2017, 81: 298-303.
Gallina, C., et al., "A New Paradigm in Cardiac Regeneration: The Mesenchymal Stem Cell Secretome." Stem Cells International, 2015, vol. 2015, Article ID 765846, pp. 1-10.
Germani, A. et al., "Pivotal Advance: High-mobility group box 1 protein-a cytokine with a role in cardiac repair," Journal of Leukocyte Biology, Jan. 2007, 81(1): 41-45.
Gong, W. et al., "The Anti-Inflammatory Activity of HMGB1 A Box is Enhanced When Fused with C-Terminal Acidic Tail," Journal of Biomedicine and Biotechnology, 2010, vol. 2010, Article ID 915234, pp. 1-6.
Goto, et al., "Investigation of the application of myocardial regeneration inducing therapy using HMGB1 to cardiac infarction." Regenerative Medicine, Feb. 1, 2017, 16: 289.
Granero-Molto, F. et al., "Role of mesenchymal stem cells in regenerative medicine: application to bone and cartilage repair," Expert Opinion on Biological Therapy, 2008, 8(3): 255-268.
Gudjonsson, J. et al., "Chapter 18—Psoriasis." Fitzpatrick's Dermatology in General Medicine, 8th edition, New York: Mc-Graw Hill Medical, 2012, pp. 197-217.
ICH GCP, US Clinical Trials Registry, Clinical Trial NCT01287897, A Study to Assess the Efficacy and Safety of PF-04236921 in Subjects with Crohn's Disease who Failed Anti-TNF Therapy (ANDANTE), <<accessed from the Internet Dec. 1, 2023, https://ichgcp.net/clinical-trials-registry/NCT01287897>>.
Danese, S., et al., "Randomised trial and open-label extension study of an anti-interleukin-6 antibody in Crohn's disease (Andante I and II)." Gut, 2019, 68(1): 40-48.
Ito, H., et al., "A Pilot Randomized Trial of a Human Anti-Interleukin-6 Receptor Monoclonal Antibody in Active Crohn's Disease." Gastroenterology, 2004, 126(4): 989-996.
Ko, E., et al., "SERPINA3 is a key modulator of HNRNP-K transcriptional activity against oxidative stress in HCC." Redox Biology, 2019, 24(101217): 1-10.
Nam, Y.-S., et al., "Negative impact of bone-marrow-derived mesenchymal stem cells on dextran sulfate sodium-induced colitis." World Journal of Gastroenterology, 2015, 21(7): 2030-2039.
Shirley, D., et al., "Systemic recruitment of osteoblastic cells in fracture healing." Journal of Orthopaedic Research, 2005, 23: 1013-1021.
Six, I., et al., "Beneficial effect of pharmacological mobilization of bone marrow in experimental cerebral ischemia." European Journal of Pharmacology, 2003, 458: 327-328.
Sommer, J., et al., "Interleukin-6, but not the interleukin-6 receptor plays a role in recovery from dextran sodium sulfate-induced colitis." International Journal of Molecular Medicine, 2014, 34(3): 651-660.
Nishimura, Y.I., et al., "No. 9 Establishment of canine liver fibrosis model and evaluation of the efficacy of cultured autologous bone marrow-derived mesenchymal stem cell infusion." Yamaguchi Medical Journal, 2016, 65(4) p. 196, Only the part in English.
Aikawa, E., et al., "Systemic high-mobility group box 1 administration suppresses skin inflammation by inducing an accumulation of PDGFRα+ mesenchymal cells from bone marrow." Scientific Reports, 2015, 5(11008), pp. 1-14.
Britannica, The Editors of Encyclopaedia. "peptide". Encyclopedia Britannica, Sep. 9, 2024, https://www.britannica.com/science/peptide. Accessed Sep. 18, 2024.
Tamai, K., "Declaration of Katsuto Tamai, M.D., Ph.D. Under 37 C.F.R. §1.132." Sep. 7, 2022, pp. 1-13, submitted Sep. 16, 2022 in U.S. Appl. No. 16/499,604.
Kawada, H., et al., "Nonhematopoietic mesenchymal stem cells can be mobilized and differentiate into cardiomyocytes after myocardial infarction." Blood, Dec. 2004, 104(12): 3581-3587.

(56) References Cited

OTHER PUBLICATIONS

Ukai, R., et al., "Mesenchymal Stem Cells Derived from Peripheral Blood Protects against Ischemia." Journal of Neurotrauma, 2007, 24(3): 508-520.

Dieleman, L.A., et al., "Dextran Sulfate Sodium-Induced Colitis Occurs in Severe Combined Immunodeficient Mice." Gastroenterology, 1994, 107(6): 1643-1652.

Silva, I., et al., "Preclinical Study in Vivo for New Pharmacological Approaches in Inflammatory Bowel Disease: A Systematic Review of Chronic Model of TNBS-Induced Colitis." Journal of Clinical Medicine, 2019, 8(10), 1574, pp. 1-20.

Andersson, U., et al., "The role of HMGB1 in the pathogenesis of rheumatic disease." Biochimica et Biophysica Acta, 2010, 1799: 141-148.

Štros, M., "HMGB proteins: Interactions with DNA and chromatin." Biochimica et Biophysica Acta, 2010, 1799: 101-113.

\* cited by examiner

DISEASE TREATMENT DRUG BASED ON MESENCHYMAL-STEM-CELL MOBILIZATION

CROSS REFERENCE TO A RELATED APPLICATION

This application is a National Stage Application of International Application Number PCT/JP2019/039231, filed Oct. 4, 2019; which claims priority to Japanese Application No. 2018-190089, filed Oct. 5, 2018.

The Sequence Listing for this application is labeled "SeqList-25Mar21-ST25.txt", which was created on Mar. 25, 2021, and is 177 KB. The entire content is incorporated herein by reference in its entirety.

TECHNICAL FIELD

The present application relates to compositions for mobilizing mesenchymal stem cells and agents for treating diseases based on the mobilization of mesenchymal stem cells.

BACKGROUND ART

Mesenchymal stem cells contained in bone marrow fluid and the like have the ability to differentiate into various tissues (pluripotency) such as bone, cartilage, fat, muscle, nerve, and epithelium. In recent years, attempts have been widely made to perform regenerative medicine (cell transplantation therapy) using bone marrow-derived mesenchymal stem cells proliferated by culture. However, collection of bone marrow blood containing mesenchymal stem cells is done with an invasive technique which inserts a thick needle into the iliac bone repeatedly, thereby placing a large burden on the donor. In addition, mesenchymal stem cells gradually lose their proliferative ability and pluripotency when subcultured continuously in vitro. Furthermore, culturing mesenchymal stem cells based on high quality control that guarantees the safety of in vivo transplantation requires special culture equipment such as CPC (cell processing center), so the current situation is that it can be carried out only at a limited number of universities and companies.

CITATION LIST

Non-Patent Literature

[NPL 1] PNAS 2011 Apr. 19; 108 (16): 6609-14

PATENT LITERATURE

[PTL 1] WO2008/053892
[PTL 2] WO2009/133939
[PTL 3] WO2012/147470

SUMMARY OF INVENTION

Technical Problem

An objective of the present application is to develop a new regenerative medicine technology that can overcome the problems of cell transplantation therapy.

Solution to Problem

The present inventors identified a large number of nucleoproteins contained in an extract of skin tissue by mass spectrometry, randomly selected a plurality of partial amino acid sequences of the identified nucleoproteins, and chemically synthesized peptides consisting of the partial amino acid sequences. Then, their activity of mobilizing mesenchymal stem cells was examined. As a result, it was found that these peptides show an activity of mobilizing mesenchymal stem cells into peripheral blood, even though their amino acid sequences are completely different from each other. It was also found that fragment peptides of the nucleoproteins have therapeutic effects on diseases characterized by inflammation and abnormalities of the immune system (e.g., inflammatory bowel disease and psoriasis). Based on these findings, a new regenerative medicine technology to overcome the problems of cell transplantation therapy is provided.

Specifically, the present application provides the following:

[1]
A composition for use in mobilizing mesenchymal stem cells to peripheral blood, which comprises a nuclear protein or a fragment peptide thereof.

[2]
A composition for use in treatment of a disease or pathological condition in a subject by mobilizing mesenchymal stem cells to peripheral blood, which comprises a nuclear protein or a fragment peptide thereof.

[3]
The composition of [2], wherein the treatment of a disease or pathological condition is selected from inflammation-suppressing therapy, immunomodulatory therapy, tissue regeneration-inducing therapy, and tissue fibrosis-suppressing therapy.

[4]
The composition of [2], wherein the disease or pathological condition is selected from an inflammatory disease, an autoimmune disease, a disease accompanied by tissue damage, ischemia, or necrosis, and a fibrotic disease.

[5]
The composition of [2], wherein the disease or pathological condition is selected from inflammatory bowel disease and psoriasis.

[6]
A composition for use in treatment of a disease selected from inflammatory bowel disease and psoriasis, which comprises a nuclear protein or a fragment peptide thereof.

[7]
The composition of any one of [1] to [6], wherein the nuclear protein or fragment peptide thereof comprises a nuclear localization signal.

[8]
The composition of any one of [1] to [7], wherein the nuclear protein or fragment peptide thereof is a nuclear protein involved in transcription regulation or a fragment peptide thereof.

[9]
The composition of any one of [1] to [8], wherein the nuclear protein or fragment peptide thereof is a nuclear protein selected from the following or a fragment peptide thereof:
(1) BTF3 protein;
(2) SUPT16H protein;
(3) YBX1 protein;
(4) NPM1 protein;
(5) PA2G4 protein;
(6) PFDN5 protein;
(7) PSMC3 protein;
(8) HNRNPK protein; and (9) a nuclear protein functionally equivalent to a protein selected from (1) to (8).

[10]

The composition of any one of [1] to [9], wherein the nuclear protein or fragment peptide thereof is a nuclear protein selected from the following or a fragment peptide thereof:
(a) a nuclear protein comprising an amino acid sequence selected from SEQ ID NOs: 1 to 34;
(b) a nuclear protein comprising an amino acid sequence resulting from substitution, deletion, insertion, or addition of one or more amino acids in an amino acid sequence selected from SEQ ID NOs: 1 to 34; and
(c) a nuclear protein comprising an amino acid sequence with a sequence identity of about 80% or higher with an amino acid sequence selected from SEQ ID NOs: 1 to 34.

[11]

The composition of any one of [1] to [10], wherein the fragment peptide of the nuclear protein is a fragment peptide selected from the following:
(a) a nuclear protein fragment peptide consisting of a portion of an amino acid sequence selected from SEQ ID NOs: 1 to 34;
(b) a nuclear protein fragment peptide comprising an amino acid sequence selected from SEQ ID NOs: 35 to 56;
(c) a nuclear protein fragment peptide consisting of a portion of an amino acid sequence selected from SEQ ID NOs: 35 to 56;
(d) a nuclear protein fragment peptide comprising an amino acid sequence resulting from substitution, deletion, insertion, or addition of one or more amino acids in an amino acid sequence selected from SEQ ID NOs: 35 to 56; and
(e) a nuclear protein fragment peptide comprising an amino acid sequence with a sequence identity of about 80% or higher with an amino acid sequence selected from SEQ ID NOs: 35 to 56.

[12]

A fragment peptide of a nuclear protein selected from the following:
(1) BTF3 protein;
(2) SUPT16H protein;
(3) YBX1 protein;
(4) NPM1 protein;
(5) PA2G4 protein;
(6) PFDN5 protein;
(7) PSMC3 protein;
(8) HNRNPK protein; and
(9) a nuclear protein functionally equivalent to a protein selected from (1) to (8).

[13]

The fragment peptide of [12], comprising a nuclear localization signal.

[14]

The fragment peptide of [12] or [13], which is a fragment peptide of a nuclear protein selected from the following:
(a) a nuclear protein comprising an amino acid sequence selected from SEQ ID NOs: 1 to 34;
(b) a nuclear protein comprising an amino acid sequence resulting from substitution, deletion, insertion, or addition of one or more amino acids in an amino acid sequence selected from SEQ ID NOs: 1 to 34; and
(c) a nuclear protein comprising an amino acid sequence with a sequence identity of about 80% or higher with an amino acid sequence selected from SEQ ID NOs: 1 to 34.

[15]

The fragment peptide of any one of [12] to [14], which is selected from the following:
(a) a nuclear protein fragment peptide consisting of a portion of an amino acid sequence selected from SEQ ID NOs: 1 to 34;
(b) a nuclear protein fragment peptide comprising an amino acid sequence selected from SEQ ID NOs: 35 to 56;
(c) a nuclear protein fragment peptide consisting of a portion of an amino acid sequence selected from SEQ ID NOs: 35 to 56;
(d) a nuclear protein fragment peptide comprising an amino acid sequence resulting from substitution, deletion, insertion, or addition of one or more amino acids in an amino acid sequence selected from SEQ ID NOs: 35 to 56; and
(e) a nuclear protein fragment peptide comprising an amino acid sequence with a sequence identity of about 80% or higher with an amino acid sequence selected from SEQ ID NOs: 35 to 56.

[A1]

A method for mobilizing mesenchymal stem cells to peripheral blood, comprising administering to a subject an effective amount of a nuclear protein or a fragment peptide thereof.

[A2]

A method for treating a disease or pathological condition in a subject by mobilizing mesenchymal stem cells to peripheral blood, which comprises administering to the subject an effective amount of a nuclear protein or a fragment peptide thereof.

[A3]

The method of [A2], wherein the treatment of a disease or pathological condition is selected from inflammation-suppressing therapy, immunomodulatory therapy, tissue regeneration-inducing therapy, and tissue fibrosis-suppressing therapy.

[A4]

The method of [A2], wherein the disease or pathological condition is selected from an inflammatory disease, an autoimmune disease, a disease accompanied by tissue damage, ischemia, or necrosis, and a fibrotic disease.

[A5]

The method of [A2], wherein the disease or pathological condition is selected from inflammatory bowel disease and psoriasis.

[A6]

A method for treating a disease selected from inflammatory bowel disease or psoriasis in a subject, which comprises administering to the subject an effective amount of a nuclear protein or a fragment peptide thereof.

[A7]

The method of any one of [A1] to [A6], wherein the nuclear protein or fragment peptide thereof comprises a nuclear localization signal.

[A8]

The method of any one of [A1] to [A7], wherein the nuclear protein or fragment peptide thereof is a nuclear protein involved in transcription regulation or a fragment peptide thereof.

[A9]

The method of any one of [A1] to [A8], wherein the nuclear protein or fragment peptide thereof is a nuclear protein selected from the following or a fragment peptide thereof:
- (1) BTF3 protein;
- (2) SUPT16H protein;
- (3) YBX1 protein;
- (4) NPM1 protein;
- (5) PA2G4 protein;
- (6) PFDN5 protein;
- (7) PSMC3 protein;
- (8) HNRNPK protein; and
- (9) a nuclear protein functionally equivalent to a protein selected from (1) to (8).

[A10]

The method of any one of [A1] to [A9], wherein the nuclear protein or fragment peptide thereof is a nuclear protein selected from the following or a fragment peptide thereof:
- (a) a nuclear protein comprising an amino acid sequence selected from SEQ ID NOs: 1 to 34;
- (b) a nuclear protein comprising an amino acid sequence resulting from substitution, deletion, insertion, or addition of one or more amino acids in an amino acid sequence selected from SEQ ID NOs: 1 to 34; and
- (c) a nuclear protein comprising an amino acid sequence with a sequence identity of about 80% or higher with an amino acid sequence selected from SEQ ID NOs: 1 to 34.

[A11]

The method of any one of [A1] to [A10], wherein the fragment peptide of the nuclear protein is a fragment peptide selected from the following:
- (a) a nuclear protein fragment peptide consisting of a portion of an amino acid sequence selected from SEQ ID NOs: 1 to 34;
- (b) a nuclear protein fragment peptide comprising an amino acid sequence selected from SEQ ID NOs: 35 to 56;
- (c) a nuclear protein fragment peptide consisting of a portion of an amino acid sequence selected from SEQ ID NOs: 35 to 56;
- (d) a nuclear protein fragment peptide comprising an amino acid sequence resulting from substitution, deletion, insertion, or addition of one or more amino acids in an amino acid sequence selected from SEQ ID NOs: 35 to 56; and
- (e) a nuclear protein fragment peptide comprising an amino acid sequence with a sequence identity of about 80% or higher with an amino acid sequence selected from SEQ ID NOs: 35 to 56.

[B1]

A nuclear protein or a fragment peptide thereof for use in mobilizing mesenchymal stem cells to peripheral blood.

[B2]

A nuclear protein or a fragment peptide thereof for use in treatment of a disease or pathological condition in a subject by mobilizing mesenchymal stem cells to peripheral blood.

[B3]

The nuclear protein or fragment peptide thereof of [B2], wherein the treatment of a disease or pathological condition is selected from inflammation-suppressing therapy, immunomodulatory therapy, tissue regeneration-inducing therapy, and tissue fibrosis-suppressing therapy.

[B4]

The nuclear protein or fragment peptide thereof of [B2], wherein the disease or pathological condition is selected from an inflammatory disease, an autoimmune disease, a disease accompanied by tissue damage, ischemia, or necrosis, and a fibrotic disease.

[B5]

The nuclear protein or fragment peptide thereof of [B2], wherein the disease or pathological condition is selected from inflammatory bowel disease and psoriasis.

[B6]

A nuclear protein or a fragment peptide thereof for use in treatment of a disease selected from inflammatory bowel disease and psoriasis.

[B7]

The nuclear protein or fragment peptide thereof of any one of [B1] to [B6], which comprises a nuclear localization signal.

[B8]

The nuclear protein or fragment peptide thereof of any one of [B1] to [B7], which is a nuclear protein involved in transcription regulation or a fragment peptide thereof.

[B9]

The nuclear protein or fragment peptide thereof of any one of [B1] to [B8], which is selected from the following:
- (1) BTF3 protein;
- (2) SUPT16H protein;
- (3) YBX1 protein;
- (4) NPM1 protein;
- (5) PA2G4 protein;
- (6) PFDN5 protein;
- (7) PSMC3 protein;
- (8) HNRNPK protein; and
- (9) a nuclear protein functionally equivalent to a protein selected from (1) to (8).

[B10]

The nuclear protein or fragment peptide thereof of any one of [B1] to [B9], which is selected from the following:
- (a) a nuclear protein comprising an amino acid sequence selected from SEQ ID NOs: 1 to 34;
- (b) a nuclear protein comprising an amino acid sequence resulting from substitution, deletion, insertion, or addition of one or more amino acids in an amino acid sequence selected from SEQ ID NOs: 1 to 34; and
- (c) a nuclear protein comprising an amino acid sequence with a sequence identity of about 80% or higher with an amino acid sequence selected from SEQ ID NOs: 1 to 34.

[B11]

The nuclear protein or fragment peptide thereof of any one of [B1] to [B10], which is selected from the following:
- (a) a nuclear protein fragment peptide consisting of a portion of an amino acid sequence selected from SEQ ID NOs: 1 to 34;
- (b) a nuclear protein fragment peptide comprising an amino acid sequence selected from SEQ ID NOs: 35 to 56;
- (c) a nuclear protein fragment peptide consisting of a portion of an amino acid sequence selected from SEQ ID NOs: 35 to 56;
- (d) a nuclear protein fragment peptide comprising an amino acid sequence resulting from substitution, deletion, insertion, or addition of one or more amino acids in an amino acid sequence selected from SEQ ID NOs: 35 to 56; and
- (e) a nuclear protein fragment peptide comprising an amino acid sequence with a sequence identity of about 80% or higher with an amino acid sequence selected from SEQ ID NOs: 35 to 56.

[C1]

Use of a nuclear protein or a fragment peptide thereof in manufacture of a medicament or reagent for mobilizing mesenchymal stem cells to peripheral blood.

[C2]

Use of a nuclear protein or a fragment peptide thereof in manufacture of a medicament for treating a disease or pathological condition in a subject by mobilizing mesenchymal stem cells to peripheral blood.

[C3]

The use of [C2], wherein the treatment of a disease or pathological condition is selected from inflammation-suppressing therapy, immunomodulatory therapy, tissue regeneration-inducing therapy, and tissue fibrosis-suppressing therapy.

[C4]

The use of [C2], wherein the disease or pathological condition is selected from an inflammatory disease, an autoimmune disease, a disease accompanied by tissue damage, ischemia, or necrosis, and a fibrotic disease.

[C5]

The use of [C2], wherein the disease or pathological condition is selected from inflammatory bowel disease and psoriasis.

[C6]

Use of a nuclear protein or a fragment peptide thereof in manufacture of a medicament for treating a disease selected from inflammatory bowel disease and psoriasis.

[C7]

The use of any one of [C1] to [C6], wherein the nuclear protein or fragment peptide thereof comprises a nuclear localization signal.

[C8]

The use of any one of [C1] to [C7], wherein the nuclear protein or fragment peptide thereof is a nuclear protein involved in transcription regulation or a fragment peptide thereof.

[C9]

The use of any one of [C1] to [C8], wherein the nuclear protein or fragment peptide thereof is a nuclear protein selected from the following or a fragment peptide thereof:
 (1) BTF3 protein;
 (2) SUPT16H protein;
 (3) YBX1 protein;
 (4) NPM1 protein;
 (5) PA2G4 protein;
 (6) PFDN5 protein;
 (7) PSMC3 protein;
 (8) HNRNPK protein; and
 (9) a nuclear protein functionally equivalent to a protein selected from (1) to (8).

[C10]

The use of any one of [C1] to [C9], wherein the nuclear protein or fragment peptide thereof is a nuclear protein selected from the following or a fragment peptide thereof:
 (a) a nuclear protein comprising an amino acid sequence selected from SEQ ID NOs: 1 to 34;
 (b) a nuclear protein comprising an amino acid sequence resulting from substitution, deletion, insertion, or addition of one or more amino acids in an amino acid sequence selected from SEQ ID NOs: 1 to 34; and
 (c) a nuclear protein comprising an amino acid sequence with a sequence identity of about 80% or higher with an amino acid sequence selected from SEQ ID NOs: 1 to 34.

[C11]

The use of any one of [C1] to [C10], wherein the fragment peptide of the nuclear protein is a fragment peptide selected from the following:
 (a) a nuclear protein fragment peptide consisting of a portion of an amino acid sequence selected from SEQ ID NOs: 1 to 34;
 (b) a nuclear protein fragment peptide comprising an amino acid sequence selected from SEQ ID NOs: 35 to 56;
 (c) a nuclear protein fragment peptide consisting of a portion of an amino acid sequence selected from SEQ ID NOs: 35 to 56;
 (d) a nuclear protein fragment peptide comprising an amino acid sequence resulting from substitution, deletion, insertion, or addition of one or more amino acids in an amino acid sequence selected from SEQ ID NOs: 35 to 56; and
 (e) a nuclear protein fragment peptide comprising an amino acid sequence with a sequence identity of about 80% or higher with an amino acid sequence selected from SEQ ID NOs: 35 to 56.

DESCRIPTION OF EMBODIMENTS

Figure 1:
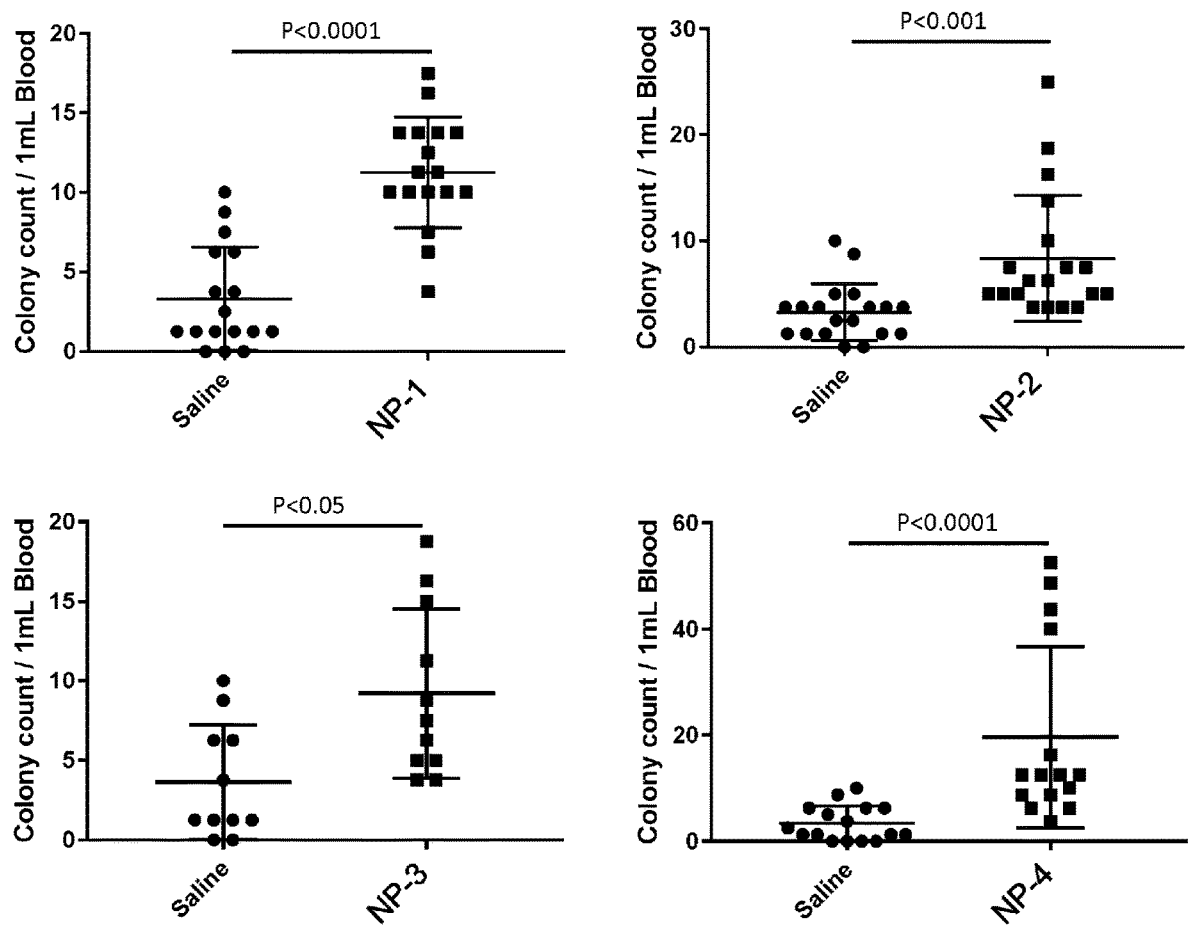
FIG. 1 is a plot of the number of colonies obtained by culturing peripheral blood 14 hours after administration of saline or the peptides. The number of colonies is shown as a value converted per 1 mL of collected peripheral blood. The long horizontal bar represents the mean value, and the short horizontal bars represent the standard deviation.

The present inventors previously found a substance having an activity of activating stem cells in a living body or mobilizing them to an injured tissue via peripheral circulation, and believe that the substance is promising as a new type of medicine that can overcome the weaknesses of cell therapy. Specifically, the present inventors have found that High Mobility Group Box 1 (HMGB1), which is a nuclear protein released from necrotic tissue, mobilizes cells that are positive for platelet-derived growth factor receptor α (PDGFRα), which play a role in inducing tissue regeneration in vivo (believed to be mesenchymal stem cells (MSC)), to a necrotic tissue through peripheral circulation, thereby suppresses inflammation of the necrotic tissue and promotes tissue regeneration. Further, the present inventors have also found that fragment peptides of HMGB1 exhibit an activity of mobilizing mesenchymal stem cells into peripheral blood and a tissue regeneration-inducing activity. Therefore, the activities shown by the HMGB1 fragment peptides do not appear to depend on three-dimensional structure.

HMGB1 is physiologically absent in the blood and is released into the blood by necrotic cells only when necrotic damage occurs. This suggests that mesenchymal stem cells recognize the presence of necrotic tissue in vivo by the exposure to HMGB1 or a fragment thereof, and are then mobilized into peripheral blood to suppress inflammation of the necrotic tissue and promote regeneration.

Here, the present inventors considered that nuclear proteins other than HMGB1 would also be released into the blood by necrotic damage proteins, and that nuclear proteins other than HMGB1 or fragments thereof may have similar mesenchymal stem cell-mobilizing activity as the HMGB1 protein or fragment peptides thereof. That is, the inventors considered that it would be possible to provide the theory that "mesenchymal stem cells recognize nuclear proteins or fragment peptides thereof that are not physiologically present in the blood and are mobilized to the blood".

To prove this theory, the present inventors identified many nuclear proteins contained in skin tissue extracts by mass spectrometry, randomly selected multiple partial amino acid sequences of the nuclear proteins identified, chemically synthesized peptides consisting of the partial amino acid sequences, and examined them for the mesenchymal stem cell-mobilizing activity. As a result, the above theory was confirmed to be correct, as these multiple peptides showed activities to mobilize mesenchymal stem cells into peripheral blood even though their amino acid sequences were completely different from each other.

Further, the present inventors found that fragment peptides of the above-mentioned nuclear proteins show therapeutic effects against diseases characterized by inflammation and abnormalities of the immune system (such as inflammatory bowel disease and psoriasis). Specifically, it was confirmed that the fragment peptides of nuclear proteins suppress weight loss in a mouse model of inflammatory bowel disease and suppress skin thickening in a psoriasis model.

It is well known to those skilled in the art that mesenchymal stem cells exert anti-inflammatory, immunomodulatory, and antifibrotic effects. Further, it is also well known to those skilled in the art that mesenchymal stem cells can exert a regeneration-promoting action on damaged tissues, as they have multipotency in that they can differentiate into various tissues. Therefore, by administering to a subject a nuclear protein or a fragment peptide thereof that has an activity of mobilizing mesenchymal stem cells to peripheral blood, the mesenchymal stem cells are recruited into the peripheral blood, and therapeutic effects for various diseases may be provided by the mesenchymal stem cells' anti-inflammatory action, immunomodulatory action, anti-fibrotic action, and tissue regeneration-promoting action (due to the differentiation and/or anti-inflammatory action of mesenchymal stem cells).

The present application provides compositions containing a nuclear protein or a fragment peptide thereof for use in mobilizing mesenchymal stem cells into peripheral blood.

The compositions for use in mobilizing mesenchymal stem cells into the peripheral blood of the present application can be used as a pharmaceutical composition or a reagent composition. In the present application, the term "pharmaceutical composition" is used interchangeably with "medicament", "drug" or "pharmacological composition", and the term "reagent composition" is used interchangeably with "reagent".

The compositions for use in mobilizing mesenchymal stem cells into peripheral blood of the present application can be used for treating a disease or pathological condition in a subject, for example, by mobilizing mesenchymal stem cells into peripheral blood.

Mesenchymal stem cells mobilized into peripheral blood using the composition for mobilizing mesenchymal stem cells into the peripheral blood of the present application can also be collected from the body, concentrated, and then used for treatment of a disease or pathological condition in a subject. The present application also provides use of a nuclear protein or a fragment thereof in the manufacture of a medicament or a reagent for collecting mesenchymal stem cells from the body.

The compositions for use in mobilizing mesenchymal stem cells into the peripheral blood of the present application can also be used in, for example, basic research, clinical research and such. Basic research and clinical research include, but are not limited to, mesenchymal stem cell mobilization research in vitro and mesenchymal stem cell mobilization research in laboratory animals. The present application also provides use of nuclear proteins or fragment peptides thereof in the manufacture of pharmaceuticals or reagents for basic or clinical research.

The compositions for use in mobilizing mesenchymal stem cells into peripheral blood can comprise one or more nuclear proteins, one or more fragment peptides, or a combination thereof.

In the present application, "mesenchymal stem cells" are cells that are collected from bone marrow or other tissues (blood such as umbilical cord blood, and skin, fat, pulp, etc.), can be cultured and proliferated on culture dishes (plastic or glass) as adherent cells, and have the ability to differentiate into mesenchymal tissues such as bone, cartilage, fat, and muscle. In one embodiment, mesenchymal stem cells also have the ability to differentiate into epithelial tissues and nerve tissues. In one embodiment, mesenchymal stem cells are cells capable of forming colonies. In the present application, mesenchymal stem cells may exist as a heterogeneous cell population comprising not only stem cells in the narrow sense (cells having self-renewal ability and differentiation ability) but also progenitor cells. Under culture conditions, the mesenchymal stem cells may include stem cells in the narrow sense, or may even include differentiated cells in addition to stem cells in the narrow sense and progenitor cells. In one embodiment, the mesenchymal stem cells may be composed only of stem cells in the narrow sense.

In the present application, progenitor cells are defined as cells with a unidirectional ability to differentiate into cells of specific tissues other than the blood system, and include cells that have the ability to differentiate into mesenchymal tissues, epithelial tissues, nerve tissues, parenchymatous organs, vascular endothelium.

In the present application, the mesenchymal stem cells include, but are not limited to, bone marrow mesenchymal stem cells and bone marrow-derived mesenchymal stem cells. The "bone marrow mesenchymal stem cells" exist in the bone marrow, and may be harvested from bone marrow and cultured and proliferated as adherent cells on culture dish (made of plastic or glass); and they are cells characterized in having the ability to differentiate into mesenchymal tissues such as bone, cartilage, fat, muscle and such. In one embodiment, bone marrow mesenchymal stem cells also have the ability to differentiate into epithelial tissues and nerve tissues. In one embodiment, bone marrow mesenchymal stem cells are cells capable of forming colonies. In the present application, the term "bone marrow mesenchymal stem cell" is used interchangeably with "bone marrow mesenchymal stromal cell", "bone marrow pluripotent stem cell" or "bone marrow pluripotent stromal cell".

"Bone marrow-derived mesenchymal stem cells" refers to bone marrow mesenchymal stem cells that have been mobilized from bone marrow to the outside of the bone marrow, and are cells that can be collected by peripheral blood collection, and further from mesenchymal tissues such as fat, epithelial tissues such as skin, or nerve tissues such as the brain. In the present application, the term "bone marrow-derived mesenchymal stem cell" can be used interchangeably with "bone marrow-derived mesenchymal stromal cell", "bone marrow-derived pluripotent stem cell" or "bone marrow-derived pluripotent stromal cell".

In one embodiment, bone marrow mesenchymal stem cells and bone marrow-derived mesenchymal stem cells are also characterized in that, by being administered to an injured part of a living body directly after collection or after once attached to a culture dish, the cells are also capable of differentiating into, for example, epithelial tissues such as skin-constituting keratinocytes or tissues of the nerve system which constitutes the brain.

Bone marrow mesenchymal stem cells and bone marrow-derived mesenchymal stem cells preferably have the ability to differentiate into osteoblast cells (identifiable by calcium deposition observed when differentiation is induced), cartilage cells (identifiable by being Alcian blue staining-positive, safranin-O staining-positive, or such), and fat cells (identifiable by being Sudan III staining-positive or such), and also differentiate into, for example, mesenchymal cells such as fibroblasts, smooth muscle cells, skeletal muscle cells, stromal cells, and tendon cells, nerve cells, pigment cells, epidermal cells, hair follicle cells (expressing cytokeratin family, hair keratin family or such), epithelial cells (for example, epithelial keratinized cells and intestinal epithelial cells express cytokeratin family or such), endothelial cells, and further differentiate into cells of parenchymal organs such as liver, kidney and pancreas, but the differentiated cells are not limited to the above cells.

Human mesenchymal stem cell markers can be exemplified by some or all of PDGFRα positive, PDGFRβ positive, Lin negative, CD45 negative, CD44 positive, CD90 positive, CD29 positive, Flk-1 negative, CD105 positive, CD73 positive, CD90 positive, CD71 positive, Stro-1 positive, CD106 positive, CD166 positive, CD31 negative, CD271 positive, and CD11b negative, but are not limited thereto.

Murine mesenchymal stem cell markers can be exemplified by some or all of CD44 positive, PDGFRα positive, PDGFRβ positive, CD45 negative, Lin negative, Sca-1 positive, c-kit negative, CD90 positive, CD105 positive, CD29 positive, Flk-1 negative, CD271 positive, and CD11b negative, but are not limited thereto.

Rat mesenchymal stem cell markers can be exemplified by some or all of PDGFRα positive, CD44 positive, CD54 positive, CD73 positive, CD90 positive, CD105 positive, CD29 positive, CD271 positive, CD31 negative, and CD45 negative, but are not limited thereto.

In the present application, examples of mesenchymal stem cells include PDGFRα-positive mesenchymal stem cells, PDGFRα-positive bone marrow-derived mesenchymal stem cells, and PDGFRα-positive bone marrow-derived cells obtained as adherent cells by cell culture of a mononuclear cell fraction in blood obtained by bone marrow harvest (bone marrow cell collection) or peripheral blood collection, but they are not limited thereto. Examples of PDGFRα-positive mesenchymal stem cells include PDGFRα- and CD44-positive cells, PDGFRα- and CD90-positive cells, PDGFRα- and CD105-positive cells, PDGFRα- and CD29-positive cells, and such. In one embodiment, PDGFRα-positive mesenchymal stem cells may be CD44-negative cells.

The present application provides compositions for use in the treatment of a disease or a pathological condition in a subject by mobilizing mesenchymal stem cells into the peripheral blood, comprising a nuclear protein or a fragment peptide thereof.

The compositions for use in the treatment of a disease or a pathological condition in a subject by mobilizing mesenchymal stem cells into the peripheral blood in the present application can be used as pharmaceutical compositions.

The subject in the present application is not particularly limited, and examples thereof include mammals, birds, and fish. Mammals include human and non-human animals, for example, human, mouse, rat, monkey, pig, dog, rabbit, hamster, guinea pig, horse, sheep, and whale, but are not limited thereto. In the present application, the term "subject" is used interchangeably with "patient", "individual", or "animal".

The composition for use in the treatment of a disease or pathological condition in a subject by mobilization of mesenchymal stem cells into the peripheral blood in the present application can comprise one or more nuclear proteins, one or more fragment peptides, or combinations thereof.

In the present application, the treatment of a disease or pathological condition is selected from, for example, inflammation-suppressing therapy, immunomodulatory therapy, tissue regeneration-inducing therapy, and tissue fibrosis-suppressing therapy, but is not limited thereto.

In the present application, the disease or pathological condition is selected from inflammatory diseases, autoimmune diseases, diseases accompanied by tissue damage, ischemia, or necrosis, and fibrotic diseases, but is not limited thereto.

In the present application, the inflammatory disease or autoimmune disease is, for example, selected from inflammatory bowel disease and psoriasis, but is not limited thereto. The fibrotic disease is selected from, for example, lung fibrosis, liver fibrosis, and liver cirrhosis, but is not limited thereto. The disease accompanied by tissue damage, ischemia, or necrosis includes, for example, inflammatory bowel disease, but is not limited thereto. The inflammatory bowel disease includes, but is not limited to, ulcerative colitis and Crohn's disease.

In the present application, the term "nuclear protein" refers to a protein that exerts a certain function in the nucleus and is a protein other than 1) to 6) below:
1) High mobility group box 1 (HMGB1) protein;
2) High mobility group box 2 (HMGB2) protein;
3) High mobility group box 3 (HMGB3) protein;
4) S100 calcium-binding protein A8 (S100A8) protein;
5) S100 calcium-binding protein A9 (S100A9) protein; and
6) Interleukin-1 (IL-1) family cytokines. In one embodiment, the nuclear protein of the present application is a protein that has the activity of mobilizing mesenchymal stem cells into peripheral blood.

In the present application, the term "activity of mobilizing mesenchymal stem cells into peripheral blood" is used interchangeably with "activity to increase the abundance of mesenchymal stem cells in peripheral blood".

The nuclear protein in the present application includes, but is not limited to, for example, a nuclear protein involved in transcriptional regulation. A "protein involved in transcriptional regulation" refers to, among nuclear proteins, a protein having a function of regulating any process in transcription and includes, for example, transcription factors and transcription cofactors, but is not limited thereto.

In the present application, the transcription factor is a protein that controls transcription by binding to DNA by itself or in the form of a complex with other proteins, and includes general transcription factors (proteins that constitute a transcription apparatus), transcriptional regulation factors, transcription elongation factors, factors that regulate transcription by involvement in the transcription termination process, and such.

In the present application, the transcription cofactor is a protein that regulates transcription via protein-protein interactions without binding directly to DNA, and includes but is not limited to co-activators and co-repressors, which regulate transcription by intervening between (binding to both) a transcriptional regulatory factor and a general transcription factor.

In the present application, the "fragment peptide of a nuclear protein" refers to a fragment peptide derived from the above-mentioned nuclear protein. In one embodiment, a fragment peptide of a nuclear protein is a fragment that has an activity of mobilizing mesenchymal stem cells into the peripheral blood.

Fragment peptides of the HMGB1 protein, fragment peptides of the HMGB2 protein, fragment peptides of the HMGB3 protein, fragment peptides of the S100A8 protein, fragment peptides of the S100A9 protein, and fragment peptides of the IL-1 family cytokines are excluded from the fragment peptides of nuclear proteins in the present application.

In the present application, the term "a fragment peptide of a nuclear protein" is used interchangeably with "a fragment peptide derived from a nuclear protein", "a partial peptide derived from a nuclear protein", "a fragment peptide consisting of a portion of a nuclear protein", "a partial peptide consisting of a portion of a nuclear protein", or "a partial peptide of a nuclear protein".

The activity of a nuclear protein or a fragment peptide thereof in the present application to mobilize mesenchymal stem cells into the peripheral blood can be assessed by i) collecting peripheral blood from an individual administered with a nuclear protein or a fragment peptide thereof and an individual not administered with the nuclear protein or fragment peptide, seeding and culturing in a culture dish (several days to 10 days), and counting the number of colonies formed; and ii) confirming that the formed colonies have the ability to adhere to the solid phase and proliferate (self-renewal ability), and the ability to differentiate into osteoblasts, chondrocytes and adipocytes. In i) above, before seeding the collected peripheral blood on a culture dish, red blood cells may be removed from the peripheral blood in a desired manner.

The nuclear protein or fragment peptide thereof in the present application can be obtained as a recombinant by incorporating DNA encoding it into an appropriate expression system, or it can be artificially synthesized. Thus, nuclear proteins or fragment peptides thereof in this application include nuclear proteins and fragment peptides thereof prepared using cells, and artificially synthesized nuclear proteins and fragment peptides thereof (i.e., artificial (synthetic) nuclear proteins and fragment peptides thereof).

In order to obtain the nuclear protein or fragment peptide thereof in the present application by genetic engineering techniques, DNA encoding the peptide may be incorporated into an appropriate expression system and expressed.

Hosts applicable to the present application include, but are not limited to, prokaryotic cells and eukaryotic cells. In addition, hosts applicable to the present application also include bacteria (e.g., *Escherichia coli*), yeast, animal cells (e.g., mammalian cells such as HEK293 cells and CHO cells, insect cells such as silkworm cells), plant cells and such, but are not limited thereto.

As the host/vector system applicable to the present application, for example, the expression vector pGEX and *Escherichia coli* can be shown. pGEX can express a foreign gene as a fusion protein with glutathione S-transferase (GST) (Gene, 67: 31-40, 1988). As such, pGEX into which DNA encoding the nuclear protein or fragment peptide thereof of the present application has been incorporated is introduced into an *E. coli* strain such as BL21 by heat shock, and after culturing for an appropriate period of time, isopropylthio-β-D-galactoside (IPTG) is added to induce the expression of the GST fusion peptide. GST in the present application adsorbs to glutathione Sepharose 4B, and thus the expression product can be easily separated and purified by affinity chromatography.

In addition to this, the following can be applied as a host/vector system for obtaining a genetic recombinant of the nuclear protein or fragment peptide thereof of the present application. First, when a bacterium is used as a host, a vector for expressing a fusion protein using a tag or such is commercially available. In addition, the genetic recombinant of the present application also includes those in which a tag or a partial peptide thereof is added.

The tag added to the nuclear protein or fragment peptide thereof of the present application is not particularly limited as long as it does not affect the activity of the nuclear protein or fragment peptide thereof of the present application, and includes, for example, a histidine tag (for example, 6×His, 10×His), HA tag, FLAG tag, GST tag, T7-tag, HSV-tag, E-tag, lck tag, and B-tag.

Among yeasts, it is known that *Pichia* yeast is effective for the expression of proteins having sugar chains. In terms of the addition of sugar chains, the expression system that uses a Baculovirus vector, which uses an insect cell as a host, is also useful (Bio/Technology, 6:47-55, 1988). Furthermore, mammalian cells are used for transfection with a vector that uses the promoter of CMV, RSV, SV40, or such. These host/vector systems can be used as an expression system for the nuclear proteins or fragment peptides thereof of the present application. In addition, plasmid vectors, retrovirus vectors, lentivirus vectors, adenovirus vectors, adeno-associated virus vectors, Sendai virus vectors, Sendai virus envelope vectors, papilloma virus vectors, and such virus vectors may also be used to introduce the gene, without limitation thereto. The vector may also contain a promoter DNA sequence that effectively induces gene expression, factors that control gene expression, and molecules necessary to maintain the stability of the DNA.

The resulting nuclear proteins or fragment peptides thereof in the present application can be isolated from the host cell or outside of the cell (such as medium), and purified as a substantially pure homogeneous protein. For separation and purification of proteins, any separation and purification methods used in standard protein purification may be utilized, without limitation. For example, chromatography columns, filters, ultrafiltration, salting out, solvent precipitation, solvent extraction, distillation, immunoprecipitation, SDS-polyacrylamide gel electrophoresis, isoelectric focusing, dialysis, recrystallization, and such are appropriately selected and combined for protein separation and purification.

Chromatography includes, for example, affinity chromatography, ion exchange chromatography, hydrophobic chromatography, gel filtration, reverse phase chromatography, adsorption chromatography and such (Marshak et al, Strategies for Protein Purification and Characterization: A Laboratory Course Manual. Ed Daniel R. Cold Spring Harbor Laboratory Press, 1996). These chromatographies can be performed using liquid chromatography such as HPLC and FPLC.

Further, the nuclear protein or fragment peptide thereof in the present application is preferably a substantially purified peptide. Here, "substantially purified" means that the degree of purification of the nuclear protein or fragment peptide thereof of the present application (the ratio of the nuclear protein or fragment peptide thereof of the present application in the entire protein component) is 50% or more, 60% or more, 70% or more, 80% or more, 90% or more, 95% or more, 100% or nearly 100%. The nearly 100% upper limit depends on the purification techniques and analysis techniques of those skilled in the art and may be, for example, 99.999%, 99.99%, 99.9%, or 99%.

Further, the substantially purified nuclear protein or fragment peptide thereof includes those purified by whatever purification method as long as they have the above purity. Examples include, but are not limited to, nuclear proteins and fragment peptides thereof substantially purified by appropriately selecting or combining the above-mentioned chromatography columns, filters, ultrafiltration, salting out, solvent precipitation, solvent extraction, distillation, immunoprecipitation, SDS-polyacrylamide gel electrophoresis, isoelectric focusing, dialysis, recrystallization and such.

On the other hand, the nuclear proteins or fragment peptides thereof in the present application can also be artificially synthesized. In the peptide synthesis method of the present application, peptides can be chemically synthesized by methods such as a peptide liquid-phase synthesis method and a peptide solid-phase synthesis method. The peptide solid-phase synthesis method is one of the methods generally used when chemically synthesizing a peptide. Polystyrene polymer gel beads having a diameter of about 0.1 mm modified with amino groups on the surface are used as a solid phase, from which the amino acid chain is extended one by one via dehydration reaction. When the sequence of the target peptide is completed, it is excised from the solid phase surface to obtain the target substance. Solid phase synthesis enables synthesis of ribosome peptides, which are difficult to synthesize in bacteria, introduction of unnatural amino acids such as D-form and stable isotope ($^2$H, $^{13}$C, $^{15}$N, etc.)-substituted amino acids, introduction of heavy atom-substituted amino acids (e.g., selenoamino acids such as selenomethionine), modification of peptide and protein main chains, and such. When synthesizing a long peptide chain of 70 to more than 100 amino acids in the solid phase method, it can be synthesized by ligating two peptide chains using the native chemical ligation method. The nuclear protein or fragment peptide thereof in the present application may be in the form of a pharmaceutically acceptable salt of the protein or peptide. Examples of pharmaceutically acceptable salts include, but are not limited to, hydrochlorides, acetates, and trifluoroacetates. The nuclear protein or fragment peptide thereof in the present application may be in the form of a solvate of the protein or peptide, or a solvate of a pharmaceutically acceptable salt of the protein or peptide. A solvate refers to a solute molecule to which an arbitrary number of solvent molecules are coordinated, and examples thereof include hydrates, but are not limited thereto.

The amino acid length of the nuclear protein or fragment peptide thereof in the present application includes, for example, 25 to 35 amino acids, 20 to 40 amino acids, 10 to 50 amino acids, 10 to 70 amino acids, and 10 to 100 amino acids, but is not limited thereto.

Examples of the nuclear protein or fragment peptide thereof in the present application include nuclear proteins selected from below or fragment peptides derived therefrom:
1. BTF3 protein (Basic transcription factor 3);
2. SUPT16H protein (Suppressor of Ty 16 Homolog; or Facilitates chromatin transcription complex subunit SPT16);
3. YBX1 protein (Y-Box binding protein 1; or Nuclease-sensitive element-binding protein 1);
4. NPM1 protein (Nucleophosmin 1);
5. PA2G4 protein (Proliferation-associated protein 2G4);
6. PFDN5 protein (Prefoldin subunit 5);

7. PSMC3 protein (Proteasome (Prosome, Macropain) 26S subunit, ATPase 3; or 26S proteasome regulatory subunit 6A);
8. HNRNPK protein (Heterogeneous nuclear ribonucleoprotein K); and
9. Nuclear protein functionally equivalent to a protein selected from 1 to 8.

In light of the examples of the fragment peptides described in the Examples of the present application, the nuclear protein selected from 1 to 8 above is considered to have an activity of mobilizing mesenchymal stem cells to peripheral blood. Therefore, "functionally equivalent" as described in 9 above means functionally equivalent in terms of the activity of mobilizing mesenchymal stem cells to peripheral blood. Therefore, the nuclear protein described in 9 above can be expressed as a nuclear protein having an activity equivalent to that of the protein selected from 1 to 8 (equivalent activity to mobilize mesenchymal stem cells to peripheral blood). The fragment peptide derived from the nuclear protein selected from 1 to 9 above is a fragment peptide having an activity of mobilizing mesenchymal stem cells to peripheral blood.

Since the nuclear protein selected from 1 to 9 above or a fragment peptide thereof has an activity of mobilizing mesenchymal stem cells to peripheral blood, it is considered to have the effect of mobilizing mesenchymal stem cells to peripheral blood, as well as therapeutic effects on inflammatory diseases, autoimmune diseases, diseases accompanied by tissue damage, ischemia, or necrosis, and fibrotic diseases.

In the present application, the nuclear protein or a fragment peptide thereof includes, for example, a nuclear protein selected from below or a fragment peptide derived therefrom:

(I) a nuclear protein comprising an amino acid sequence selected from SEQ ID NOs: 1 to 34;
(II) a nuclear protein consisting of an amino acid sequence selected from SEQ ID NOs: 1 to 34;
(III) a nuclear protein comprising an amino acid sequence resulting from substitution, deletion, insertion, or addition of one or more amino acids in an amino acid sequence selected from SEQ ID NOs: 1 to 34;
(IV) a nuclear protein consisting of an amino acid sequence resulting from substitution, deletion, insertion, or addition of one or more amino acids in an amino acid sequence selected from SEQ ID NOs: 1 to 34;
(V) a nuclear protein comprising an amino acid sequence having about 80% or more sequence identity with an amino acid sequence selected from SEQ ID NOs: 1 to 34;
(VI) a nuclear protein consisting of an amino acid sequence having about 80% or more sequence identity with an amino acid sequence selected from SEQ ID NOs: 1 to 34;
(VII) a nuclear protein encoded by a DNA consisting of a nucleotide sequence selected from SEQ ID NOs: 57 to 90; and
(VIII) a nuclear protein encoded by a DNA that hybridizes under stringent conditions with a DNA consisting of a nucleotide sequence selected from SEQ ID NOs: 57 to 90.

In the present application, the fragment peptide of a nuclear protein includes, for example, a fragment peptide selected from below:

(i) a nuclear protein fragment peptide consisting of a portion of an amino acid sequence selected from SEQ ID NOs: 1 to 34;
(ii) a nuclear protein fragment peptide comprising an amino acid sequence selected from SEQ ID NOs: 35-56;
(iii) a nuclear protein fragment peptide consisting of an amino acid sequence selected from SEQ ID NOs: 35 to 56;
(iv) a nuclear protein fragment peptide consisting of a portion of an amino acid sequence selected from SEQ ID NOs: 35 to 56;
(v) a nuclear protein fragment peptide comprising an amino acid sequence resulting from substitution, deletion, insertion, or addition of one or more amino acids in an amino acid sequence selected from SEQ ID NOs: 35 to 56;
(vi) a nuclear protein fragment peptide consisting of an amino acid sequence resulting from substitution, deletion, insertion, or addition of one or more amino acids in an amino acid sequence selected from SEQ ID NOs: 35 to 56;
(vii) a nuclear protein fragment peptide comprising an amino acid sequence having about 80% or more sequence identity with an amino acid sequence selected from SEQ ID NOs: 35 to 56;
(viii) a nuclear protein fragment peptide consisting of an amino acid sequence having about 80% or more sequence identity with an amino acid sequence selected from SEQ ID NOs: 35 to 56;
(ix) a nuclear protein fragment peptide encoded by a DNA consisting of a nucleotide sequence selected from SEQ ID NOs: 91 to 112; and
(x) a nuclear protein fragment peptide encoded by a DNA that hybridizes under stringent conditions with a DNA consisting of a nucleotide sequence selected from SEQ ID NOs: 91 to 112.

In the present application, "plurality" includes, for example, 1 to 10, 1 to 9, 1 to 8, 1 to 7, 1 to 6, 1 to 5, 1 to 4, 1 to 3, or 1 or 2.

In the present application, "about 80% or more" means, for example, about 85% or more, about 90% or more, about 91% or more, about 92% or more, about 93% or more, about 94% or more, about 95% or more, about 96% or more, about 97% or more, about 98% or more, or about 99% or more.

In the present application, the "stringent conditions" can be shown as conditions of, for example, hybridization at 6×SSC, 40% formamide, 25° C., and washing at 1×SSC, 55° C. Stringency is affected by conditions such as salt concentration, formamide concentration, or temperature, and those skilled in the art can set these conditions to obtain the required stringency.

When the hybridization is carried out under stringent conditions, a DNA having a high homology in terms of nucleotide sequence is selected, and the possibility is increased for the protein isolated as a result to comprise a protein functionally equivalent to (e.g., homologue) a protein consisting of an amino acid sequence selected from SEQ ID NOs: 1 to 34, or to comprise a fragment peptide functionally equivalent to a fragment peptide consisting of an amino acid sequence selected from SEQ ID NOs: 35 to 56. A nucleotide sequence having high homology can exhibit, for example, about 60% or more, about 70% or more, or about 80% or more identity.

Further, in the present application, the fragment peptide of a nuclear protein includes, for example, a fragment peptide selected from below:

(1) a fragment peptide consisting of a portion of an amino acid sequence selected from SEQ ID NOs: 1 to 2, and which is a fragment peptide comprising the amino acid sequence described in SEQ ID NO: 35;
(2) a fragment peptide consisting of a portion of the amino acid sequence described in SEQ ID NO: 3, and which is a fragment peptide comprising the amino acid sequence described in SEQ ID NO: 36;
(3) a fragment peptide consisting of a portion of the amino acid sequence described in SEQ ID NO: 4, and which is a fragment peptide comprising an amino acid sequence selected from SEQ ID NOs: 37 to 39;
(4) a fragment peptide consisting of a portion of an amino acid sequence selected from SEQ ID NOs: 5 to 7, and which is a fragment peptide comprising an amino acid sequence selected from SEQ ID NOs: 40 to 41;
(5) a fragment peptide consisting of a portion of the amino acid sequence described in SEQ ID NO: 8, and which is a fragment peptide comprising the amino acid sequence described in SEQ ID NO: 42;
(6) a fragment peptide consisting of a portion of the amino acid sequence described in SEQ ID NO: 9, and which is a fragment peptide comprising the amino acid sequence described in SEQ ID NO: 43;
(7) a fragment peptide consisting of a portion of the amino acid sequence described in SEQ ID NO: 10, and which is a fragment peptide comprising the amino acid sequence described in SEQ ID NO: 44;
(8) a fragment peptide consisting of a portion of an amino acid sequence selected from SEQ ID NOs: 11 to 16, and which is a fragment peptide comprising the amino acid sequence described in SEQ ID NO: 45;
(9) a fragment peptide consisting of a portion of an amino acid sequence selected from SEQ ID NOs: 17 to 18, and which is a fragment peptide comprising the amino acid sequence described in SEQ ID NO: 46;
(10) a fragment peptide consisting of a portion of the amino acid sequence described in SEQ ID NO: 19, and which is a fragment peptide comprising the amino acid sequence described in SEQ ID NO: 47;
(11) a fragment peptide consisting of a portion of the amino acid sequence described in SEQ ID NO: 20, and which is a fragment peptide comprising an amino acid sequence selected from SEQ ID NOs: 48 to 50;
(12) a fragment peptide consisting of a portion of an amino acid sequence selected from SEQ ID NOs: 21, 23, and 24, and which is a fragment peptide comprising the amino acid sequence described in SEQ ID NO: 51;
(13) a fragment peptide consisting of a portion of an amino acid sequence selected from SEQ ID NOs: 21 to 26, and which is a fragment peptide comprising the amino acid sequence described in SEQ ID NO: 52;
(14) a fragment peptide consisting of a portion of the amino acid sequence described in SEQ ID NO: 27, and which is a fragment peptide comprising the amino acid sequence described in SEQ ID NO: 53;
(15) a fragment peptide consisting of a portion of an amino acid sequence selected from SEQ ID NOs: 28 to 29, and which is a fragment peptide comprising the amino acid sequence described in SEQ ID NO: 54;
(16) a fragment peptide consisting of a portion of the amino acid sequence described in SEQ ID NO: 30, and which is a fragment peptide comprising the amino acid sequence described in SEQ ID NO: 55; and
(17) a fragment peptide consisting of a portion of an amino acid sequence selected from SEQ ID NOs: 31 to 34, and which is a fragment peptide comprising the amino acid sequence described in SEQ ID NO: 56.

The nuclear protein selected from (I) to (VIII) above is a nuclear protein having an activity of mobilizing mesenchymal stem cells into peripheral blood. Further, the fragment peptides derived from a nuclear protein selected from (I) to (VIII) above, nuclear protein fragment peptides selected from (i) to (x) above, and nuclear protein fragment peptides selected from (1) to (17) above are fragment peptides having an activity of mobilizing mesenchymal stem cells into peripheral blood. Therefore, these nuclear proteins and fragment peptides are considered to have the effect of mobilizing mesenchymal stem cells into peripheral blood, as well as therapeutic effects on inflammatory diseases, autoimmune diseases, diseases accompanied by tissue damage, ischemia, or necrosis, and fibrotic diseases.

The present application also provides nuclear proteins selected from 1 to 9 above or fragment peptides derived therefrom, nuclear proteins selected from (I) to (VIII) above or fragment peptides derived therefrom, nuclear protein fragment peptides selected from (i) to (x) above, and nuclear protein fragment peptides selected from (1) from (17) above.

The amino acid sequences described in SEQ ID NOs: 1 to 56 are amino acid sequences of the proteins or peptides shown in Tables 1-1 and 1-2 below.

TABLE 1-1

| SEQ ID NO: | Name | Position in the full-length protein |
|---|---|---|
| 1 | Mouse BTF3 protein isoform 1 | |
| 2 | Mouse BTF3 protein isoform 2 | |
| 3 | Mouse SUPT16H protein | |
| 4 | Mouse YBX1 protein | |
| 5 | Mouse NPM1 protein isoform 1 | |
| 6 | Mouse NPM1 protein isoform 2 | |
| 7 | Mouse NPM1 protein isoform 3 | |
| 8 | Mouse PA2G4 protein | |
| 9 | Mouse PFDN5 protein | |
| 10 | Mouse PSMC3 protein | |
| 11 | Mouse HNRNPK protein isoform 1 | |
| 12 | Mouse HNRNPK protein isoform 2 | |
| 13 | Mouse HNRNPK protein isoform 3 | |
| 14 | Mouse HNRNPK protein isoform 4 | |
| 15 | Mouse HNRNPK protein isoform 5 | |
| 16 | Mouse HNRNPK protein isoform 6 | |
| 17 | Human BTF3 protein isoform A | |
| 18 | Human BTF3 protein isoform B | |
| 19 | Human SUPT16H protein | |
| 20 | Human YBX1 protein | |
| 21 | Human NPM1 protein isoform 1 | |
| 22 | Human NPM1 protein isoform 2 | |
| 23 | Human NPM1 protein isoform 3 | |
| 24 | Human NPM1 protein isoform 4 | |
| 25 | Human NPM1 protein isoform 5 | |
| 26 | Human NPM1 protein isoform 6 | |
| 27 | Human PA2G4 protein | |

TABLE 1-2

| | | |
|---|---|---|
| 28 | Human PFDN5 protein isoform α | |
| 29 | Human PFDN5 protein isoform γ | |
| 30 | Human PSMC3 protein | |
| 31 | Human HNRNPK protein isoform a | |
| 32 | Human HNRNPK protein isoform b | |
| 33 | Human HNRNPK protein isoform c | |
| 34 | Human HNRNPK protein isoform d | |
| 35 | Mouse BTF3 peptide-1 | 63-92 |
| 36 | Mouse SUPT16H peptide-1 | 108-137 |
| 37 | Mouse YBX1 peptide-1 | 174-203 |
| 38 | Mouse YBX1 peptide-2 | 225-254 |
| 39 | Mouse YBX1 peptide-3 | 273-302 |

TABLE 1-2-continued

| | | |
|---|---|---|
| 40 | Mouse NPM1 peptide-1 | 209-238 |
| 41 | Mouse NPM1 peptide-2 | 221-250 |
| 42 | Mouse PA2G4 peptide-1 | 43-72 |
| 43 | Mouse PFDN5 peptide-1 | 99-128 |
| 44 | Mouse PSMC3 peptide-1 | 55-84 |
| 45 | Mouse HNRNPK peptide-1 | 242-271 |
| 46 | Human BTF3 peptide-1 | 65-94 |
| 47 | Human SUPT16H peptide-1 | 108-137 |
| 48 | Human YBX1 peptide-1 | 176-205 |
| 49 | Human YBX1 peptide-2 | 227-256 |
| 50 | Human YBX1 peptide-3 | 275-304 |
| 51 | Human NPM1 peptide-1 | 210-240 |
| 52 | Human NPM1 peptide-2 | 223-252 |
| 53 | Human PA2G4 peptide-1 | 43-72 |
| 54 | Human PFDN5 peptide-1 | 99-128 |
| 55 | Human PSMC3 peptide-1 | 52-81 |
| 56 | Human HNRNPK peptide-1 | 242-271 |

The nucleotide sequences described in SEQ ID NOs: 57 to 112 are examples of the nucleotide sequences of DNAs encoding the proteins or peptides shown in Tables 2-1 and 2-2 below. Other DNA sequences encoding the proteins or peptides shown in Tables 2-1 and 2-2 below can be produced by a method of converting the amino acid residues of the proteins or peptides to corresponding codons using codon tables known to those skilled in the art (reverse translation). Reverse translation can be performed by using a variety of software (including programs, algorithms, etc.) developed for the analysis of amino acid and nucleic acid sequences as desired.

TABLE 2-1

| SEQ ID NO: | Name | Position in full length DNA |
|---|---|---|
| 57 | Mouse BTF3 protein isoform 1 | |
| 58 | Mouse BTF3 protein isoform 2 | |
| 59 | Mouse SUPT16H protein | |
| 60 | Mouse YBX1 protein | |
| 61 | Mouse NPM1 protein isoform 1 | |
| 62 | Mouse NPM1 protein isoform 2 | |
| 63 | Mouse NPM1 protein isoform 3 | |
| 64 | Mouse PA2G4 protein | |
| 65 | Mouse PFDN5 protein | |
| 66 | Mouse PSMC3 protein | |
| 67 | Mouse HNRNPK protein isoform 1 | |
| 68 | Mouse HNRNPK protein isoform 2 | |
| 69 | Mouse HNRNPK protein isoform 3 | |
| 70 | Mouse HNRNPK protein isoform 4 | |
| 71 | Mouse HNRNPK protein isoform 5 | |
| 72 | Mouse HNRNPK protein isoform 6 | |
| 73 | Human BTF3 protein isoform A | |
| 74 | Human BTF3 protein isoform B | |
| 75 | Human SUPT16H protein | |
| 76 | Human YBX1 protein | |
| 77 | Human NPM1 protein isoform 1 | |
| 78 | Human NPM1 protein isoform 2 | |
| 79 | Human NPM1 protein isoform 3 | |
| 80 | Human NPM1 protein isoform 4 | |
| 81 | Human NPM1 protein isoform 5 | |
| 82 | Human NPM1 protein isoform 6 | |
| 83 | Human PA2G4 protein | |
| 84 | Human PFDN5 protein isoform α | |

TABLE 2-2

| | | |
|---|---|---|
| 85 | Human PFDN5 protein isoform γ | |
| 86 | Human PSMC3 protein | |
| 87 | Human HNRNPK protein isoform a | |
| 88 | Human HNRNPK protein isoform b | |
| 89 | Human HNRNPK protein isoform c | |
| 90 | Human HNRNPK protein isoform d | |
| 91 | Mouse BTF3 peptide-1 | 187-276 |
| 92 | Mouse SUPT16H peptide-1 | 322-411 |
| 93 | Mouse YBX1 peptide-1 | 520-609 |
| 94 | Mouse YBX1 peptide-2 | 673-762 |
| 95 | Mouse YBX1 peptide-3 | 817 906 |
| 96 | Mouse NPM1 peptide-1 | 625-714 |
| 97 | Mouse NPM1 peptide-2 | 661-750 |
| 98 | Mouse PA2G4 peptide-1 | 127-216 |
| 99 | Mouse PFDN5 peptide-1 | 295-384 |
| 100 | Mouse PSMC3 peptide-1 | 163-252 |
| 101 | Mouse HNRNPK peptide-1 | 724-813 |
| 102 | Human BTF3 peptide-1 | 193-282 |
| 103 | Human SUPT16H peptide-1 | 322-411 |
| 104 | Human YBX1 peptide-1 | 526-615 |
| 105 | Human YBX1 peptide-2 | 679-768 |
| 106 | Human YBX1 peptide-3 | 823-912 |
| 107 | Human NPM1 peptide-1 | 628-720 |
| 108 | Human NPM1 peptide-2 | 667-756 |
| 109 | Human PA2G4 peptide-1 | 127-216 |
| 110 | Human PFDN5 peptide-1 | 295-384 |
| 111 | Human PSMC3 peptide-1 | 154-243 |
| 112 | Human HNRNPK peptide-1 | 724-813 |

In the present application, the nuclear protein or a fragment peptide thereof is a nuclear protein or a fragment peptide thereof that comprises, for example, a nuclear localization signal (NLS). A nuclear localization signal (NLS) is an amino acid sequence having a certain pattern and has a function of transferring a protein/peptide having the amino acid sequence into the nucleus.

For example, many nuclear proteins are known to carry NLS in their amino acid sequences, and move into the nucleus by binding to the nuclear transport receptor (also referred to as nuclear transport proteins and nuclear transport factors) that recognizes the NLS.

Examples of currently known NLS (hereinbelow referred to as a known NLS) include those listed in Tables 3-1 and 3-2 below.

TABLE 3-1

| Type | | Sequence pattern | Specific example (source) |
|---|---|---|---|
| cNLS (classical NLS) | monopartite | K-K/R-X-K/R (SEQ ID NO: 113) | PKKKRRV (Lange et al., (2007) J. Biol. Chem., 282, 5101-5105; Kosugi et al., (2009) J. Biol. Chem., 284, 478-485., etc.) (SEQ ID NO: 114) |
| | bipartite | (K/R)(K/R)X$_{10-12}$(K/R)$_{3/5}$ ((K/R)$_{3/5}$ = at least 3 amino acids among 5 consecutive amino acids are K or R) (SEQ ID NO: 115) | KRPAATKKAGQAKKKK (Kosugi et at., (2009) J. Biol. Chem., 284, 478-485., etc.) (SEQ ID NO: 118) |

TABLE 3-1-continued

| Type | Sequence pattern | Specific example (source) |
|---|---|---|
| | KRX$_{10-12}$K(K/R)(K/R) (SEQ ID NO: 116)<br>KRX$_{10-12}$K(K/R)X(K/R) (SEQ ID NO: 117) | |
| PY-NLS | Those having the following 2 motifs:<br>1) R/K/H-X$_{(2-5)}$-P-Y (SEQ ID NO: 119)<br>2) φG/A/Sφφ X$_{(11-13)}$PY<br>φ is an amino acid having hydrophobic side-chain) (SEQ ID NO: 120) | FGNYNNQSSNFGPMKGGNF<br>GGRSSGPY<br>(Lee et al., (2006) Cell, 126, 543-558; Süel et al., (2008) P LoS Biol., 6, e137, etc.) (SEQ ID NO: 121) |
| | Those having the following 2 motifs:<br>1) R/K/H-X$_{(2-5)}$-P-Y (SEQ ID NO: 119)<br>2) basic-enriched$_{(508)}$X$_{(8-10)}$PY ("basic-enriched" is a region rich in basic amino acids) (SEQ ID NO: 122) | GEGERPAQNEKRKEKNIKRG<br>GNRFEPY<br>(Lee et al., (2006) Cell, 126, 543-558; Süel et al., (2008) PLoS Biol., 6, e137, etc.) (SEQ ID NO: 123) |

TABLE 3-2

Figure 2:
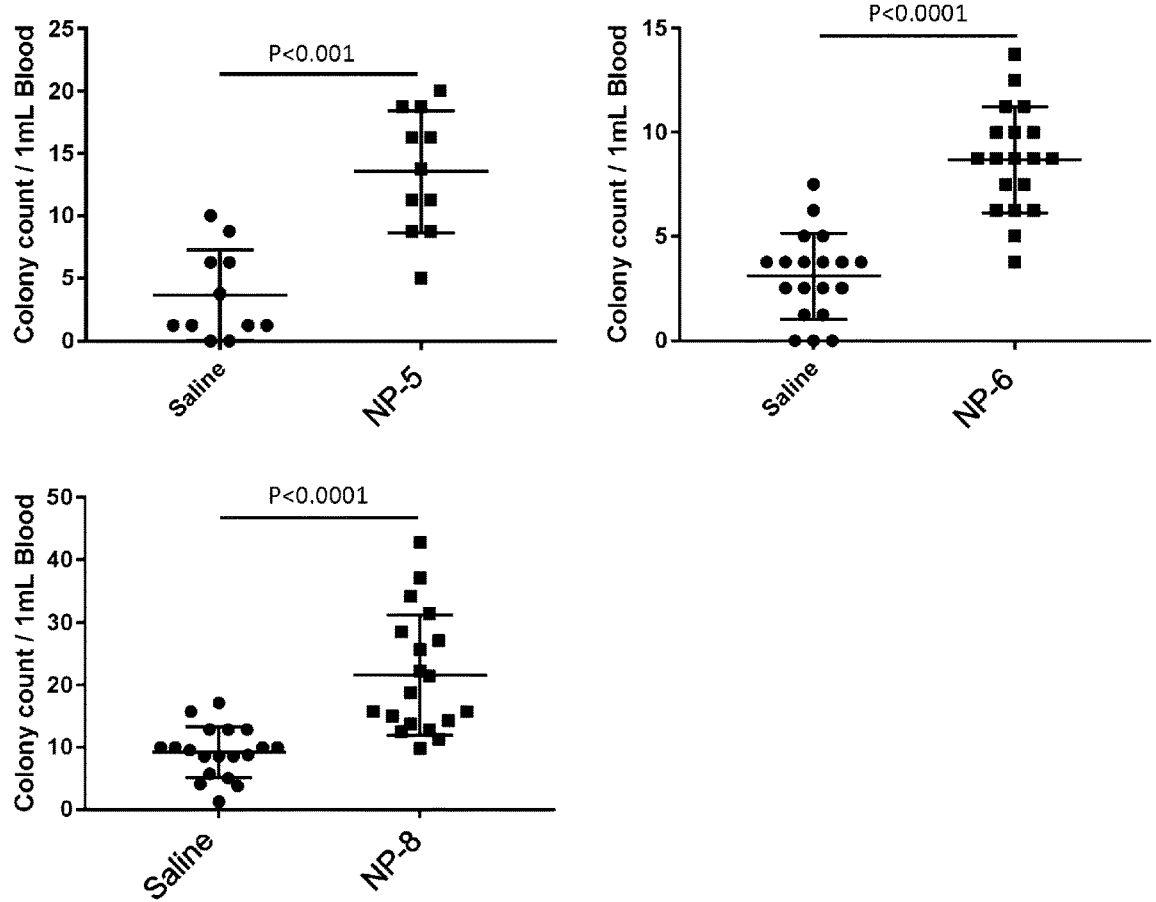
FIG. 2 is a plot of the number of colonies obtained by culturing peripheral blood 14 hours after administration of saline or the peptides. The number of colonies is shown as a value converted per 1 mL of collected peripheral blood. The long horizontal bar represents the mean value, and the short horizontal bars represent the standard deviation.
Figure 3:
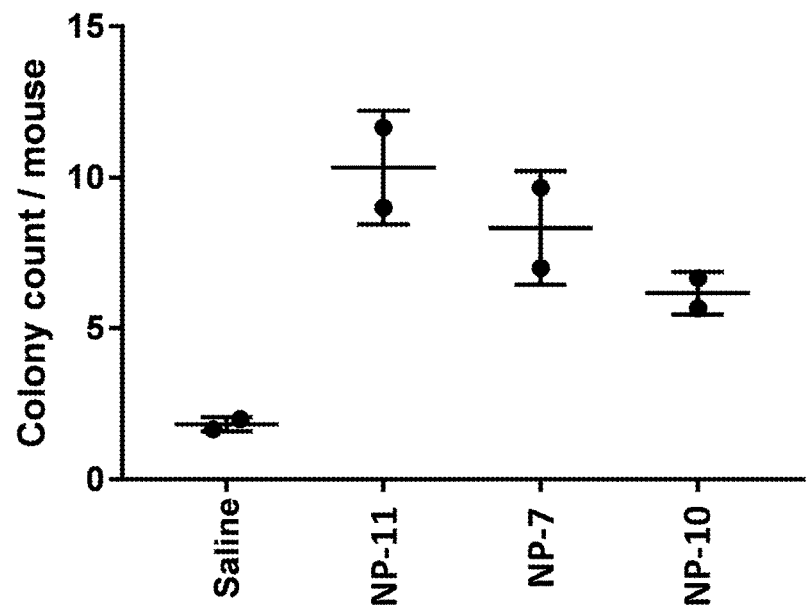
FIG. 3 is a plot of the number of colonies obtained by culturing peripheral blood 16 hours after administration of saline or the peptides. The number of colonies is shown as a value per peripheral blood volume (about 800 µL) collected from one mouse. The long horizontal bar represents the average value, and the short horizontal bars represent the standard deviation.
Figure 4:
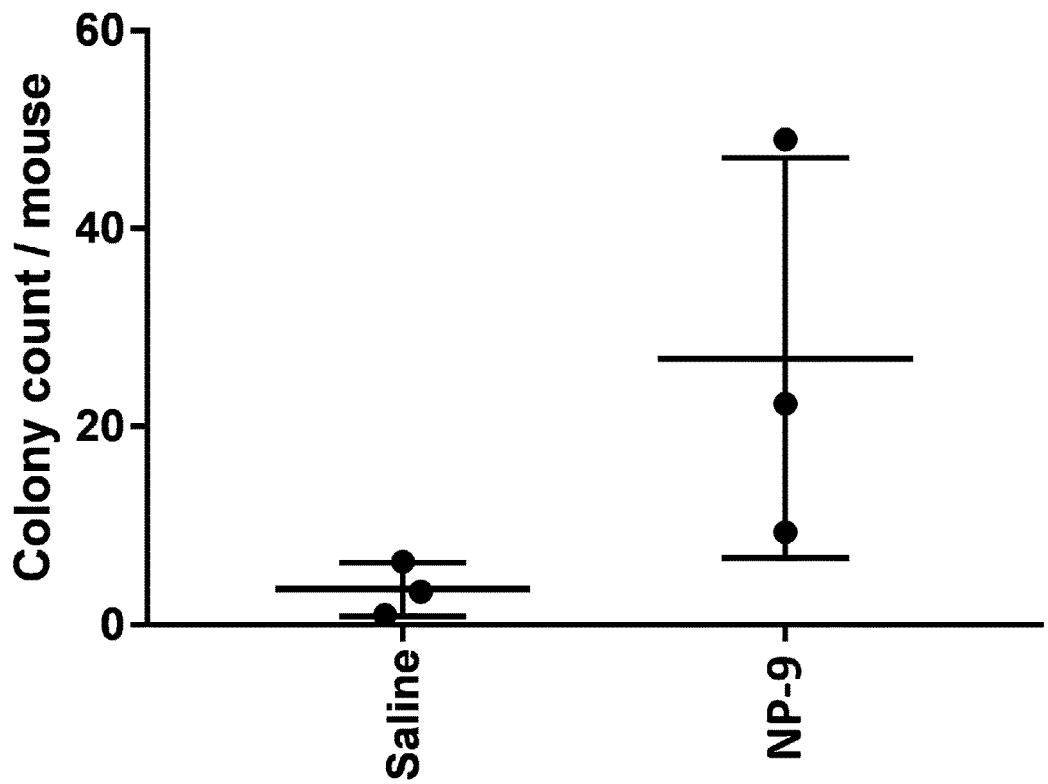
FIG. 4 is a plot of the number of colonies obtained by culturing peripheral blood 24 hours after administration of saline or the peptides. The number of colonies is shown as a value per peripheral blood volume (about 800 µL) collected from one mouse. The long horizontal bar represents the average value, and the short horizontal bars represent the standard deviation.
Figure 5:
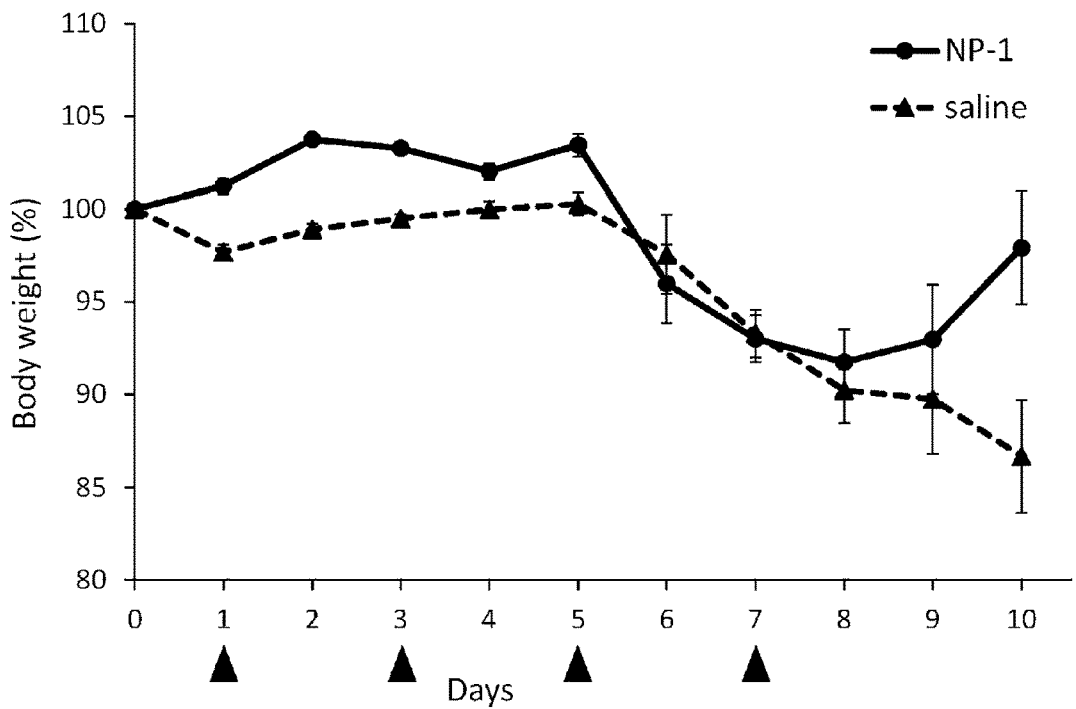
FIG. 5 is a graph that shows the body weight change of the mice. In the graph, "saline" indicates the control group, and "NP-1" indicates the peptide NP-1 administration group. On the horizontal axis, the number of days indicates the number of days after the start of drinking the aqueous solution of dextran sulfate sodium (DSS), and triangle indicates the date of administration of physiological saline (control group) or the peptide (NP-1 administration group).
Figure 6:
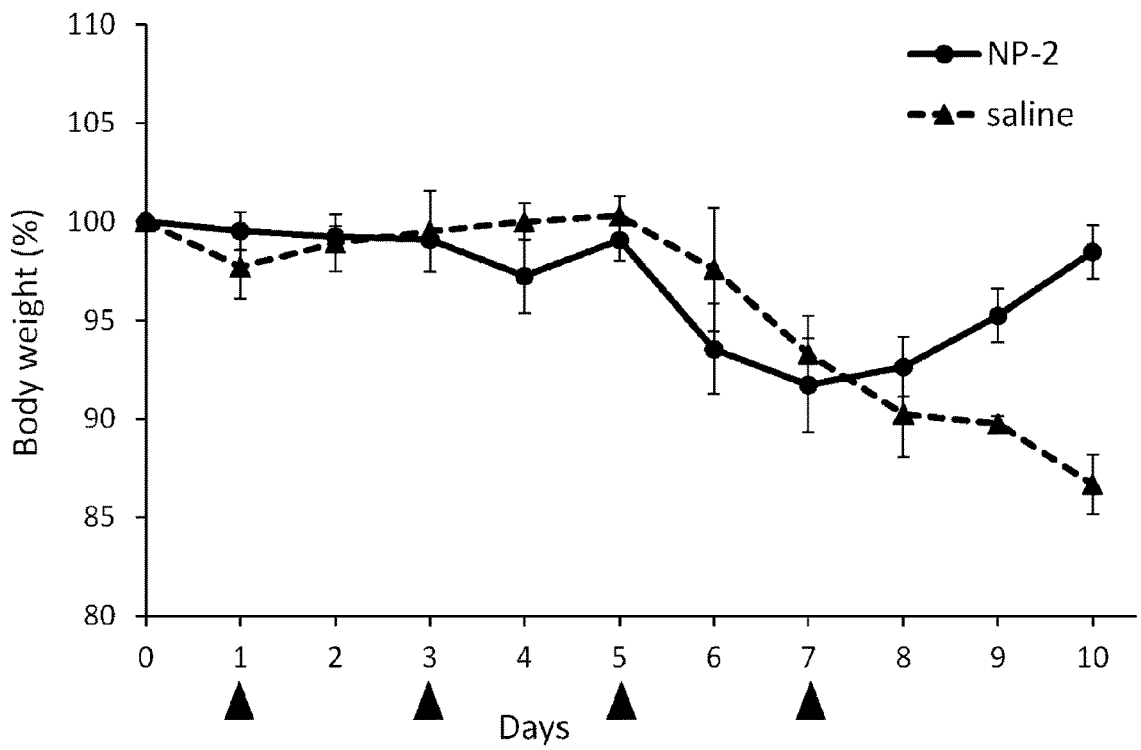
FIG. 6 is a graph that shows the body weight change of the mice. In the graph, "saline" indicates the control group, and "NP-2" indicates the peptide NP-2 administration group. On the horizontal axis, the number of days indicates the number of days after the start of drinking the aqueous solution of dextran sulfate sodium (DSS), and triangle indicates the date of administration of physiological saline (control group) or the peptide (NP-2 administration group).
Figure 7:
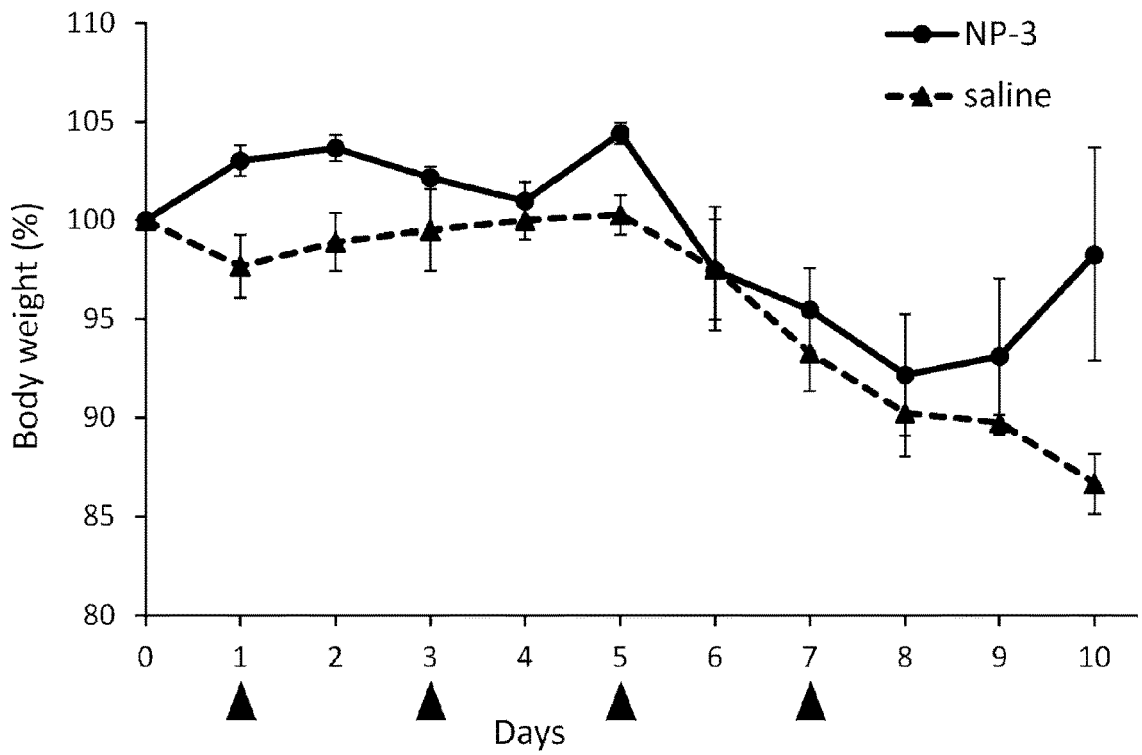
FIG. 7 is a graph that shows the body weight change of the mice. In the graph, "saline" indicates the control group, and "NP-3" indicates the peptide NP-3 administration group. On the horizontal axis, the number of days indicates the number of days after the start of drinking the aqueous solution of dextran sulfate sodium (DSS), and triangle indicates the date of administration of physiological saline (control group) or the peptide (NP-3 administration group).
Figure 8:
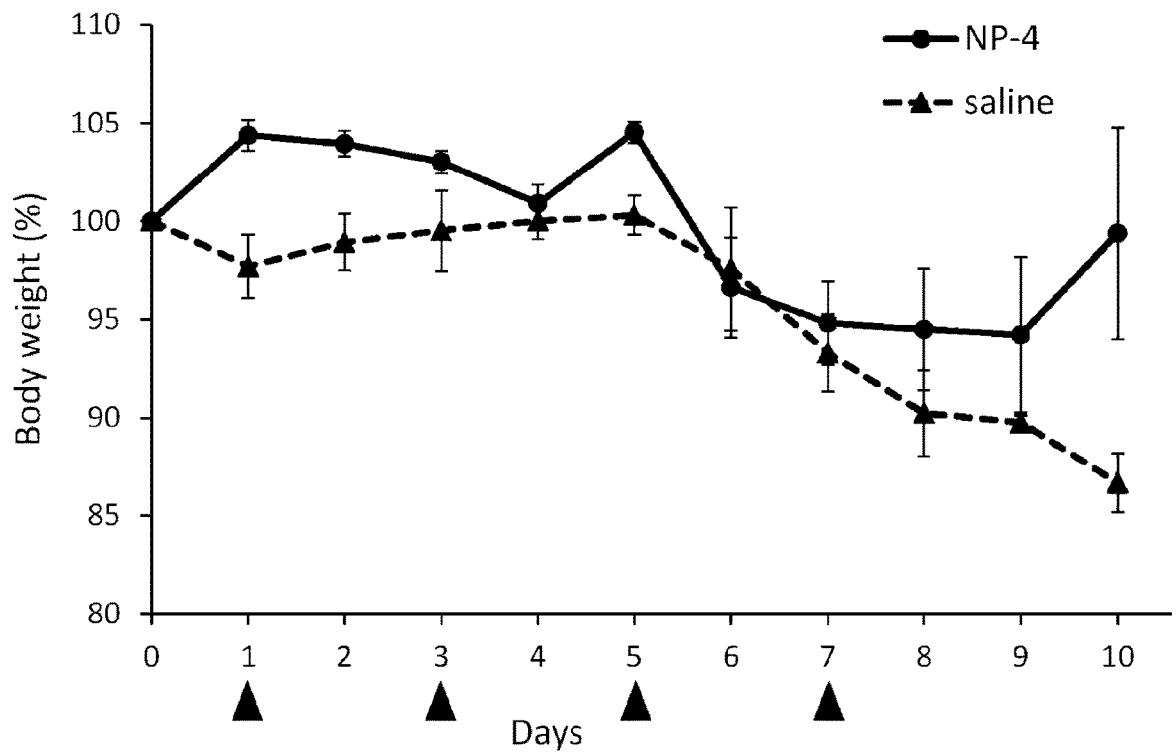
FIG. 8 is a graph that shows the body weight change of the mice. In the graph, "saline" indicates the control group, and "NP-4" indicates the peptide NP-4 administration group. On the horizontal axis, the number of days indicates the number of days after the start of drinking the aqueous solution of dextran sulfate sodium (DSS), and triangle indicates the date of administration of physiological saline (control group) or the peptide (NP-4 administration group).

| BIB domain (β-like importin binding domain) | Amino acid residues 32-74 of rpL23a protein | VHSHKKKKIRTSPTFRRPKTL<br>RLRRQPKYPRKSAPRRNKLD<br>HY<br>(Jäkel, S. & Görlich, D. (1998) EMBO J., 17, 4491-4502) (SEQ ID NO: 124) |
|---|---|---|
| BIB domain like sequence | (1) MSHRKFSAPRHGSLG<br>FLPRKRSSRHRGKVKS<br>FPKDDP (SEQ ID NO: 125)<br>(2) EVTNDFVMLKGCVVG<br>TKKRVLTLRKSLLVQTK<br>RRALEKIDLKFIDTTSK<br>F (SEQ ID NO: 126)<br>(3) SLGQSASETEEDTVSV<br>SKKEKNRKRRNRKKK<br>KKPQRVRGVSSESSG<br>DREK (SEQ ID NO: 127)<br>(4) PTRYSVDIPLDKTVVN<br>KDVFRDPALKRKARRE<br>AKVKFEERYKTGKNK<br>WFF (SEQ ID NO: 128)<br>(5) KMFKGKRGAQLAKDIA<br>RRSKTFNPGAGLPTDK<br>KKGGPSPGDVEAIKNA<br>IA (SEQ ID NO: 129) | Kimura et al., Mol. Cell. Proteomics (2013), 12, 145-157, FIG. 3C 2)-3) |

In addition, known NLS include sequences registered on the NLSdb database (<https://rostlab.org/services/nlsdb/>). The sequences registered on NLSdb can be viewed and downloaded on the above website. Among the NLS sequences registered on NLSdb, those whose annotation type is "Experimental" or "By Expert" can be estimated as having a function of translocating a protein/peptide into the nucleus, and are therefore treated as known NLS in the present application.

The NLS in the present application may be an NLS predicted by using a specific program (hereinbelow referred to as a predicted NLS). Whether a predicted NLS is contained in the desired amino acid sequence can be determined using the following program: SeqNLS (Lin et al., PLoS One. 2013 Oct. 29; 8 (10):e76864) or NLStradamus (Nguyen et al., BMC Bioinformatics. 2009 Jun. 29; 10:202).

In one embodiment, the NLS is a known NLS. In one embodiment, the NLS is a known NLS selected from the group consisting of cNLS, PY-NLS, BIB domain, and BIB domain-like sequences. In one embodiment, the cNLS is a monopartite cNLS. In one embodiment, the monopartite cNLS is KKEK (SEQ ID NO: 130).

An effective amount of a nuclear protein of the present application or a fragment peptide thereof, or a pharmaceutical composition comprising the same (hereinafter referred to as a pharmaceutical composition and such) is administered to a subject for the treatment of diseases and conditions described herein.

The effective amount in the present application means an amount sufficient for the treatment of the diseases or pathological conditions described herein. The treatment in the present application includes alleviation, delay, inhibition, amelioration, remission, cure, and full recovery, but are not limited thereto.

There is no limitation on the site of administration of the pharmaceutical composition and such of the present application, and the pharmaceutical composition and such of the present application can exert its effect when administered to any site, such as a site where the symptoms of the disease or pathological condition appear or a site nearby, a site different from these sites (sites other than these sites), a site separated from a site where the symptoms of the disease or pathological condition appear, a site distal to a site where the symptoms of the disease or pathological condition appear, or a site distal and ectopic to a site where the symptoms of the disease or pathological condition appear.

Further, the pharmaceutical composition and such of the present application can exert its effect when administered to any tissue, such as a tissue different from a tissue in which the symptoms of the disease or the pathological condition appear, a tissue separated from a tissue in which the symptoms of the disease or the pathological condition appear, a tissue distal to a tissue in which the symptoms of the disease or the pathological condition appear, or a tissue distal and ectopic to a tissue in which the symptoms of the disease or pathological condition appear.

Methods of administering the pharmaceutical composition and such of the present application include, but are not limited to, oral administration and parenteral administration, and methods of parenteral administration include intravascular administration (intra-arterial administration, intravenous administration, etc.), intramuscular administration, subcutaneous administration, intradermal administration, intraperitoneal administration, nasal administration, pulmonary administration, transdermal administration, and such. In addition, the pharmaceutical composition and such of the present application can be administered systemically or locally (for example, subcutaneously, intradermally, or to the skin surface, eyeball, or palpebral conjunctiva, nasal mucosa, oral and gastrointestinal mucosa, vaginal and endometrial mucosa, or injured site) by injection administration, for example, intravenous injection, intramuscular injection, intraperitoneal injection, and subcutaneous injection.

In place of the nuclear protein of the present application or a fragment peptide thereof, a cell secreting the nuclear protein or a fragment peptide thereof, a gene therapy vector into which a DNA encoding the nuclear protein or fragment peptide thereof is inserted, and a pharmaceutical composition comprising them can be used.

In addition, the administration method can be appropriately selected depending on the age and symptoms of a patient. When the pharmaceutical composition and such of the present application is administered, for example, the dose can be selected from the range of 0.0000001 mg to 1000 mg per kilogram of body weight per administration. Alternatively, for example, the dose can be selected from the range of 0.00001 to 100000 mg/body per patient. When administering cells secreting the nuclear protein of the present application or a fragment peptide thereof or gene therapy vectors into which DNA encoding the nuclear protein or a fragment peptide thereof is inserted, they can be administered so that the amount of the nuclear protein or fragment peptide thereof is within the above range. However, the pharmaceutical compositions in the present application are not limited to these dosages.

The pharmaceutical compositions of the present application can be formulated according to conventional methods (e.g., Remington's Pharmaceutical Science, latest edition, Mark Publishing Company, Easton, U.S.A.), and may contain pharmaceutically acceptable carriers or additives together. Examples include, but are not limited to, surfactants, excipients, coloring agents, perfumes, preservatives, stabilizers, buffers, suspending agents, isotonizing agents, binding agents, disintegrants, lubricants, fluidity-promoting agents, and flavoring agents. Other commonly used carriers can also be used as appropriate. Specific examples include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium-chain fatty acid triglyceride, polyoxyethylene hydrogenated castor oil 60, white sugar, carboxymethyl cellulose, cornstarch, and inorganic salts.

All prior art documents cited herein are incorporated herein as references.

Herein below, the present invention will be further illustrated with reference to Examples, but it is not to be construed as being limited thereto.

EXAMPLES

Example 1

Mobilization of Mesenchymal Stem Cells by Fragment Peptides of Nuclear Proteins
(1) Materials and Methods
i) Peptide Production Fragment peptides of the nuclear proteins shown in the table below were chemically synthesized by the solid phase method (all of the obtained peptides are in the form of trifluoroacetic acid (TFA) salts).

TABLE 4

| Name | Another name considering the name of the protein origin | SEQ ID NO |
|---|---|---|
| NP-1 | Mouse BTF3 peptide-1 | 35 |
| NP-2 | Mouse SUPT16H peptide-1 | 36 |
| NP-3 | Mouse YBX1 peptide-1 | 37 |
| NP-4 | Mouse YBX1 peptide-2 | 38 |
| NP-5 | Mouse YBX1 peptide-3 | 39 |
| NP-6 | Mouse NPM1 peptide-1 | 40 |
| NP-7 | Mouse NPM1 peptide-2 | 41 |
| NP-8 | Mouse PA2G4 peptide-1 | 42 |
| NP-9 | Mouse PFDN5 peptide-1 | 43 |
| NP-10 | Mouse PSMC3 peptide-1 | 44 |
| NP-11 | Mouse HNRNPK peptide-1 | 45 | ii) Peptide Administration

C57BL/6J mice (8 weeks old, male, body weight 25 g) were prepared and divided into groups to which any of peptides NP-1 to NP-11 described in the above table were administered and a control group. The peptide was administered by injecting into the tail vein, a solution of each peptide adjusted to a concentration of 1 µg/µL using physiological saline as a solvent in an amount of 100 µL/animal (4 mg/kg dose of peptide). For the control group, physiological saline was injected into the tail vein in an amount of 100 µL/animal.

iii) Cell Collection from Peripheral Blood

Predetermined time after the administration of physiological saline or peptides NP-1 to NP-11 (NP-1 to NP-6 and NP-8: after 14 hours; NP-7, NP-10 and NP-11: after 16 hours; NP-9: after 24 hours), about 800 µL to 1000 µL of peripheral blood was collected from the hearts under general anesthesia (1 mL syringe containing heparin was used). To remove red blood cells, an equal volume of Hetasep (STEMCELL Technologies Inc., Cat No. ST-07906) as the collected blood was added and centrifuged for 2 min at 100G, incubated for 15 min at room temperature, and then the supernatant was collected. The supernatant was used in the next experiment as a sample containing nucleated cells in peripheral blood.

iv) Colony Assay

The supernatant (sample containing peripheral blood-derived cells) obtained by the above procedure was seeded on collagen I-coated 6-well plates (Corning, Cat No. 356400), and cultured for 10 days under the conditions of 37° C., 5% $CO_2$ and 5% $O_2$, using a medium containing Expansion Medium prepared using the MesenCult Expansion Kit (STEMCELL Technologies, Cat No. ST-05513) according to the manual of the kit, 1% L-glutamine (Nacalai Tesque Inc.), 10 µM ROCK inhibitor (Y27632, Tocris Bioscience) and 1% penicillin/streptomycin (Nacalai Tesque Inc.) (all numerical values are final concentrations). The medium was replaced with fresh medium twice a week during the culture period. On the $10^{th}$ day of culture, cells on the plates were stained with a Differential Quik Stain Kit (Sysmex Corporation, Cat No. 16920), and the number of colonies containing 50 or more cells was counted.

In the experiments conducted by the present inventors so far, all the colonies obtained as a result of culturing peripheral blood on a solid phase such as a dish or a plate have adherability to the solid phase and have self-renewal ability. In addition, they have been confirmed to be PDGFRα positive, and have the ability to differentiate into bone, cartilage, fat, epithelium, and such.

In addition, the colonies obtained as a result of culturing, on a solid phase, peripheral blood after administration of a peptide consisting of amino acid residues 1-44 of the human HMGB1 protein (hereinafter, HMGB1 peptide 1-44), which has an activity of mobilizing mesenchymal stem cells into peripheral blood, have been confirmed to have adherability to solid phase and self-renewal ability, and to be PDGFRα positive. They have also been confirmed to have a gene expression profile characteristic to mesenchymal stem cells, based on the results of clustering the transcriptome analysis data and performing gene ontology analysis.

Furthermore, it has been confirmed that the number of colonies obtained by solid-phase culture is larger in the peripheral blood after administration of HMGB1 peptide 1-44 than in the peripheral blood after administration of physiological saline.

Therefore, the colonies obtained as a result of culturing peripheral blood on a solid phase are mesenchymal stem cells, and it is considered that an increase in the number of colonies detected in a solid phase culture of peripheral blood indicates an increase in the number of mesenchymal stem cells in the peripheral blood.

In addition, since usually mesenchymal stem cells are rarely present in peripheral blood, it is thought that the increased amount of mesenchymal stem cells was mobilized into peripheral blood from tissues other than peripheral blood (for example, bone marrow).

From the above, the number of colonies detected in the solid-phase culture of peripheral blood after administration of a test substance can be used as an indicator of the activity of the test substance to mobilize mesenchymal stem cells into peripheral blood.

(2) Result

In the mice administered with any of the peptides NP-1 to NP-11, the number of colonies obtained on the plate by culturing the peripheral blood-derived cells was larger than that in the mice administered with physiological saline (FIGS. 1 to 4).

As described above, an increase in the number of colonies detected by the colony assay described herein indicates an increase in the number of mesenchymal stem cells in peripheral blood, and thus these results demonstrate that the fragment peptides of the nuclear proteins have the activity of mobilizing mesenchymal stem cells into peripheral blood.

Example 2

Efficacy of Nuclear Protein-Derived Peptides for Inflammatory Bowel Disease (1) Materials and Methods i) Drugs Dextran sulfate sodium (DSS) (molecular weight 5,000-6,000, manufactured by Nacalai Tesque Inc., Catalog No. 10930-94) was dissolved in water to prepare a 2.5% (w/v) DSS aqueous solution. In addition, the peptides NP-1 to NP-4 (all TFA salts) described in Example 1 were used as test substances.

ii) Generation of the Inflammatory Bowel Disease (IBD) Model Mice

C57BL/6J mice (8 weeks old, male, body weight about 20 g) were allowed free drinking of 2.5% DSS aqueous solution in place of purified water (RO water) to induce colitis (drinking of the DSS aqueous solution was continued for 10 days).

iii) Peptide Administration

The IBD model mice prepared as described above were divided into peptide administration groups (NP-1 to NP-4, each n=3) and a control group (n=3). Administration of each peptide was performed on Days 1, 3, 5 and 7 after the start of drinking the DSS aqueous solution, by adjusting the peptide solution to a concentration of 0.5 mg/mL using physiological saline as the solvent, and injecting the amount of 200 µL/animal (5 mg/kg dose of peptide) into the tail vein. In the control group, 200 µL/animal of physiological saline was injected into the tail vein on Days 1, 3, 5 and 7 after the start of drinking the DSS aqueous solution.

iv) Evaluation of the Effect of Peptide Administration

Mice were weighed daily for 10 days from the start of drinking the DSS aqueous solution.

(2) Result

Changes in the body weight of mice during the test period are shown in FIGS. 5 to 8 (see "Saline" for the control group and "NP-1", "NP-2", "NP-3", "NP-4" for the peptide NP-1 to NP-4 administration groups.). The body weight of the control group decreased with the passage of days, and was about 87% on the $10^{th}$ day after the start of drinking the DSS aqueous solution as compared with that before the start of the DSS drinking. On the other hand, in all of the peptide NP-1 to NP-4 administration groups, the body weight loss was suppressed as compared with the control group, and the body weight on the $10^{th}$ day after the start of drinking the DSS aqueous solution was significantly larger than that in the control group.

One of the symptoms of IBD is known to be occurrence of body weight loss, and the reason is thought to be malnutrition due to inflammation and tissue damage (such as ulcer) that occur in the intestinal mucosa. Furthermore, intravenous injection of mesenchymal stem cells in an animal IBD model is known to improve various symptoms including body weight loss, epithelial damage in the intestinal tract, infiltration of inflammatory cells, and such. Such improvement of symptoms is due to suppression of inflammation of the intestinal mucosa by the anti-inflammatory effect of mesenchymal stem cells, and resulting facilitation of mucosal tissue regeneration, and such.

This time, by administering fragment peptides of nuclear proteins of the present application to the IBD model mice, the body weight loss was suppressed. This is thought to be the result of mobilization of mesenchymal stem cells into peripheral blood by the action of the fragment peptides of the nuclear proteins, and exhibition of the inflammation-suppressing effect and tissue regeneration effect by the cells.

Example 3

Efficacy of Nuclear Protein-Derived Peptides on Psoriasis
(1) Materials and Methods
i) Drugs To induce psoriasis by imiquimod, a cream containing 5% imiquimod (Beseruna cream 5%, Mochida Pharmaceutical Co., Ltd.) was used. In the drawing corresponding to the Example of the present application, imiquimod is referred to as IMQ. In addition, the peptide NP-3 (TFA salt) described in Example 1 was used as a test substance.

ii) Generation of Psoriasis Model Mice

C57BL/6 mice (7 weeks old, female, body weight about 20 g) were prepared. To induce psoriasis, a cream containing 5% imiquimod was applied on the auricular skin of the mice at an amount of 25 mg/ear/day (1.25 mg/ear/day imiquimod) once a day for seven days. Moreover, mice without imiquimod application (hereinafter, referred to as "normal mice") were used as a comparison target.

iii) Peptide Administration

The psoriasis model mice prepared as described above were divided into a peptide-administered group (n=4) and a control group (n=4). Administration of the test substance was carried out from the first day of the start of imiquimod application (Day 1) for seven days, by injecting into the tail vein 100 µL/day of the NP-3 peptide solution which has been adjusted to a concentration of 1 using physiological saline as a solvent (5 mg/kg/day as peptide dose). In the control group, physiological saline was injected into the tail vein in an amount of 100 µL/day, from the first day of the start of imiquimod application for seven days. No substance was administered to normal mice (n=4).

iv) Evaluation of the Effects of Peptide Administration

During the test period, the auricle thickness of mice was measured daily using a micrometer (manufactured by Mitutoyo Co., Ltd., Product No. CLM1-15QM), and the size of change from the auricle thickness before the start of imiquimod application (Day 0) was calculated. The degree of skin thickening was evaluated using the size of change as an index.

(2) Result

Figure 9:
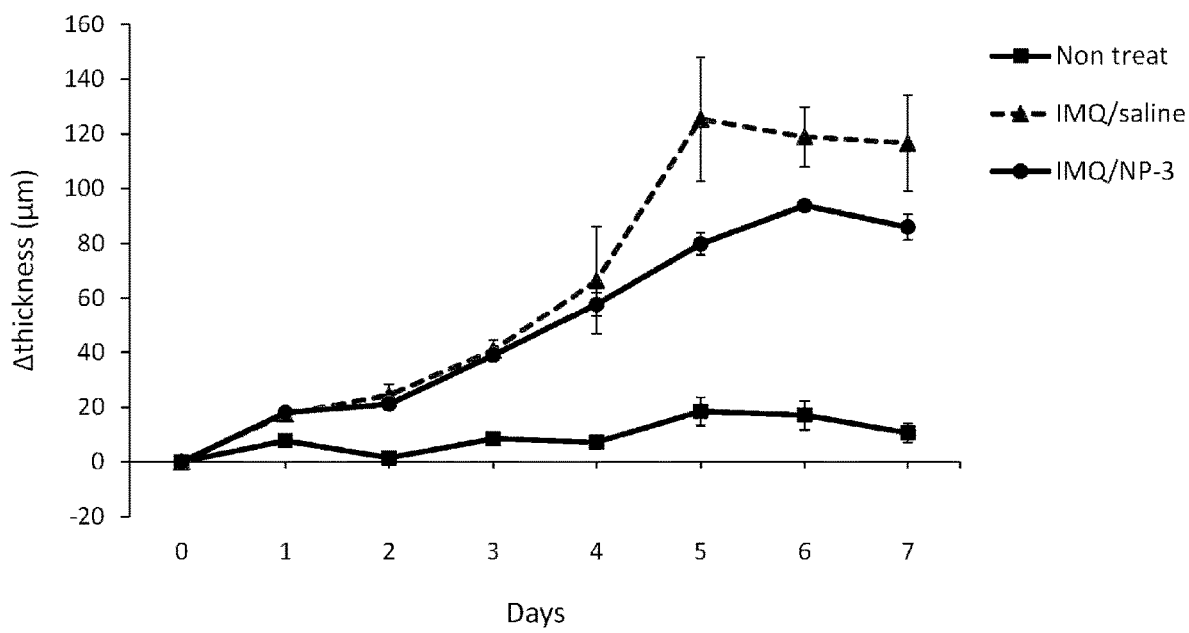
FIG. 9 is a graph showing changes in auricular thickness of mice. "Non treat" indicates normal mice, "IMQ/saline" indicates the control group, and "IMQ/NP-3" indicates the peptide NP-3 administration group. The horizontal axis indicates the number of days after the start of imiquimod application, and the vertical axis (Δthickness) shows difference (An−A0) between the auricular thickness before the start of imiquimod application (Day 0) (A0) and the auricular thickness at each day after the start of imiquimod application (An; n=1-7).

Changes in auricular thickness of mice during the test period are shown in FIG. 9 (see "Non treat" for normal mice, "IMQ/saline" for the control group, and "IMQ/NP-3" for the peptide NP-3 administration group). The auricular thickness of psoriasis model mice (the control group and peptide NP-3 administration group) increased with the passage of days. In the peptide NP-3 administration group, the increase in auricular thickness was suppressed as compared with the control group.

Symptoms of psoriasis vulgaris include erythema, thickening, scales/desquamation of the skin, which are caused by abnormalities in the immune system and the resulting inflammation, and hyperproliferation of keratinocytes. The mouse model used in this experiment is a model that causes psoriasis vulgaris-like symptoms (erythema and thickening) by applying imiquimod to the skin of the ear. As a result of the experiment, imiquimod-induced skin thickening was suppressed by administration of fragment peptide of the nuclear protein of the present application. This is thought to be the result of mobilization of mesenchymal stem cells into peripheral blood by the effect of the fragment peptide of the nuclear protein, and exhibition of the immune modulatory effect and inflammation-suppressing effect by the cells.

INDUSTRIAL APPLICABILITY

The nuclear proteins or fragment peptides thereof of the present application can be used as therapeutic agents for inflammatory diseases, autoimmune diseases, fibrotic diseases, and diseases accompanied by tissue damage/ischemia/necrosis.

The invention claimed is:

1. A method for mobilizing mesenchymal stem cells to peripheral blood, comprising administering to a subject an effective amount of a peptide consisting of the amino acid sequence that is at least 95% identical to the amino acid sequence selected from the group consisting of SEQ ID NOs: 35 to 56, wherein the peptide consists of a fragment of a nuclear protein and has activity of mobilizing mesenchymal stem cells to peripheral blood.

2. The method of claim 1, wherein the peptide consists of the amino acid sequence selected from the group consisting of SEQ ID NOs: 35 to 56.

3. The method of claim 1, wherein the peptide consists of the amino acid sequence of SEQ ID NO: 36.

4. The method of claim 1, wherein the peptide consists of the amino acid sequence of SEQ ID NO: 47.

5. A method for mobilizing mesenchymal stem cells to peripheral blood, comprising administering to a subject an effective amount of a peptide consisting of the amino acid sequence that is at least 95% identical to the amino acid sequence selected from the group consisting of SEQ ID NOs: 35 to 56; wherein the peptide consists of a fragment of a nuclear protein and has activity of mobilizing mesenchymal stem cells to peripheral blood; and wherein the nuclear protein is (1) basic transcription factor 3 (BTF3) protein, (2) suppressor of Ty 16 Homolog (SUPT16H) protein, (3) Y-box binding protein 1 (YBX1) protein, (4) nucleophosmin 1 (NPM1) protein, (5) proliferation-associated protein 2G4 (PA2G4) protein, (6) prefoldin subunit 5 (PFDN5) protein, (7) proteasome 26S subunit, ATPase 3 (PSMC3) protein, or (8) heterogeneous nuclear ribonucleoprotein K (HNRNPK) protein.

* * * * *

UNITED STATES PATENT AND TRADEMARK OFFICE
CERTIFICATE OF CORRECTION

PATENT NO. : 12,304,933 B2
APPLICATION NO. : 17/282872
DATED : May 20, 2025
INVENTOR(S) : Katsuto Tamai, Takashi Shimbo and Takehiko Yamazaki Page 1 of 1

It is certified that error appears in the above-identified patent and that said Letters Patent is hereby corrected as shown below:

On the Title Page

Item (22) "(22) PCT Filed: Apr. 10, 2019" should read --(22) PCT Filed: Oct. 4, 2019--.

Signed and Sealed this
Twenty-second Day of July, 2025

Coke Morgan Stewart
*Acting Director of the United States Patent and Trademark Office*

SEQUENCE LISTING

<160> NUMBER OF SEQ ID NOS: 130

<210> SEQ ID NO 1
<211> LENGTH: 204
<212> TYPE: PRT
<213> ORGANISM: Mus musculus

<400> SEQUENCE: 1

Met Arg Arg Thr Gly Ala Pro Thr Gln Ala Asp Ser Arg Gly Arg Gly
1               5                   10                  15

Arg Ala Arg Gly Gly Trp Pro Gly Ala Glu Ala Thr Pro Ser Leu Pro
                20                  25                  30

Leu Gly Gly Ser Arg Gly Arg Glu Ser Gln Met Lys Glu Thr Ile Met
            35                  40                  45

Asn Gln Glu Lys Leu Ala Lys Leu Gln Ala Gln Val Arg Ile Gly Gly
        50                  55                  60

Lys Gly Thr Ala Arg Arg Lys Lys Val Val His Arg Thr Ala Thr
65                  70                  75                  80

Ala Asp Asp Lys Lys Leu Gln Phe Ser Leu Lys Lys Leu Gly Val Asn
                85                  90                  95

Asn Ile Ser Gly Ile Glu Glu Val Asn Met Phe Thr Asn Gln Gly Thr
            100                 105                 110

Val Ile His Phe Asn Asn Pro Lys Val Gln Ala Ser Leu Ala Ala Asn
            115                 120                 125

Thr Phe Thr Ile Thr Gly His Ala Glu Thr Lys Gln Leu Thr Glu Met
130                 135                 140

Leu Pro Ser Ile Leu Asn Gln Leu Gly Ala Asp Ser Leu Thr Ser Leu
145                 150                 155                 160

Arg Arg Leu Ala Glu Ala Leu Pro Lys Gln Ser Val Asp Gly Lys Ala
                165                 170                 175

Pro Leu Ala Thr Gly Glu Asp Asp Asp Glu Val Pro Asp Leu Val
                180                 185                 190

Glu Asn Phe Asp Glu Ala Ser Lys Asn Glu Ala Asn
            195                 200

<210> SEQ ID NO 2
<211> LENGTH: 162
<212> TYPE: PRT
<213> ORGANISM: Mus musculus

<400> SEQUENCE: 2

Met Lys Glu Thr Ile Met Asn Gln Glu Lys Leu Ala Lys Leu Gln Ala
1               5                   10                  15

Gln Val Arg Ile Gly Gly Lys Gly Thr Ala Arg Arg Lys Lys Lys Val
                20                  25                  30

Val His Arg Thr Ala Thr Ala Asp Asp Lys Lys Leu Gln Phe Ser Leu
            35                  40                  45

Lys Lys Leu Gly Val Asn Asn Ile Ser Gly Ile Glu Glu Val Asn Met
50                  55                  60

Phe Thr Asn Gln Gly Thr Val Ile His Phe Asn Asn Pro Lys Val Gln
65                  70                  75                  80

Ala Ser Leu Ala Ala Asn Thr Phe Thr Ile Thr Gly His Ala Glu Thr
                85                  90                  95

Lys Gln Leu Thr Glu Met Leu Pro Ser Ile Leu Asn Gln Leu Gly Ala
            100                 105                 110

Asp Ser Leu Thr Ser Leu Arg Arg Leu Ala Glu Ala Leu Pro Lys Gln
            115                 120                 125

Ser Val Asp Gly Lys Ala Pro Leu Ala Thr Gly Glu Asp Asp Asp Asp
            130                 135                 140

Glu Val Pro Asp Leu Val Glu Asn Phe Asp Glu Ala Ser Lys Asn Glu
145                 150                 155                 160

Ala Asn

<210> SEQ ID NO 3
<211> LENGTH: 1047
<212> TYPE: PRT
<213> ORGANISM: Mus musculus

<400> SEQUENCE: 3

Met Ala Val Thr Leu Asp Lys Asp Ala Tyr Tyr Arg Arg Val Lys Arg
1               5                   10                  15

Leu Tyr Ser Asn Trp Arg Lys Gly Glu Asp Glu Tyr Ala Ser Ile Asp
            20                  25                  30

Ala Ile Val Val Ser Val Gly Val Asp Glu Glu Ile Val Tyr Ala Lys
            35                  40                  45

-continued

Ser Thr Ala Leu Gln Thr Trp Leu Phe Gly Tyr Glu Leu Thr Asp Thr
    50                  55                  60

Ile Met Val Phe Cys Asp Asp Lys Ile Ile Phe Met Ala Ser Lys Lys
65                  70                  75                  80

Lys Val Glu Phe Leu Lys Gln Ile Ala Asn Thr Lys Gly Asn Glu Asn
                85                  90                  95

Ala Asn Gly Ala Pro Ala Ile Thr Leu Leu Val Arg Glu Lys Asn Glu
            100                 105                 110

Ser Asn Lys Ser Ser Phe Asp Lys Met Ile Asp Ala Ile Lys Glu Ser
        115                 120                 125

Lys Ser Gly Lys Lys Ile Gly Val Phe Ser Lys Asp Lys Phe Pro Gly
    130                 135                 140

Glu Phe Met Lys Ser Trp Ser Asp Cys Leu Asn Lys Glu Gly Phe Asp
145                 150                 155                 160

Lys Val Asp Ile Ser Ala Val Val Ala Tyr Thr Ile Ala Val Lys Glu
                165                 170                 175

Asp Gly Glu Leu Asn Leu Met Lys Lys Ala Ala Ser Ile Thr Ser Glu
            180                 185                 190

Val Phe Asn Lys Phe Phe Lys Glu Arg Val Met Glu Ile Val Asp Ala
        195                 200                 205

Asp Glu Lys Val Arg His Ser Lys Leu Ala Glu Ser Val Glu Lys Ala
    210                 215                 220

Ile Glu Glu Lys Lys Tyr Leu Ala Gly Ala Asp Pro Ser Thr Val Glu
225                 230                 235                 240

Met Cys Tyr Pro Pro Ile Ile Gln Ser Gly Gly Asn Tyr Asn Leu Lys
                245                 250                 255

Phe Ser Val Val Ser Asp Lys Asn His Met His Phe Gly Ala Ile Thr
            260                 265                 270

Cys Ala Met Gly Ile Arg Phe Lys Ser Tyr Cys Ser Asn Leu Val Arg
        275                 280                 285

Thr Leu Met Val Asp Pro Thr Gln Glu Val Gln Glu Asn Tyr Asn Phe
    290                 295                 300

Leu Leu Gln Leu Gln Glu Leu Leu Lys Glu Leu Arg His Gly Val
305                 310                 315                 320

Lys Ile Cys Asp Val Tyr Asn Ser Val Met Asp Val Val Lys Lys Gln
                325                 330                 335

Lys Pro Glu Leu Leu Asn Lys Ile Thr Lys Asn Leu Gly Phe Gly Met
            340                 345                 350

Gly Ile Glu Phe Arg Glu Gly Ser Leu Val Ile Asn Ser Lys Asn Gln
        355                 360                 365

Tyr Lys Leu Lys Lys Gly Met Val Phe Ser Ile Asn Leu Gly Phe Ser
    370                 375                 380

Asp Leu Thr Asn Lys Glu Gly Lys Lys Pro Glu Glu Lys Thr Tyr Ala
385                 390                 395                 400

Leu Phe Ile Gly Asp Thr Val Leu Val Asp Glu Asp Gly Pro Ala Thr
                405                 410                 415

Ile Leu Thr Ser Val Lys Lys Lys Val Lys Asn Val Gly Ile Phe Leu
            420                 425                 430

Lys Asn Glu Asp Asp Glu Glu Glu Glu Lys Asp Glu Ala Glu
        435                 440                 445

Asp Leu Leu Gly Arg Gly Ser Arg Ala Ala Leu Leu Thr Glu Arg Thr
    450                 455                 460

```
Arg Asn Glu Met Thr Ala Glu Glu Lys Arg Arg Ala His Gln Lys Glu
465                 470                 475                 480

Leu Ala Ala Gln Leu Asn Glu Glu Ala Lys Arg Arg Leu Thr Glu Gln
                485                 490                 495

Lys Gly Glu Gln Gln Ile Gln Lys Ala Arg Lys Ser Asn Val Ser Tyr
                500                 505                 510

Lys Asn Pro Ser Leu Met Pro Lys Glu Pro His Ile Arg Glu Met Lys
                515                 520                 525

Ile Tyr Ile Asp Lys Lys Tyr Glu Thr Val Ile Met Pro Val Phe Gly
530                 535                 540

Ile Ala Thr Pro Phe His Ile Ala Thr Ile Lys Asn Ile Ser Met Ser
545                 550                 555                 560

Val Glu Gly Asp Tyr Thr Tyr Leu Arg Ile Asn Phe Tyr Cys Pro Gly
                565                 570                 575

Ser Ala Leu Gly Arg Asn Glu Gly Asn Ile Phe Pro Asn Pro Glu Ala
                580                 585                 590

Thr Phe Val Lys Glu Ile Thr Tyr Arg Ala Ser Asn Met Lys Ala Pro
                595                 600                 605

Gly Glu Gln Thr Val Pro Ala Leu Asn Leu Gln Asn Ala Phe Arg Ile
610                 615                 620

Ile Lys Glu Val Gln Lys Arg Tyr Lys Thr Arg Glu Ala Glu Lys
625                 630                 635                 640

Glu Lys Glu Gly Ile Val Lys Gln Asp Ser Leu Val Ile Asn Leu Asn
                645                 650                 655

Arg Ser Asn Pro Lys Leu Lys Asp Leu Tyr Ile Arg Pro Asn Ile Ala
                660                 665                 670

Gln Lys Arg Met Gln Gly Ser Leu Glu Ala His Val Asn Gly Phe Arg
                675                 680                 685

Phe Thr Ser Val Arg Gly Asp Lys Val Asp Ile Leu Tyr Asn Asn Ile
                690                 695                 700

Lys His Ala Leu Phe Gln Pro Cys Asp Gly Glu Met Ile Ile Val Leu
705                 710                 715                 720

His Phe His Leu Lys Asn Ala Val Met Phe Gly Lys Lys Arg His Thr
                725                 730                 735

Asp Val Gln Phe Tyr Thr Glu Val Gly Glu Ile Thr Thr Asp Leu Gly
                740                 745                 750

Lys His Gln His Met His Asp Arg Asp Leu Tyr Ala Glu Gln Met
                755                 760                 765

Glu Arg Glu Met Arg His Lys Leu Lys Thr Ala Phe Lys Asn Phe Ile
                770                 775                 780

Glu Lys Val Glu Ala Leu Thr Lys Glu Glu Leu Glu Phe Glu Val Pro
785                 790                 795                 800

Phe Arg Asp Leu Gly Phe Asn Gly Ala Pro Tyr Arg Ser Thr Cys Leu
                805                 810                 815

Leu Gln Pro Thr Ser Ser Ala Leu Val Asn Ala Thr Glu Trp Pro Pro
                820                 825                 830

Phe Val Val Thr Leu Asp Glu Val Glu Leu Ile His Phe Glu Arg Val
                835                 840                 845

Gln Phe His Leu Lys Asn Phe Asp Met Val Ile Val Tyr Lys Asp Tyr
                850                 855                 860

Ser Lys Lys Val Thr Met Ile Asn Ala Ile Pro Val Ala Ser Leu Asp
865                 870                 875                 880
```

-continued

Pro Ile Lys Glu Trp Leu Asn Ser Cys Asp Leu Lys Tyr Thr Glu Gly
                885                 890                 895

Val Gln Ser Leu Asn Trp Thr Lys Ile Met Lys Thr Ile Val Asp Asp
            900                 905                 910

Pro Glu Gly Phe Phe Glu Gln Gly Gly Trp Ser Phe Leu Glu Pro Glu
            915                 920                 925

Gly Glu Gly Ser Asp Ala Glu Asp Gly Asp Ser Glu Ser Glu Ile Glu
            930                 935                 940

Asp Glu Thr Phe Asn Pro Ser Glu Asp Tyr Glu Glu Glu Glu Glu Glu
945                 950                 955                 960

Asp Ser Asp Glu Asp Tyr Ser Ser Glu Ala Glu Glu Ser Asp Tyr Ser
            965                 970                 975

Lys Glu Ser Leu Gly Ser Glu Glu Ser Gly Lys Asp Trp Asp Glu
            980                 985                 990

Leu Glu Glu Glu Ala Arg Lys Ala Asp Arg Glu Ser Arg Tyr Glu Glu
            995                 1000                1005

Glu Glu Glu Gln Ser Arg Ser Met Ser Arg Lys Arg Lys Ala Ser
        1010                1015                1020

Val His Ser Ser Gly Arg Gly Ser Asn Arg Gly Ser Arg His Ser
        1025                1030                1035

Ser Ala Pro Pro Lys Lys Lys Arg Lys
        1040                1045

<210> SEQ ID NO 4
<211> LENGTH: 322
<212> TYPE: PRT
<213> ORGANISM: Mus musculus

<400> SEQUENCE: 4

Met Ser Ser Glu Ala Glu Thr Gln Gln Pro Pro Ala Ala Pro Ala Ala
1               5                   10                  15

Ala Leu Ser Ala Ala Asp Thr Lys Pro Gly Ser Thr Gly Ser Gly Ala
            20                  25                  30

Gly Ser Gly Gly Pro Gly Gly Leu Thr Ser Ala Ala Pro Ala Gly Gly
        35                  40                  45

Asp Lys Lys Val Ile Ala Thr Lys Val Leu Gly Thr Val Lys Trp Phe
50                  55                  60

Asn Val Arg Asn Gly Tyr Gly Phe Ile Asn Arg Asn Asp Thr Lys Glu
65                  70                  75                  80

Asp Val Phe Val His Gln Thr Ala Ile Lys Lys Asn Asn Pro Arg Lys
            85                  90                  95

Tyr Leu Arg Ser Val Gly Asp Gly Glu Thr Val Glu Phe Asp Val Val
            100                 105                 110

Glu Gly Glu Lys Gly Ala Glu Ala Ala Asn Val Thr Gly Pro Gly Gly
            115                 120                 125

Val Pro Val Gln Gly Ser Lys Tyr Ala Ala Asp Arg Asn His Tyr Arg
        130                 135                 140

Arg Tyr Pro Arg Arg Arg Gly Pro Pro Arg Asn Tyr Gln Gln Asn Tyr
145                 150                 155                 160

Gln Asn Ser Glu Ser Gly Glu Lys Asn Glu Gly Ser Glu Ser Ala Pro
            165                 170                 175

Glu Gly Gln Ala Gln Gln Arg Arg Pro Tyr Arg Arg Arg Phe Pro
            180                 185                 190

Pro Tyr Tyr Met Arg Arg Pro Tyr Ala Arg Arg Pro Gln Tyr Ser Asn
            195                 200                 205

-continued

Pro Pro Val Gln Gly Glu Val Met Glu Gly Ala Asp Asn Gln Gly Ala
    210                 215                 220

Gly Glu Gln Gly Arg Pro Val Arg Gln Asn Met Tyr Arg Gly Tyr Arg
225                 230                 235                 240

Pro Arg Phe Arg Arg Gly Pro Pro Arg Gln Arg Gln Pro Arg Glu Asp
                245                 250                 255

Gly Asn Glu Glu Asp Lys Glu Asn Gln Gly Asp Glu Thr Gln Gly Gln
            260                 265                 270

Gln Pro Pro Gln Arg Arg Tyr Arg Arg Asn Phe Asn Tyr Arg Arg Arg
        275                 280                 285

Arg Pro Glu Asn Pro Lys Pro Gln Asp Gly Lys Glu Thr Lys Ala Ala
    290                 295                 300

Asp Pro Pro Ala Glu Asn Ser Ser Ala Pro Glu Ala Glu Gln Gly Gly
305                 310                 315                 320

Ala Glu

<210> SEQ ID NO 5
<211> LENGTH: 292
<212> TYPE: PRT
<213> ORGANISM: Mus musculus

<400> SEQUENCE: 5

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Asp Glu Glu Asp Val Lys Leu Leu Gly Met Ser Gly Lys Arg Ser Ala
    130                 135                 140

Pro Gly Gly Gly Asn Lys Val Pro Gln Lys Lys Val Lys Leu Asp Glu
145                 150                 155                 160

Asp Asp Glu Asp Asp Asp Glu Asp Asp Glu Asp Asp Glu Asp Asp Asp
                165                 170                 175

Asp Asp Asp Phe Asp Glu Glu Glu Thr Glu Glu Lys Val Pro Val Lys
            180                 185                 190

Lys Ser Val Arg Asp Thr Pro Ala Lys Asn Ala Gln Lys Ser Asn Gln
        195                 200                 205

Asn Gly Lys Asp Leu Lys Pro Ser Thr Pro Arg Ser Lys Gly Gln Glu
    210                 215                 220

Ser Phe Lys Lys Gln Glu Lys Thr Pro Lys Thr Pro Lys Gly Pro Ser
225                 230                 235                 240

Ser Val Glu Asp Ile Lys Ala Lys Met Gln Ala Ser Ile Glu Lys Gly
                245                 250                 255

```
Gly Ser Leu Pro Lys Val Glu Ala Lys Phe Ile Asn Tyr Val Lys Asn
            260                 265                 270

Cys Phe Arg Met Thr Asp Gln Glu Ala Ile Gln Asp Leu Trp Gln Trp
                275                 280                 285

Arg Lys Ser Leu
        290

<210> SEQ ID NO 6
<211> LENGTH: 279
<212> TYPE: PRT
<213> ORGANISM: Mus musculus

<400> SEQUENCE: 6

Met Glu Asp Ser Met Asp Met Asp Met Ser Pro Leu Arg Pro Gln Asn
1               5                   10                  15

Tyr Leu Phe Val Asp Asn Asp Glu Asn Glu His Gln Leu Ser Leu Arg
            20                  25                  30

Thr Val Ser Leu Gly Ala Gly Ala Lys Asp Glu Leu His Ile Val Glu
        35                  40                  45

Ala Glu Ala Met Asn Tyr Glu Gly Ser Pro Ile Lys Val Thr Leu Ala
    50                  55                  60

Thr Leu Lys Met Ser Val Gln Pro Thr Val Ser Leu Gly Gly Phe Glu
65                  70                  75                  80

Ile Thr Pro Pro Val Leu Arg Leu Lys Cys Gly Ser Gly Pro Val
                85                  90                  95

His Ile Ser Gly Gln His Leu Val Ala Val Glu Glu Asp Ala Glu Ser
            100                 105                 110

Glu Asp Glu Asp Glu Asp Val Lys Leu Leu Gly Met Ser Gly Lys
        115                 120                 125

Arg Ser Ala Pro Gly Gly Asn Lys Val Pro Gln Lys Lys Val Lys
    130                 135                 140

Leu Asp Glu Asp Asp Glu Asp Asp Glu Asp Asp Glu Asp Asp Glu
145                 150                 155                 160

Asp Asp Asp Asp Asp Phe Asp Glu Glu Thr Glu Glu Lys Val
                165                 170                 175

Pro Val Lys Lys Ser Val Arg Asp Thr Pro Ala Lys Asn Ala Gln Lys
            180                 185                 190

Ser Asn Gln Asn Gly Lys Asp Leu Lys Pro Ser Thr Pro Arg Ser Lys
        195                 200                 205

Gly Gln Glu Ser Phe Lys Lys Gln Glu Lys Thr Pro Lys Thr Pro Lys
    210                 215                 220

Gly Pro Ser Ser Val Glu Asp Ile Lys Ala Lys Met Gln Ala Ser Ile
225                 230                 235                 240

Glu Lys Gly Gly Ser Leu Pro Lys Val Glu Ala Lys Phe Ile Asn Tyr
                245                 250                 255

Val Lys Asn Cys Phe Arg Met Thr Asp Gln Glu Ala Ile Gln Asp Leu
            260                 265                 270

Trp Gln Trp Arg Lys Ser Leu
        275

<210> SEQ ID NO 7
<211> LENGTH: 257
<212> TYPE: PRT
<213> ORGANISM: Mus musculus
```

<400> SEQUENCE: 7

```
Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
                35                  40                  45

Leu Gly Ala Gly Ala Lys Asp Glu Leu His Ile Val Glu Ala Glu Ala
        50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Asp Glu Glu Asp Val Lys Leu Leu Gly Met Ser Gly Lys Arg Ser Ala
    130                 135                 140

Pro Gly Gly Gly Asn Lys Val Pro Gln Lys Lys Val Lys Leu Asp Glu
145                 150                 155                 160

Asp Asp Glu Asp Asp Glu Asp Asp Glu Asp Glu Asp Asp Asp
                165                 170                 175

Asp Asp Asp Phe Asp Glu Glu Glu Thr Glu Glu Lys Val Pro Val Lys
            180                 185                 190

Lys Ser Val Arg Asp Thr Pro Ala Lys Asn Ala Gln Lys Ser Asn Gln
            195                 200                 205

Asn Gly Lys Asp Leu Lys Pro Ser Thr Pro Arg Ser Lys Gly Gln Glu
        210                 215                 220

Ser Phe Lys Lys Gln Glu Lys Thr Pro Lys Thr Pro Lys Gly Pro Ser
225                 230                 235                 240

Ser Val Glu Asp Ile Lys Ala Lys Met Gln Ala Ser Ile Glu Lys Ala
                245                 250                 255

His
```

<210> SEQ ID NO 8
<211> LENGTH: 394
<212> TYPE: PRT
<213> ORGANISM: Mus musculus

<400> SEQUENCE: 8

```
Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
            20                  25                  30

Arg Ser Leu Val Glu Ala Ser Ser Gly Val Ser Val Leu Ser Leu
            35                  40                  45

Cys Glu Lys Gly Asp Ala Met Ile Met Glu Thr Gly Lys Ile Phe
        50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
                85                  90                  95
```

-continued

```
Asp Tyr Ile Leu Lys Glu Gly Asp Leu Val Lys Ile Asp Leu Gly Val
                100                 105                 110

His Val Asp Gly Phe Ile Ala Asn Val Ala His Thr Phe Val Ile Gly
            115                 120                 125

Val Ala Gln Gly Thr Gln Val Thr Gly Arg Lys Ala Asp Val Ile Lys
        130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
            180                 185                 190

His Val Ile Asp Gly Glu Lys Thr Ile Ile Gln Asn Pro Thr Asp Gln
        195                 200                 205

Gln Lys Lys Asp His Glu Lys Ala Glu Phe Glu Val His Glu Val Tyr
    210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
        275                 280                 285

Ala Arg Met Gly Val Val Glu Cys Ala Lys His Glu Leu Leu Gln Pro
    290                 295                 300

Phe Asn Val Leu Tyr Glu Lys Glu Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ser Ala Ser Arg Lys Thr Gln Lys
        355                 360                 365

Lys Lys Lys Lys Lys Ala Ser Lys Thr Val Glu Asn Ala Thr Ser Gly
    370                 375                 380

Glu Thr Leu Glu Glu Asn Gly Ala Gly Asp
385                 390

<210> SEQ ID NO 9
<211> LENGTH: 154
<212> TYPE: PRT
<213> ORGANISM: Mus musculus

<400> SEQUENCE: 9

Met Ala Gln Ser Ile Asn Ile Thr Glu Leu Asn Leu Pro Gln Leu Glu
1               5                   10                  15

Met Leu Lys Asn Gln Leu Asp Gln Glu Val Glu Phe Leu Ser Thr Ser
            20                  25                  30

Ile Ala Gln Leu Lys Val Val Gln Thr Lys Tyr Val Glu Ala Lys Asp
        35                  40                  45

Cys Leu Asn Val Leu Asn Lys Ser Asn Glu Gly Lys Glu Leu Leu Val
    50                  55                  60

Pro Leu Thr Ser Ser Met Tyr Val Pro Gly Lys Leu His Asp Val Glu
65                  70                  75                  80
```

```
His Val Leu Ile Asp Val Gly Thr Gly Tyr Tyr Val Glu Lys Thr Ala
                85                  90                  95

Glu Asp Ala Lys Asp Phe Phe Lys Arg Lys Ile Asp Phe Leu Thr Lys
            100                 105                 110

Gln Met Glu Lys Ile Gln Pro Ala Leu Gln Glu Lys His Ala Met Lys
        115                 120                 125

Gln Ala Val Met Glu Met Met Ser Gln Lys Ile Gln Gln Leu Thr Ala
130                 135                 140

Leu Gly Ala Ala Gln Ala Thr Val Lys Ala
145                 150

<210> SEQ ID NO 10
<211> LENGTH: 442
<212> TYPE: PRT
<213> ORGANISM: Mus musculus

<400> SEQUENCE: 10

Met Gln Glu Met Asn Leu Leu Pro Thr Pro Glu Ser Pro Val Thr Arg
1               5                   10                  15

Gln Glu Lys Met Ala Thr Val Trp Asp Glu Ala Glu Gln Asp Gly Ile
            20                  25                  30

Gly Glu Glu Val Leu Lys Met Ser Thr Glu Glu Ile Val Gln Arg Thr
        35                  40                  45

Arg Leu Leu Asp Ser Glu Ile Lys Ile Met Lys Ser Glu Val Leu Arg
    50                  55                  60

Val Thr His Glu Leu Gln Ala Met Lys Asp Lys Ile Lys Glu Asn Ser
65                  70                  75                  80

Glu Lys Ile Lys Val Asn Lys Thr Leu Pro Tyr Leu Val Ser Asn Val
                85                  90                  95

Ile Glu Leu Leu Asp Val Asp Pro Asn Asp Gln Glu Glu Asp Gly Ala
            100                 105                 110

Asn Ile Asp Leu Asp Ser Gln Arg Lys Gly Lys Cys Ala Val Ile Lys
        115                 120                 125

Thr Ser Thr Arg Gln Thr Tyr Phe Leu Pro Val Ile Gly Leu Val Asp
    130                 135                 140

Ala Glu Lys Leu Lys Pro Gly Asp Leu Val Gly Val Asn Lys Asp Ser
145                 150                 155                 160

Tyr Leu Ile Leu Glu Thr Leu Pro Thr Glu Tyr Asp Ser Arg Val Lys
                165                 170                 175

Ala Met Glu Val Asp Glu Arg Pro Thr Glu Gln Tyr Ser Asp Ile Gly
            180                 185                 190

Gly Leu Asp Lys Gln Ile Gln Glu Leu Val Glu Ala Ile Val Leu Pro
        195                 200                 205

Met Asn His Lys Glu Lys Phe Glu Asn Leu Gly Ile Gln Pro Pro Lys
    210                 215                 220

Gly Val Leu Met Tyr Gly Pro Pro Gly Thr Gly Lys Thr Leu Leu Ala
225                 230                 235                 240

Arg Ala Cys Ala Ala Gln Thr Lys Ala Thr Phe Leu Lys Leu Ala Gly
                245                 250                 255

Pro Gln Leu Val Gln Met Phe Ile Gly Asp Gly Ala Lys Leu Val Arg
            260                 265                 270

Asp Ala Phe Ala Leu Ala Lys Glu Lys Ala Pro Ser Ile Ile Phe Ile
        275                 280                 285
```

```
Asp Glu Leu Asp Ala Ile Gly Thr Lys Arg Phe Asp Ser Glu Lys Ala
        290                 295                 300

Gly Asp Arg Glu Val Gln Arg Thr Met Leu Glu Leu Leu Asn Gln Leu
305                 310                 315                 320

Asp Gly Phe Gln Pro Asn Thr Gln Val Lys Val Ile Ala Ala Thr Asn
                    325                 330                 335

Arg Val Asp Ile Leu Asp Pro Ala Leu Leu Arg Ser Gly Arg Leu Asp
                340                 345                 350

Arg Lys Ile Glu Phe Pro Met Pro Asn Glu Glu Ala Arg Ala Arg Ile
            355                 360                 365

Met Gln Ile His Ser Arg Lys Met Asn Val Ser Pro Asp Val Asn Tyr
    370                 375                 380

Glu Glu Leu Ala Arg Cys Thr Asp Asp Phe Asn Gly Ala Gln Cys Lys
385                 390                 395                 400

Ala Val Cys Val Glu Ala Gly Met Ile Ala Leu Arg Arg Gly Ala Thr
                405                 410                 415

Glu Leu Thr His Glu Asp Tyr Met Glu Gly Ile Leu Glu Val Gln Ala
                420                 425                 430

Lys Lys Lys Ala Asn Leu Gln Tyr Tyr Ala
            435                 440

<210> SEQ ID NO 11
<211> LENGTH: 464
<212> TYPE: PRT
<213> ORGANISM: Mus musculus

<400> SEQUENCE: 11

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125

Ala Val Glu Cys Leu Asn Tyr Gln His Tyr Lys Gly Ser Asp Phe Asp
    130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205
```

```
Ile Leu Asp Leu Ile Ser Glu Ser Pro Ile Lys Gly Arg Ala Gln Pro
        210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Asp Met Ser Pro Arg Arg Gly
        275                 280                 285

Pro Pro Pro Pro Pro Gly Arg Gly Arg Gly Gly Ser Arg Ala
290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
        355                 360                 365

Tyr Asp Tyr Ser Tyr Ala Gly Gly Arg Gly Ser Tyr Gly Asp Leu Gly
370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
                405                 410                 415

Ser Gly Ala Ser Ile Lys Ile Asp Glu Pro Leu Glu Gly Ser Glu Asp
            420                 425                 430

Arg Ile Ile Thr Ile Thr Gly Thr Gln Asp Gln Ile Gln Asn Ala Gln
        435                 440                 445

Tyr Leu Leu Gln Asn Ser Val Lys Gln Tyr Ala Asp Val Glu Gly Phe
450                 455                 460

<210> SEQ ID NO 12
<211> LENGTH: 463
<212> TYPE: PRT
<213> ORGANISM: Mus musculus

<400> SEQUENCE: 12

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110
```

Gln Leu Pro Ser Pro Thr Ala Thr Ser Gln Leu Pro Leu Glu Ser Asp
            115                 120                 125

Ala Val Glu Cys Leu Asn Tyr Gln His Tyr Lys Gly Ser Asp Phe Asp
        130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205

Ile Leu Asp Leu Ile Ser Glu Ser Pro Ile Lys Gly Arg Ala Gln Pro
210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Arg Pro
            260                 265                 270

Met Pro Pro Ser Arg Arg Asp Tyr Asp Asp Met Ser Pro Arg Arg Gly
            275                 280                 285

Pro Pro Pro Pro Pro Gly Arg Gly Gly Arg Gly Ser Arg Ala
        290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
            325                 330                 335

Val Gly Phe Ser Ala Asp Glu Thr Trp Asp Ser Ala Ile Asp Thr Trp
                340                 345                 350

Ser Pro Ser Glu Trp Gln Met Ala Tyr Glu Pro Gln Gly Gly Ser Gly
            355                 360                 365

Tyr Asp Tyr Ser Tyr Ala Gly Gly Arg Gly Ser Tyr Gly Asp Leu Gly
370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
                405                 410                 415

Ser Gly Ala Ser Ile Lys Ile Asp Glu Pro Leu Glu Gly Ser Glu Asp
            420                 425                 430

Arg Ile Ile Thr Ile Thr Gly Thr Gln Asp Gln Ile Gln Asn Ala Gln
        435                 440                 445

Tyr Leu Leu Gln Asn Ser Val Lys Gln Tyr Ser Gly Lys Phe Phe
450                 455                 460

<210> SEQ ID NO 13
<211> LENGTH: 440
<212> TYPE: PRT
<213> ORGANISM: Mus musculus

<400> SEQUENCE: 13

Met Glu Thr Glu Gln Pro Glu Glu Thr Phe Pro Asn Thr Glu Thr Asn
1               5                   10                  15

```
Gly Glu Phe Gly Lys Arg Pro Ala Glu Asp Met Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Tyr Gln
            100                 105                 110

His Tyr Lys Gly Ser Asp Phe Asp Cys Glu Leu Arg Leu Leu Ile His
        115                 120                 125

Gln Ser Leu Ala Gly Gly Ile Ile Gly Val Lys Gly Ala Lys Ile Lys
130                 135                 140

Glu Leu Arg Glu Asn Thr Gln Thr Thr Ile Lys Leu Phe Gln Glu Cys
145                 150                 155                 160

Cys Pro His Ser Thr Asp Arg Val Val Leu Ile Gly Gly Lys Pro Asp
                165                 170                 175

Arg Val Val Glu Cys Ile Lys Ile Ile Leu Asp Leu Ile Ser Glu Ser
            180                 185                 190

Pro Ile Lys Gly Arg Ala Gln Pro Tyr Asp Pro Asn Phe Tyr Asp Glu
        195                 200                 205

Thr Tyr Asp Tyr Gly Gly Phe Thr Met Met Phe Asp Asp Arg Arg Gly
    210                 215                 220

Arg Pro Val Gly Phe Pro Met Arg Gly Arg Gly Gly Phe Asp Arg Met
225                 230                 235                 240

Pro Pro Gly Arg Gly Gly Arg Pro Met Pro Pro Ser Arg Arg Asp Tyr
                245                 250                 255

Asp Asp Met Ser Pro Arg Arg Gly Pro Pro Pro Pro Pro Gly Arg
            260                 265                 270

Gly Gly Arg Gly Gly Ser Arg Ala Arg Asn Leu Pro Leu Pro Pro
        275                 280                 285

Pro Pro Pro Arg Gly Gly Asp Leu Met Ala Tyr Asp Arg Arg Gly Arg
    290                 295                 300

Pro Gly Asp Arg Tyr Asp Gly Met Val Gly Phe Ser Ala Asp Glu Thr
305                 310                 315                 320

Trp Asp Ser Ala Ile Asp Thr Trp Ser Pro Ser Glu Trp Gln Met Ala
                325                 330                 335

Tyr Glu Pro Gln Gly Gly Ser Gly Tyr Asp Tyr Ser Tyr Ala Gly Gly
            340                 345                 350

Arg Gly Ser Tyr Gly Asp Leu Gly Gly Pro Ile Ile Thr Thr Gln Val
        355                 360                 365

Thr Ile Pro Lys Asp Leu Ala Gly Ser Ile Gly Lys Gly Gly Gln
    370                 375                 380

Arg Ile Lys Gln Ile Arg His Glu Ser Gly Ala Ser Ile Lys Ile Asp
385                 390                 395                 400

Glu Pro Leu Glu Gly Ser Glu Asp Arg Ile Ile Thr Ile Thr Gly Thr
                405                 410                 415

Gln Asp Gln Ile Gln Asn Ala Gln Tyr Leu Leu Gln Asn Ser Val Lys
            420                 425                 430
```

```
Gln Tyr Ala Asp Val Glu Gly Phe
        435                 440

<210> SEQ ID NO 14
<211> LENGTH: 439
<212> TYPE: PRT
<213> ORGANISM: Mus musculus

<400> SEQUENCE: 14

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Tyr Gln
            100                 105                 110

His Tyr Lys Gly Ser Asp Phe Asp Cys Glu Leu Arg Leu Leu Ile His
        115                 120                 125

Gln Ser Leu Ala Gly Gly Ile Ile Gly Val Lys Gly Ala Lys Ile Lys
    130                 135                 140

Glu Leu Arg Glu Asn Thr Gln Thr Thr Ile Lys Leu Phe Gln Glu Cys
145                 150                 155                 160

Cys Pro His Ser Thr Asp Arg Val Val Leu Ile Gly Gly Lys Pro Asp
                165                 170                 175

Arg Val Val Glu Cys Ile Lys Ile Ile Leu Asp Leu Ile Ser Glu Ser
            180                 185                 190

Pro Ile Lys Gly Arg Ala Gln Pro Tyr Asp Pro Asn Phe Tyr Asp Glu
        195                 200                 205

Thr Tyr Asp Tyr Gly Gly Phe Thr Met Met Phe Asp Asp Arg Arg Gly
    210                 215                 220

Arg Pro Val Gly Phe Pro Met Arg Gly Arg Gly Gly Phe Asp Arg Met
225                 230                 235                 240

Pro Pro Gly Arg Gly Gly Arg Pro Met Pro Pro Ser Arg Arg Asp Tyr
                245                 250                 255

Asp Asp Met Ser Pro Arg Arg Gly Pro Pro Pro Pro Pro Gly Arg
            260                 265                 270

Gly Gly Arg Gly Gly Ser Arg Ala Arg Asn Leu Pro Leu Pro Pro Pro
        275                 280                 285

Pro Pro Pro Arg Gly Gly Asp Leu Met Ala Tyr Asp Arg Arg Gly Arg
    290                 295                 300

Pro Gly Asp Arg Tyr Asp Gly Met Val Gly Phe Ser Ala Asp Glu Thr
305                 310                 315                 320

Trp Asp Ser Ala Ile Asp Thr Trp Ser Pro Ser Glu Trp Gln Met Ala
                325                 330                 335

Tyr Glu Pro Gln Gly Gly Ser Gly Tyr Asp Tyr Ser Tyr Ala Gly Gly
            340                 345                 350

Arg Gly Ser Tyr Gly Asp Leu Gly Gly Pro Ile Ile Thr Thr Gln Val
        355                 360                 365
```

```
Thr Ile Pro Lys Asp Leu Ala Gly Ser Ile Ile Gly Lys Gly Gly Gln
    370                 375                 380

Arg Ile Lys Gln Ile Arg His Glu Ser Gly Ala Ser Ile Lys Ile Asp
385                 390                 395                 400

Glu Pro Leu Glu Gly Ser Glu Asp Arg Ile Ile Thr Ile Thr Gly Thr
                405                 410                 415

Gln Asp Gln Ile Gln Asn Ala Gln Tyr Leu Leu Gln Asn Ser Val Lys
                420                 425                 430

Gln Tyr Ser Gly Lys Phe Phe
                435

<210> SEQ ID NO 15
<211> LENGTH: 459
<212> TYPE: PRT
<213> ORGANISM: Mus musculus

<400> SEQUENCE: 15

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
                20                  25                  30

Phe Lys Arg Ser Arg Asn Thr Asp Glu Met Val Glu Leu Arg Ile Leu
            35                  40                  45

Leu Gln Ser Lys Asn Ala Gly Ala Val Ile Gly Lys Gly Gly Lys Asn
        50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
                100                 105                 110

Gln Leu Pro Ser Pro Thr Ala Thr Ser Gln Leu Pro Leu Glu Ser Asp
            115                 120                 125

Ala Val Glu Cys Leu Asn Tyr Gln His Tyr Lys Gly Ser Asp Phe Asp
        130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205

Ile Leu Asp Leu Ile Ser Glu Ser Pro Ile Lys Gly Arg Ala Gln Pro
210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Asp Met Ser Pro Arg Arg Gly
        275                 280                 285
```

```
Pro Pro Pro Pro Pro Gly Arg Gly Gly Arg Gly Ser Arg Ala
    290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
            355                 360                 365

Tyr Gly Gly Arg Gly Ser Tyr Gly Asp Leu Gly Gly Pro Ile Ile Thr
370                 375                 380

Thr Gln Val Thr Ile Pro Lys Asp Leu Ala Gly Ser Ile Ile Gly Lys
385                 390                 395                 400

Gly Gly Gln Arg Ile Lys Gln Ile Arg His Glu Ser Gly Ala Ser Ile
                405                 410                 415

Lys Ile Asp Glu Pro Leu Glu Gly Ser Glu Asp Arg Ile Ile Thr Ile
                420                 425                 430

Thr Gly Thr Gln Asp Gln Ile Gln Asn Ala Gln Tyr Leu Leu Gln Asn
            435                 440                 445

Ser Val Lys Gln Tyr Ala Asp Val Glu Gly Phe
    450                 455
```

<210> SEQ ID NO 16
<211> LENGTH: 458
<212> TYPE: PRT
<213> ORGANISM: Mus musculus

<400> SEQUENCE: 16

```
Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
                20                  25                  30

Phe Lys Arg Ser Arg Asn Thr Asp Glu Met Val Glu Leu Arg Ile Leu
            35                  40                  45

Leu Gln Ser Lys Asn Ala Gly Ala Val Ile Gly Lys Gly Gly Lys Asn
        50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125

Ala Val Glu Cys Leu Asn Tyr Gln His Tyr Lys Gly Ser Asp Phe Asp
130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190
```

-continued

Val Leu Ile Gly Gly Lys Pro Asp Arg Val Glu Cys Ile Lys Ile
        195                 200                 205

Ile Leu Asp Leu Ile Ser Glu Ser Pro Ile Lys Gly Arg Ala Gln Pro
210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Asp Met Ser Pro Arg Arg Gly
        275                 280                 285

Pro Pro Pro Pro Pro Pro Gly Arg Gly Gly Arg Gly Gly Ser Arg Ala
        290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
        355                 360                 365

Tyr Gly Gly Arg Gly Ser Tyr Gly Asp Leu Gly Gly Pro Ile Ile Thr
        370                 375                 380

Thr Gln Val Thr Ile Pro Lys Asp Leu Ala Gly Ser Ile Ile Gly Lys
385                 390                 395                 400

Gly Gly Gln Arg Ile Lys Gln Ile Arg His Glu Ser Gly Ala Ser Ile
                405                 410                 415

Lys Ile Asp Glu Pro Leu Glu Gly Ser Glu Asp Arg Ile Ile Thr Ile
                420                 425                 430

Thr Gly Thr Gln Asp Gln Ile Gln Asn Ala Gln Tyr Leu Leu Gln Asn
            435                 440                 445

Ser Val Lys Gln Tyr Ser Gly Lys Phe Phe
        450                 455

<210> SEQ ID NO 17
<211> LENGTH: 206
<212> TYPE: PRT
<213> ORGANISM: Homo sapiens

<400> SEQUENCE: 17

Met Arg Arg Thr Gly Ala Pro Ala Gln Ala Asp Ser Arg Gly Arg Gly
1               5                   10                  15

Arg Ala Arg Gly Gly Cys Pro Gly Gly Glu Ala Thr Leu Ser Gln Pro
            20                  25                  30

Pro Pro Arg Gly Gly Thr Arg Gly Gln Glu Pro Gln Met Lys Glu Thr
        35                  40                  45

Ile Met Asn Gln Glu Lys Leu Ala Lys Leu Gln Ala Gln Val Arg Ile
    50                  55                  60

Gly Gly Lys Gly Thr Ala Arg Arg Lys Lys Val Val His Arg Thr
65                  70                  75                  80

Ala Thr Ala Asp Asp Lys Lys Leu Gln Phe Ser Leu Lys Lys Leu Gly
                85                  90                  95

-continued

Val Asn Asn Ile Ser Gly Ile Glu Glu Val Asn Met Phe Thr Asn Gln
            100                 105                 110

Gly Thr Val Ile His Phe Asn Pro Lys Val Gln Ala Ser Leu Ala
115                 120                 125

Ala Asn Thr Phe Thr Ile Thr Gly His Ala Glu Thr Lys Gln Leu Thr
130                 135                 140

Glu Met Leu Pro Ser Ile Leu Asn Gln Leu Gly Ala Asp Ser Leu Thr
145                 150                 155                 160

Ser Leu Arg Arg Leu Ala Glu Ala Leu Pro Lys Gln Ser Val Asp Gly
                165                 170                 175

Lys Ala Pro Leu Ala Thr Gly Glu Asp Asp Asp Glu Val Pro Asp
                180                 185                 190

Leu Val Glu Asn Phe Asp Glu Ala Ser Lys Asn Glu Ala Asn
                195                 200                 205

<210> SEQ ID NO 18
<211> LENGTH: 162
<212> TYPE: PRT
<213> ORGANISM: Homo sapiens

<400> SEQUENCE: 18

Met Lys Glu Thr Ile Met Asn Gln Glu Lys Leu Ala Lys Leu Gln Ala
1               5                   10                  15

Gln Val Arg Ile Gly Gly Lys Gly Thr Ala Arg Arg Lys Lys Lys Val
                20                  25                  30

Val His Arg Thr Ala Thr Ala Asp Asp Lys Lys Leu Gln Phe Ser Leu
            35                  40                  45

Lys Lys Leu Gly Val Asn Asn Ile Ser Gly Ile Glu Glu Val Asn Met
50                  55                  60

Phe Thr Asn Gln Gly Thr Val Ile His Phe Asn Asn Pro Lys Val Gln
65                  70                  75                  80

Ala Ser Leu Ala Ala Asn Thr Phe Thr Ile Thr Gly His Ala Glu Thr
                85                  90                  95

Lys Gln Leu Thr Glu Met Leu Pro Ser Ile Leu Asn Gln Leu Gly Ala
            100                 105                 110

Asp Ser Leu Thr Ser Leu Arg Arg Leu Ala Glu Ala Leu Pro Lys Gln
        115                 120                 125

Ser Val Asp Gly Lys Ala Pro Leu Ala Thr Gly Glu Asp Asp Asp
        130                 135                 140

Glu Val Pro Asp Leu Val Glu Asn Phe Asp Glu Ala Ser Lys Asn Glu
145                 150                 155                 160

Ala Asn

<210> SEQ ID NO 19
<211> LENGTH: 1047
<212> TYPE: PRT
<213> ORGANISM: Homo sapiens

<400> SEQUENCE: 19

Met Ala Val Thr Leu Asp Lys Asp Ala Tyr Tyr Arg Arg Val Lys Arg
1               5                   10                  15

Leu Tyr Ser Asn Trp Arg Lys Gly Glu Asp Glu Tyr Ala Asn Val Asp
                20                  25                  30

Ala Ile Val Val Ser Val Gly Val Asp Glu Glu Ile Val Tyr Ala Lys
            35                  40                  45

```
Ser Thr Ala Leu Gln Thr Trp Leu Phe Gly Tyr Glu Leu Thr Asp Thr
 50                  55                  60

Ile Met Val Phe Cys Asp Asp Lys Ile Ile Phe Met Ala Ser Lys Lys
 65                  70                  75                  80

Lys Val Glu Phe Leu Lys Gln Ile Ala Asn Thr Lys Gly Asn Glu Asn
                 85                  90                  95

Ala Asn Gly Ala Pro Ala Ile Thr Leu Leu Ile Arg Glu Lys Asn Glu
            100                 105                 110

Ser Asn Lys Ser Ser Phe Asp Lys Met Ile Glu Ala Ile Lys Glu Ser
            115                 120                 125

Lys Asn Gly Lys Lys Ile Gly Val Phe Ser Lys Asp Lys Phe Pro Gly
130                 135                 140

Glu Phe Met Lys Ser Trp Asn Asp Cys Leu Asn Lys Glu Gly Phe Asp
145                 150                 155                 160

Lys Ile Asp Ile Ser Ala Val Val Ala Tyr Thr Ile Ala Val Lys Glu
                165                 170                 175

Asp Gly Glu Leu Asn Leu Met Lys Lys Ala Ala Ser Ile Thr Ser Glu
            180                 185                 190

Val Phe Asn Lys Phe Phe Lys Glu Arg Val Met Glu Ile Val Asp Ala
            195                 200                 205

Asp Glu Lys Val Arg His Ser Lys Leu Ala Glu Ser Val Glu Lys Ala
210                 215                 220

Ile Glu Glu Lys Lys Tyr Leu Ala Gly Ala Asp Pro Ser Thr Val Glu
225                 230                 235                 240

Met Cys Tyr Pro Pro Ile Ile Gln Ser Gly Gly Asn Tyr Asn Leu Lys
                245                 250                 255

Phe Ser Val Val Ser Asp Lys Asn His Met His Phe Gly Ala Ile Thr
            260                 265                 270

Cys Ala Met Gly Ile Arg Phe Lys Ser Tyr Cys Ser Asn Leu Val Arg
            275                 280                 285

Thr Leu Met Val Asp Pro Ser Gln Glu Val Gln Glu Asn Tyr Asn Phe
290                 295                 300

Leu Leu Gln Leu Gln Glu Leu Leu Lys Glu Leu Arg His Gly Val
305                 310                 315                 320

Lys Ile Cys Asp Val Tyr Asn Ala Val Met Asp Val Val Lys Lys Gln
                325                 330                 335

Lys Pro Glu Leu Leu Asn Lys Ile Thr Lys Asn Leu Gly Phe Gly Met
            340                 345                 350

Gly Ile Glu Phe Arg Glu Gly Ser Leu Val Ile Asn Ser Lys Asn Gln
            355                 360                 365

Tyr Lys Leu Lys Lys Gly Met Val Phe Ser Ile Asn Leu Gly Phe Ser
370                 375                 380

Asp Leu Thr Asn Lys Glu Gly Lys Lys Pro Glu Glu Lys Thr Tyr Ala
385                 390                 395                 400

Leu Phe Ile Gly Asp Thr Val Leu Val Asp Glu Asp Gly Pro Ala Thr
                405                 410                 415

Val Leu Thr Ser Val Lys Lys Lys Val Lys Asn Val Gly Ile Phe Leu
            420                 425                 430

Lys Asn Glu Asp Glu Glu Glu Glu Glu Lys Asp Glu Ala Glu
            435                 440                 445

Asp Leu Leu Gly Arg Gly Ser Arg Ala Ala Leu Leu Thr Glu Arg Thr
450                 455                 460
```

-continued

```
Arg Asn Glu Met Thr Ala Glu Glu Lys Arg Arg Ala His Gln Lys Glu
465                 470                 475                 480

Leu Ala Ala Gln Leu Asn Glu Glu Ala Lys Arg Arg Leu Thr Glu Gln
            485                 490                 495

Lys Gly Glu Gln Gln Ile Gln Lys Ala Arg Lys Ser Asn Val Ser Tyr
        500                 505                 510

Lys Asn Pro Ser Leu Met Pro Lys Glu Pro His Ile Arg Glu Met Lys
    515                 520                 525

Ile Tyr Ile Asp Lys Lys Tyr Glu Thr Val Ile Met Pro Val Phe Gly
530                 535                 540

Ile Ala Thr Pro Phe His Ile Ala Thr Ile Lys Asn Ile Ser Met Ser
545                 550                 555                 560

Val Glu Gly Asp Tyr Thr Tyr Leu Arg Ile Asn Phe Tyr Cys Pro Gly
                565                 570                 575

Ser Ala Leu Gly Arg Asn Glu Gly Asn Ile Phe Pro Asn Pro Glu Ala
            580                 585                 590

Thr Phe Val Lys Glu Ile Thr Tyr Arg Ala Ser Asn Ile Lys Ala Pro
        595                 600                 605

Gly Glu Gln Thr Val Pro Ala Leu Asn Leu Gln Asn Ala Phe Arg Ile
610                 615                 620

Ile Lys Glu Val Gln Lys Arg Tyr Lys Thr Arg Glu Ala Glu Lys
625                 630                 635                 640

Glu Lys Glu Gly Ile Val Lys Gln Asp Ser Leu Val Ile Asn Leu Asn
                645                 650                 655

Arg Ser Asn Pro Lys Leu Lys Asp Leu Tyr Ile Arg Pro Asn Ile Ala
            660                 665                 670

Gln Lys Arg Met Gln Gly Ser Leu Glu Ala His Val Asn Gly Phe Arg
        675                 680                 685

Phe Thr Ser Val Arg Gly Asp Lys Val Asp Ile Leu Tyr Asn Asn Ile
690                 695                 700

Lys His Ala Leu Phe Gln Pro Cys Asp Gly Glu Met Ile Ile Val Leu
705                 710                 715                 720

His Phe His Leu Lys Asn Ala Ile Met Phe Gly Lys Lys Arg His Thr
                725                 730                 735

Asp Val Gln Phe Tyr Thr Glu Val Gly Glu Ile Thr Thr Asp Leu Gly
            740                 745                 750

Lys His Gln His Met His Asp Arg Asp Leu Tyr Ala Glu Gln Met
        755                 760                 765

Glu Arg Glu Met Arg His Lys Leu Lys Thr Ala Phe Lys Asn Phe Ile
770                 775                 780

Glu Lys Val Glu Ala Leu Thr Lys Glu Glu Leu Glu Phe Glu Val Pro
785                 790                 795                 800

Phe Arg Asp Leu Gly Phe Asn Gly Ala Pro Tyr Arg Ser Thr Cys Leu
                805                 810                 815

Leu Gln Pro Thr Ser Ser Ala Leu Val Asn Ala Thr Glu Trp Pro Pro
            820                 825                 830

Phe Val Val Thr Leu Asp Glu Val Glu Leu Ile His Phe Glu Arg Val
        835                 840                 845

Gln Phe His Leu Lys Asn Phe Asp Met Val Ile Val Tyr Lys Asp Tyr
850                 855                 860

Ser Lys Lys Val Thr Met Ile Asn Ala Ile Pro Val Ala Ser Leu Asp
865                 870                 875                 880
```

-continued

```
Pro Ile Lys Glu Trp Leu Asn Ser Cys Asp Leu Lys Tyr Thr Glu Gly
                885                 890                 895

Val Gln Ser Leu Asn Trp Thr Lys Ile Met Lys Thr Ile Val Asp Asp
            900                 905                 910

Pro Glu Gly Phe Phe Glu Gln Gly Gly Trp Ser Phe Leu Glu Pro Glu
            915                 920                 925

Gly Glu Gly Ser Asp Ala Glu Gly Asp Ser Glu Ser Glu Ile Glu
            930                 935                 940

Asp Glu Thr Phe Asn Pro Ser Glu Asp Tyr Glu Glu Glu Glu
945                 950                 955                 960

Asp Ser Asp Glu Asp Tyr Ser Ser Glu Ala Glu Glu Ser Asp Tyr Ser
            965                 970                 975

Lys Glu Ser Leu Gly Ser Glu Glu Ser Gly Lys Asp Trp Asp Glu
            980                 985                 990

Leu Glu Glu Glu Ala Arg Lys Ala  Asp Arg Glu Ser Arg  Tyr Glu Glu
                995                 1000                1005

Glu Glu  Glu Gln Ser Arg Ser  Met Ser Arg Lys Arg  Lys Ala Ser
    1010                1015                1020

Val His  Ser Ser Gly Arg Gly  Ser Asn Arg Gly Ser  Arg His Ser
    1025                1030                1035

Ser Ala  Pro Pro Lys Lys Lys  Arg Lys
    1040                1045

<210> SEQ ID NO 20
<211> LENGTH: 324
<212> TYPE: PRT
<213> ORGANISM: Homo sapiens

<400> SEQUENCE: 20

Met Ser Ser Glu Ala Glu Thr Gln Gln Pro Pro Ala Ala Pro Pro Ala
1               5                   10                  15

Ala Pro Ala Leu Ser Ala Ala Asp Thr Lys Pro Gly Thr Thr Gly Ser
            20                  25                  30

Gly Ala Gly Ser Gly Gly Pro Gly Gly Leu Thr Ser Ala Ala Pro Ala
        35                  40                  45

Gly Gly Asp Lys Lys Val Ile Ala Thr Lys Val Leu Gly Thr Val Lys
    50                  55                  60

Trp Phe Asn Val Arg Asn Gly Tyr Gly Phe Ile Asn Arg Asn Asp Thr
65                  70                  75                  80

Lys Glu Asp Val Phe Val His Gln Thr Ala Ile Lys Lys Asn Asn Pro
                85                  90                  95

Arg Lys Tyr Leu Arg Ser Val Gly Asp Gly Glu Thr Val Glu Phe Asp
            100                 105                 110

Val Val Glu Gly Glu Lys Gly Ala Glu Ala Ala Asn Val Thr Gly Pro
        115                 120                 125

Gly Gly Val Pro Val Gln Gly Ser Lys Tyr Ala Ala Asp Arg Asn His
    130                 135                 140

Tyr Arg Arg Tyr Pro Arg Arg Gly Pro Pro Arg Asn Tyr Gln Gln
145                 150                 155                 160

Asn Tyr Gln Asn Ser Glu Ser Gly Glu Lys Asn Glu Gly Ser Glu Ser
                165                 170                 175

Ala Pro Glu Gly Gln Ala Gln Gln Arg Arg Pro Tyr Arg Arg Arg
            180                 185                 190

Phe Pro Pro Tyr Tyr Met Arg Arg Pro Tyr Gly Arg Arg Pro Gln Tyr
        195                 200                 205
```

-continued

```
Ser Asn Pro Pro Val Gln Gly Glu Val Met Glu Gly Ala Asp Asn Gln
    210                 215                 220
Gly Ala Gly Glu Gln Gly Arg Pro Val Arg Gln Asn Met Tyr Arg Gly
225                 230                 235                 240
Tyr Arg Pro Arg Phe Arg Arg Gly Pro Pro Arg Gln Arg Gln Pro Arg
                245                 250                 255
Glu Asp Gly Asn Glu Glu Asp Lys Glu Asn Gln Gly Asp Glu Thr Gln
            260                 265                 270
Gly Gln Gln Pro Pro Gln Arg Arg Tyr Arg Arg Asn Phe Asn Tyr Arg
        275                 280                 285
Arg Arg Arg Pro Glu Asn Pro Lys Pro Gln Asp Gly Lys Glu Thr Lys
    290                 295                 300
Ala Ala Asp Pro Pro Ala Glu Asn Ser Ser Ala Pro Glu Ala Glu Gln
305                 310                 315                 320
Gly Gly Ala Glu
```

<210> SEQ ID NO 21
<211> LENGTH: 294
<212> TYPE: PRT
<213> ORGANISM: Homo sapiens

<400> SEQUENCE: 21

```
Met Glu Asp Ser Met Asp Met Ser Pro Leu Arg Pro Gln Asn
1               5                   10                  15
Tyr Leu Phe Gly Cys Glu Leu Lys Ala Asp Lys Asp Tyr His Phe Lys
                20                  25                  30
Val Asp Asn Asp Glu Asn Glu His Gln Leu Ser Leu Arg Thr Val Ser
            35                  40                  45
Leu Gly Ala Gly Ala Lys Asp Glu Leu His Ile Val Glu Ala Glu Ala
    50                  55                  60
Met Asn Tyr Glu Gly Ser Pro Ile Lys Val Thr Leu Ala Thr Leu Lys
65                  70                  75                  80
Met Ser Val Gln Pro Thr Val Ser Leu Gly Gly Phe Glu Ile Thr Pro
                85                  90                  95
Pro Val Val Leu Arg Leu Lys Cys Gly Ser Gly Pro Val His Ile Ser
                100                 105                 110
Gly Gln His Leu Val Ala Val Glu Glu Asp Ala Glu Ser Glu Asp Glu
            115                 120                 125
Glu Glu Glu Asp Val Lys Leu Leu Ser Ile Ser Gly Lys Arg Ser Ala
    130                 135                 140
Pro Gly Gly Gly Ser Lys Val Pro Gln Lys Lys Val Lys Leu Ala Ala
145                 150                 155                 160
Asp Glu Asp Asp Asp Asp Asp Glu Glu Asp Asp Glu Asp
                165                 170                 175
Asp Asp Asp Asp Phe Asp Asp Glu Glu Ala Glu Glu Lys Ala Pro Val
                180                 185                 190
Lys Lys Ser Ile Arg Asp Thr Pro Ala Lys Asn Ala Gln Lys Ser Asn
            195                 200                 205
Gln Asn Gly Lys Asp Ser Lys Pro Ser Ser Thr Pro Arg Ser Lys Gly
    210                 215                 220
Gln Glu Ser Phe Lys Lys Gln Glu Lys Thr Pro Lys Thr Pro Lys Gly
225                 230                 235                 240
Pro Ser Ser Val Glu Asp Ile Lys Ala Lys Met Gln Ala Ser Ile Glu
                245                 250                 255
```

Lys Gly Gly Ser Leu Pro Lys Val Glu Ala Lys Phe Ile Asn Tyr Val
            260                 265                 270

Lys Asn Cys Phe Arg Met Thr Asp Gln Glu Ala Ile Gln Asp Leu Trp
        275                 280                 285

Gln Trp Arg Lys Ser Leu
        290

<210> SEQ ID NO 22
<211> LENGTH: 265
<212> TYPE: PRT
<213> ORGANISM: Homo sapiens

<400> SEQUENCE: 22

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Asp Glu Asp Asp Asp
                165                 170                 175

Asp Asp Asp Asp Phe Asp Asp Glu Glu Ala Glu Glu Lys Ala Pro Val
            180                 185                 190

Lys Lys Gly Gln Glu Ser Phe Lys Lys Gln Glu Lys Thr Pro Lys Thr
        195                 200                 205

Pro Lys Gly Pro Ser Ser Val Glu Asp Ile Lys Ala Lys Met Gln Ala
    210                 215                 220

Ser Ile Glu Lys Gly Gly Ser Leu Pro Lys Val Glu Ala Lys Phe Ile
225                 230                 235                 240

Asn Tyr Val Lys Asn Cys Phe Arg Met Thr Asp Gln Glu Ala Ile Gln
                245                 250                 255

Asp Leu Trp Gln Trp Arg Lys Ser Leu
            260                 265

<210> SEQ ID NO 23
<211> LENGTH: 259
<212> TYPE: PRT
<213> ORGANISM: Homo sapiens

<400> SEQUENCE: 23

Met Glu Asp Ser Met Asp Met Asp Met Ser Pro Leu Arg Pro Gln Asn
1               5                   10                  15

```
Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
         35                  40                  45

Leu Gly Ala Gly Ala Lys Asp Glu Leu His Ile Val Glu Ala Glu Ala
 50                  55                  60

Met Asn Tyr Glu Gly Ser Pro Ile Lys Val Thr Leu Ala Thr Leu Lys
 65                  70                  75                  80

Met Ser Val Gln Pro Thr Val Ser Leu Gly Gly Phe Glu Ile Thr Pro
                 85                  90                  95

Pro Val Val Leu Arg Leu Lys Cys Gly Ser Gly Pro Val His Ile Ser
                100                 105                 110

Gly Gln His Leu Val Ala Val Glu Glu Asp Ala Glu Ser Glu Asp Glu
            115                 120                 125

Glu Glu Glu Asp Val Lys Leu Leu Ser Ile Ser Gly Lys Arg Ser Ala
130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Asp Glu Asp Asp
                165                 170                 175

Asp Asp Asp Asp Phe Asp Asp Glu Glu Ala Glu Glu Lys Ala Pro Val
            180                 185                 190

Lys Lys Ser Ile Arg Asp Thr Pro Ala Lys Asn Ala Gln Lys Ser Asn
            195                 200                 205

Gln Asn Gly Lys Asp Ser Lys Pro Ser Ser Thr Pro Arg Ser Lys Gly
            210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Ala His

<210> SEQ ID NO 24
<211> LENGTH: 230
<212> TYPE: PRT
<213> ORGANISM: Homo sapiens

<400> SEQUENCE: 24

Met Asn Tyr Glu Gly Ser Pro Ile Lys Val Thr Leu Ala Thr Leu Lys
1               5                  10                  15

Met Ser Val Gln Pro Thr Val Ser Leu Gly Gly Phe Glu Ile Thr Pro
            20                  25                  30

Pro Val Val Leu Arg Leu Lys Cys Gly Ser Gly Pro Val His Ile Ser
         35                  40                  45

Gly Gln His Leu Val Ala Val Glu Glu Asp Ala Glu Ser Glu Asp Glu
 50                  55                  60

Glu Glu Glu Asp Val Lys Leu Leu Ser Ile Ser Gly Lys Arg Ser Ala
65                  70                  75                  80

Pro Gly Gly Gly Ser Lys Val Pro Gln Lys Lys Val Lys Leu Ala Ala
                 85                  90                  95

Asp Glu Asp Asp Asp Asp Asp Glu Glu Asp Asp Asp Glu Asp Asp
                100                 105                 110

Asp Asp Asp Asp Phe Asp Asp Glu Glu Ala Glu Glu Lys Ala Pro Val
            115                 120                 125
```

```
Lys Lys Ser Ile Arg Asp Thr Pro Ala Lys Asn Ala Gln Lys Ser Asn
            130                 135                 140

Gln Asn Gly Lys Asp Ser Lys Pro Ser Ser Thr Pro Arg Ser Lys Gly
145                 150                 155                 160

Gln Glu Ser Phe Lys Lys Gln Glu Lys Thr Pro Lys Thr Pro Lys Gly
                165                 170                 175

Pro Ser Ser Val Glu Asp Ile Lys Ala Lys Met Gln Ala Ser Ile Glu
                180                 185                 190

Lys Gly Gly Ser Leu Pro Lys Val Glu Ala Lys Phe Ile Asn Tyr Val
                195                 200                 205

Lys Asn Cys Phe Arg Met Thr Asp Gln Glu Ala Ile Gln Asp Leu Trp
210                 215                 220

Gln Trp Arg Lys Ser Leu
225                 230

<210> SEQ ID NO 25
<211> LENGTH: 230
<212> TYPE: PRT
<213> ORGANISM: Homo sapiens

<400> SEQUENCE: 25

Met Glu Asp Ser Met Asp Met Ser Pro Leu Arg Pro Gln Asn
1               5                   10                  15

Tyr Leu Phe Gly Cys Glu Leu Lys Ala Asp Lys Asp Tyr His Phe Lys
                20                  25                  30

Val Asp Asn Asp Glu Asn Glu His Gln Leu Ser Leu Arg Thr Val Ser
                35                  40                  45

Leu Gly Ala Gly Ala Lys Asp Glu Leu His Ile Val Glu Ala Glu Ala
50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
                100                 105                 110

Gly Gln His Leu Val Ala Val Glu Glu Asp Ala Glu Ser Glu Asp Glu
                115                 120                 125

Glu Glu Glu Asp Val Lys Leu Leu Ser Ile Ser Gly Lys Arg Ser Ala
130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Asp Glu Asp Asp
                165                 170                 175

Asp Asp Asp Asp Phe Asp Asp Glu Glu Ala Glu Glu Lys Ala Pro Val
                180                 185                 190

Lys Lys Gly Gln Glu Ser Phe Lys Lys Gln Glu Lys Thr Pro Lys Thr
                195                 200                 205

Pro Lys Gly Pro Ser Ser Val Glu Asp Ile Lys Ala Lys Met Gln Ala
                210                 215                 220

Ser Ile Glu Lys Ala His
225                 230

<210> SEQ ID NO 26
<211> LENGTH: 167
<212> TYPE: PRT
```

<213> ORGANISM: Homo sapiens

<400> SEQUENCE: 26

Met Glu Asp Ser Met Asp Met Ser Pro Leu Arg Pro Gln Asn
1               5                   10                  15

Tyr Leu Phe Ala Val Glu Glu Asp Ala Glu Ser Glu Asp Glu Glu
                20                  25                  30

Glu Asp Val Lys Leu Leu Ser Ile Ser Gly Lys Arg Ser Ala Pro Gly
            35                  40                  45

Gly Gly Ser Lys Val Pro Gln Lys Lys Val Lys Leu Ala Ala Asp Glu
        50                  55                  60

Asp Asp Asp Asp Asp Asp Glu Glu Asp Asp Glu Asp Asp Asp Asp
65                  70                  75                  80

Asp Asp Phe Asp Asp Glu Glu Ala Glu Glu Lys Ala Pro Val Lys Lys
                85                  90                  95

Gly Gln Glu Ser Phe Lys Lys Gln Glu Lys Thr Pro Lys Thr Pro Lys
                100                 105                 110

Gly Pro Ser Ser Val Glu Asp Ile Lys Ala Lys Met Gln Ala Ser Ile
                115                 120                 125

Glu Lys Gly Gly Ser Leu Pro Lys Val Glu Ala Lys Phe Ile Asn Tyr
130                 135                 140

Val Lys Asn Cys Phe Arg Met Thr Asp Gln Glu Ala Ile Gln Asp Leu
145                 150                 155                 160

Trp Gln Trp Arg Lys Ser Leu
                165

<210> SEQ ID NO 27
<211> LENGTH: 394
<212> TYPE: PRT
<213> ORGANISM: Homo sapiens

<400> SEQUENCE: 27

Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
                20                  25                  30

Arg Ser Leu Val Glu Ala Ser Ser Gly Val Ser Val Leu Ser Leu
            35                  40                  45

Cys Glu Lys Gly Asp Ala Met Ile Met Glu Glu Thr Gly Lys Ile Phe
        50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
                85                  90                  95

Asp Tyr Ile Leu Lys Glu Gly Asp Leu Val Lys Ile Asp Leu Gly Val
                100                 105                 110

His Val Asp Gly Phe Ile Ala Asn Val Ala His Thr Phe Val Val Asp
                115                 120                 125

Val Ala Gln Gly Thr Gln Val Thr Gly Arg Lys Ala Asp Val Ile Lys
                130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

```
Phe Asn Cys Thr Pro Ile Glu Gly Met Leu Ser His Gln Leu Lys Gln
                180                 185                 190

His Val Ile Asp Gly Glu Lys Thr Ile Ile Gln Asn Pro Thr Asp Gln
            195                 200                 205

Gln Lys Lys Asp His Glu Lys Ala Glu Phe Glu Val His Glu Val Tyr
        210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
        275                 280                 285

Ala Arg Met Gly Val Val Glu Cys Ala Lys His Glu Leu Leu Gln Pro
290                 295                 300

Phe Asn Val Leu Tyr Glu Lys Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ser Ala Ser Arg Lys Thr Gln Lys
        355                 360                 365

Lys Lys Lys Lys Ala Ser Lys Thr Ala Glu Asn Ala Thr Ser Gly
370                 375                 380

Glu Thr Leu Glu Glu Asn Glu Ala Gly Asp
385                 390

<210> SEQ ID NO 28
<211> LENGTH: 154
<212> TYPE: PRT
<213> ORGANISM: Homo sapiens

<400> SEQUENCE: 28

Met Ala Gln Ser Ile Asn Ile Thr Glu Leu Asn Leu Pro Gln Leu Glu
1               5                   10                  15

Met Leu Lys Asn Gln Leu Asp Gln Glu Val Glu Phe Leu Ser Thr Ser
            20                  25                  30

Ile Ala Gln Leu Lys Val Val Gln Thr Lys Tyr Val Glu Ala Lys Asp
        35                  40                  45

Cys Leu Asn Val Leu Asn Lys Ser Asn Glu Gly Lys Glu Leu Leu Val
    50                  55                  60

Pro Leu Thr Ser Ser Met Tyr Val Pro Gly Lys Leu His Asp Val Glu
65                  70                  75                  80

His Val Leu Ile Asp Val Gly Thr Gly Tyr Tyr Val Glu Lys Thr Ala
                85                  90                  95

Glu Asp Ala Lys Asp Phe Phe Lys Arg Lys Ile Asp Phe Leu Thr Lys
            100                 105                 110

Gln Met Glu Lys Ile Gln Pro Ala Leu Gln Glu Lys His Ala Met Lys
        115                 120                 125

Gln Ala Val Met Glu Met Met Ser Gln Lys Ile Gln Gln Leu Thr Ala
130                 135                 140
```

Leu Gly Ala Ala Gln Ala Thr Ala Lys Ala
145                 150

<210> SEQ ID NO 29
<211> LENGTH: 109
<212> TYPE: PRT
<213> ORGANISM: Homo sapiens

<400> SEQUENCE: 29

Met Ala Gln Ser Ile Asn Ile Thr Glu Leu Asn Leu Pro Gln Leu Glu
1               5                   10                  15

Met Leu Lys Asn Gln Leu Asp Gln Met Tyr Val Pro Gly Lys Leu His
            20                  25                  30

Asp Val Glu His Val Leu Ile Asp Val Gly Thr Gly Tyr Tyr Val Glu
        35                  40                  45

Lys Thr Ala Glu Asp Ala Lys Asp Phe Phe Lys Arg Lys Ile Asp Phe
    50                  55                  60

Leu Thr Lys Gln Met Glu Lys Ile Gln Pro Ala Leu Gln Glu Lys His
65                  70                  75                  80

Ala Met Lys Gln Ala Val Met Glu Met Met Ser Gln Lys Ile Gln Gln
                85                  90                  95

Leu Thr Ala Leu Gly Ala Ala Gln Ala Thr Ala Lys Ala
            100                 105

<210> SEQ ID NO 30
<211> LENGTH: 439
<212> TYPE: PRT
<213> ORGANISM: Homo sapiens

<400> SEQUENCE: 30

Met Asn Leu Leu Pro Asn Ile Glu Ser Pro Val Thr Arg Gln Glu Lys
1               5                   10                  15

Met Ala Thr Val Trp Asp Glu Ala Glu Gln Asp Gly Ile Gly Glu Glu
            20                  25                  30

Val Leu Lys Met Ser Thr Glu Glu Ile Ile Gln Arg Thr Arg Leu Leu
        35                  40                  45

Asp Ser Glu Ile Lys Ile Met Lys Ser Glu Val Leu Arg Val Thr His
    50                  55                  60

Glu Leu Gln Ala Met Lys Asp Lys Ile Lys Glu Asn Ser Glu Lys Ile
65                  70                  75                  80

Lys Val Asn Lys Thr Leu Pro Tyr Leu Val Ser Asn Val Ile Glu Leu
                85                  90                  95

Leu Asp Val Asp Pro Asn Asp Gln Glu Glu Asp Gly Ala Asn Ile Asp
            100                 105                 110

Leu Asp Ser Gln Arg Lys Gly Lys Cys Ala Val Ile Lys Thr Ser Thr
        115                 120                 125

Arg Gln Thr Tyr Phe Leu Pro Val Ile Gly Leu Val Asp Ala Glu Lys
    130                 135                 140

Leu Lys Pro Gly Asp Leu Val Gly Val Asn Lys Asp Ser Tyr Leu Ile
145                 150                 155                 160

Leu Glu Thr Leu Pro Thr Glu Tyr Asp Ser Arg Val Lys Ala Met Glu
                165                 170                 175

Val Asp Glu Arg Pro Thr Glu Gln Tyr Ser Asp Ile Gly Gly Leu Asp
            180                 185                 190

Lys Gln Ile Gln Glu Leu Val Glu Ala Ile Val Leu Pro Met Asn His
        195                 200                 205

```
Lys Glu Lys Phe Glu Asn Leu Gly Ile Gln Pro Lys Gly Val Leu
    210                 215                 220

Met Tyr Gly Pro Pro Gly Thr Gly Lys Thr Leu Leu Ala Arg Ala Cys
225                 230                 235                 240

Ala Ala Gln Thr Lys Ala Thr Phe Leu Lys Leu Ala Gly Pro Gln Leu
                245                 250                 255

Val Gln Met Phe Ile Gly Asp Gly Ala Lys Leu Val Arg Asp Ala Phe
                260                 265                 270

Ala Leu Ala Lys Glu Lys Ala Pro Ser Ile Ile Phe Ile Asp Glu Leu
            275                 280                 285

Asp Ala Ile Gly Thr Lys Arg Phe Asp Ser Glu Lys Ala Gly Asp Arg
290                 295                 300

Glu Val Gln Arg Thr Met Leu Glu Leu Leu Asn Gln Leu Asp Gly Phe
305                 310                 315                 320

Gln Pro Asn Thr Gln Val Lys Val Ile Ala Ala Thr Asn Arg Val Asp
                325                 330                 335

Ile Leu Asp Pro Ala Leu Leu Arg Ser Gly Arg Leu Asp Arg Lys Ile
                340                 345                 350

Glu Phe Pro Met Pro Asn Glu Glu Ala Arg Ala Arg Ile Met Gln Ile
            355                 360                 365

His Ser Arg Lys Met Asn Val Ser Pro Asp Val Asn Tyr Glu Glu Leu
370                 375                 380

Ala Arg Cys Thr Asp Asp Phe Asn Gly Ala Gln Cys Lys Ala Val Cys
385                 390                 395                 400

Val Glu Ala Gly Met Ile Ala Leu Arg Arg Gly Ala Thr Glu Leu Thr
                405                 410                 415

His Glu Asp Tyr Met Glu Gly Ile Leu Glu Val Gln Ala Lys Lys Lys
            420                 425                 430

Ala Asn Leu Gln Tyr Tyr Ala
            435

<210> SEQ ID NO 31
<211> LENGTH: 464
<212> TYPE: PRT
<213> ORGANISM: Homo sapiens

<400> SEQUENCE: 31

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
                20                  25                  30

Phe Lys Arg Ser Arg Asn Thr Asp Glu Met Val Glu Leu Arg Ile Leu
            35                  40                  45

Leu Gln Ser Lys Asn Ala Gly Ala Val Ile Gly Lys Gly Gly Lys Asn
        50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125
```

```
Ala Val Glu Cys Leu Asn Tyr Gln His Tyr Lys Gly Ser Asp Phe Asp
            130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
        195                 200                 205

Ile Leu Asp Leu Ile Ser Glu Ser Pro Ile Lys Gly Arg Ala Gln Pro
    210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Met Ser Pro Arg Arg Gly
        275                 280                 285

Pro Pro Pro Pro Pro Gly Arg Gly Gly Arg Gly Gly Ser Arg Ala
    290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
        355                 360                 365

Tyr Asp Tyr Ser Tyr Ala Gly Gly Arg Gly Ser Tyr Gly Asp Leu Gly
    370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
                405                 410                 415

Ser Gly Ala Ser Ile Lys Ile Asp Glu Pro Leu Glu Gly Ser Glu Asp
            420                 425                 430

Arg Ile Ile Thr Ile Thr Gly Thr Gln Asp Gln Ile Gln Asn Ala Gln
        435                 440                 445

Tyr Leu Leu Gln Asn Ser Val Lys Gln Tyr Ala Asp Val Glu Gly Phe
    450                 455                 460

<210> SEQ ID NO 32
<211> LENGTH: 463
<212> TYPE: PRT
<213> ORGANISM: Homo sapiens

<400> SEQUENCE: 32

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30
```

```
Phe Lys Arg Ser Arg Asn Thr Asp Glu Met Val Glu Leu Arg Ile Leu
        35                  40                  45
Leu Gln Ser Lys Asn Ala Gly Ala Val Ile Gly Lys Gly Gly Lys Asn
    50                  55                  60
Ile Lys Ala Leu Arg Thr Asp Tyr Asn Ala Ser Val Ser Val Pro Asp
65                  70                  75                  80
Ser Ser Gly Pro Glu Arg Ile Leu Ser Ile Ser Ala Asp Ile Glu Thr
                85                  90                  95
Ile Gly Glu Ile Leu Lys Lys Ile Ile Pro Thr Leu Glu Glu Gly Leu
                100                 105                 110
Gln Leu Pro Ser Pro Thr Ala Thr Ser Gln Leu Pro Leu Glu Ser Asp
            115                 120                 125
Ala Val Glu Cys Leu Asn Tyr Gln His Tyr Lys Gly Ser Asp Phe Asp
        130                 135                 140
Cys Glu Leu Arg Leu Leu Ile His Gln Ser Leu Ala Gly Gly Ile Ile
145                 150                 155                 160
Gly Val Lys Gly Ala Lys Ile Lys Glu Leu Arg Glu Asn Thr Gln Thr
                165                 170                 175
Thr Ile Lys Leu Phe Gln Glu Cys Cys Pro His Ser Thr Asp Arg Val
            180                 185                 190
Val Leu Ile Gly Gly Lys Pro Asp Arg Val Val Glu Cys Ile Lys Ile
        195                 200                 205
Ile Leu Asp Leu Ile Ser Glu Ser Pro Ile Lys Gly Arg Ala Gln Pro
210                 215                 220
Tyr Asp Pro Asn Phe Tyr Asp Glu Thr Tyr Asp Tyr Gly Gly Phe Thr
225                 230                 235                 240
Met Met Phe Asp Asp Arg Arg Gly Arg Pro Val Gly Phe Pro Met Arg
                245                 250                 255
Gly Arg Gly Gly Phe Asp Arg Met Pro Pro Gly Arg Gly Gly Arg Pro
                260                 265                 270
Met Pro Pro Ser Arg Arg Asp Tyr Asp Asp Met Ser Pro Arg Arg Gly
            275                 280                 285
Pro Pro Pro Pro Pro Gly Arg Gly Gly Arg Gly Gly Ser Arg Ala
        290                 295                 300
Arg Asn Leu Pro Leu Pro Pro Pro Pro Arg Gly Gly Asp Leu
305                 310                 315                 320
Met Ala Tyr Asp Arg Arg Gly Arg Pro Gly Asp Arg Tyr Asp Gly Met
                325                 330                 335
Val Gly Phe Ser Ala Asp Glu Thr Trp Asp Ser Ala Ile Asp Thr Trp
            340                 345                 350
Ser Pro Ser Glu Trp Gln Met Ala Tyr Glu Pro Gln Gly Gly Ser Gly
            355                 360                 365
Tyr Asp Tyr Ser Tyr Ala Gly Arg Gly Ser Tyr Gly Asp Leu Gly
        370                 375                 380
Gly Pro Ile Ile Thr Thr Gln Val Thr Ile Pro Lys Asp Leu Ala Gly
385                 390                 395                 400
Ser Ile Ile Gly Lys Gly Gly Gln Arg Ile Lys Gln Ile Arg His Glu
                405                 410                 415
Ser Gly Ala Ser Ile Lys Ile Asp Glu Pro Leu Glu Gly Ser Glu Asp
            420                 425                 430
Arg Ile Ile Thr Ile Thr Gly Thr Gln Asp Gln Ile Gln Asn Ala Gln
        435                 440                 445
```

Tyr Leu Gln Asn Ser Val Lys Gln Tyr Ser Gly Lys Phe Phe
    450                 455                 460

<210> SEQ ID NO 33
<211> LENGTH: 439
<212> TYPE: PRT
<213> ORGANISM: Homo sapiens

<400> SEQUENCE: 33

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Tyr Gln
            100                 105                 110

His Tyr Lys Gly Ser Asp Phe Asp Cys Glu Leu Arg Leu Leu Ile His
        115                 120                 125

Gln Ser Leu Ala Gly Gly Ile Ile Gly Val Lys Gly Ala Lys Ile Lys
    130                 135                 140

Glu Leu Arg Glu Asn Thr Gln Thr Thr Ile Lys Leu Phe Gln Glu Cys
145                 150                 155                 160

Cys Pro His Ser Thr Asp Arg Val Val Leu Ile Gly Gly Lys Pro Asp
                165                 170                 175

Arg Val Val Glu Cys Ile Lys Ile Ile Leu Asp Leu Ile Ser Glu Ser
            180                 185                 190

Pro Ile Lys Gly Arg Ala Gln Pro Tyr Asp Pro Asn Phe Tyr Asp Glu
        195                 200                 205

Thr Tyr Asp Tyr Gly Gly Phe Thr Met Met Phe Asp Asp Arg Arg Gly
    210                 215                 220

Arg Pro Val Gly Phe Pro Met Arg Gly Arg Gly Gly Phe Asp Arg Met
225                 230                 235                 240

Pro Pro Gly Arg Gly Gly Arg Pro Met Pro Pro Ser Arg Arg Asp Tyr
                245                 250                 255

Asp Asp Met Ser Pro Arg Arg Gly Pro Pro Pro Pro Gly Arg
            260                 265                 270

Gly Gly Arg Gly Gly Ser Arg Ala Arg Asn Leu Pro Leu Pro Pro Pro
        275                 280                 285

Pro Pro Pro Arg Gly Gly Asp Leu Met Ala Tyr Asp Arg Arg Gly Arg
    290                 295                 300

Pro Gly Asp Arg Tyr Asp Gly Met Val Gly Phe Ser Ala Asp Glu Thr
305                 310                 315                 320

Trp Asp Ser Ala Ile Asp Thr Trp Ser Pro Ser Glu Trp Gln Met Ala
                325                 330                 335

Tyr Glu Pro Gln Gly Gly Ser Gly Tyr Asp Tyr Ser Tyr Ala Gly Gly
            340                 345                 350

Arg Gly Ser Tyr Gly Asp Leu Gly Gly Pro Ile Ile Thr Thr Gln Val
        355                 360                 365

```
Thr Ile Pro Lys Asp Leu Ala Gly Ser Ile Ile Gly Lys Gly Gly Gln
        370                 375                 380

Arg Ile Lys Gln Ile Arg His Glu Ser Gly Ala Ser Ile Lys Ile Asp
385                 390                 395                 400

Glu Pro Leu Glu Gly Ser Glu Asp Arg Ile Ile Thr Ile Thr Gly Thr
                405                 410                 415

Gln Asp Gln Ile Gln Asn Ala Gln Tyr Leu Leu Gln Asn Ser Val Lys
                420                 425                 430

Gln Tyr Ser Gly Lys Phe Phe
                435

<210> SEQ ID NO 34
<211> LENGTH: 440
<212> TYPE: PRT
<213> ORGANISM: Homo sapiens

<400> SEQUENCE: 34

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
                20                  25                  30

Phe Lys Arg Ser Arg Asn Thr Asp Glu Met Val Glu Leu Arg Ile Leu
            35                  40                  45

Leu Gln Ser Lys Asn Ala Gly Ala Val Ile Gly Lys Gly Gly Lys Asn
        50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Tyr Gln
                100                 105                 110

His Tyr Lys Gly Ser Asp Phe Asp Cys Glu Leu Arg Leu Leu Ile His
            115                 120                 125

Gln Ser Leu Ala Gly Gly Ile Ile Gly Val Lys Gly Ala Lys Ile Lys
        130                 135                 140

Glu Leu Arg Glu Asn Thr Gln Thr Thr Ile Lys Leu Phe Gln Glu Cys
145                 150                 155                 160

Cys Pro His Ser Thr Asp Arg Val Val Leu Ile Gly Gly Lys Pro Asp
                165                 170                 175

Arg Val Val Glu Cys Ile Lys Ile Ile Leu Asp Leu Ile Ser Glu Ser
                180                 185                 190

Pro Ile Lys Gly Arg Ala Gln Pro Tyr Asp Pro Asn Phe Tyr Asp Glu
            195                 200                 205

Thr Tyr Asp Tyr Gly Gly Phe Thr Met Met Phe Asp Asp Arg Arg Gly
        210                 215                 220

Arg Pro Val Gly Phe Pro Met Arg Gly Arg Gly Gly Phe Asp Arg Met
225                 230                 235                 240

Pro Pro Gly Arg Gly Gly Arg Pro Met Pro Pro Ser Arg Arg Asp Tyr
                245                 250                 255

Asp Asp Met Ser Pro Arg Arg Gly Pro Pro Pro Pro Pro Pro Gly Arg
            260                 265                 270

Gly Gly Arg Gly Gly Ser Arg Ala Arg Asn Leu Pro Leu Pro Pro Pro
        275                 280                 285
```

```
Pro Pro Pro Arg Gly Gly Asp Leu Met Ala Tyr Asp Arg Gly Arg
    290                 295                 300

Pro Gly Asp Arg Tyr Asp Gly Met Val Gly Phe Ser Ala Asp Glu Thr
305                 310                 315                 320

Trp Asp Ser Ala Ile Asp Thr Trp Ser Pro Ser Glu Trp Gln Met Ala
                325                 330                 335

Tyr Glu Pro Gln Gly Gly Ser Gly Tyr Asp Tyr Ser Tyr Ala Gly Gly
            340                 345                 350

Arg Gly Ser Tyr Gly Asp Leu Gly Gly Pro Ile Ile Thr Thr Gln Val
        355                 360                 365

Thr Ile Pro Lys Asp Leu Ala Gly Ser Ile Ile Gly Lys Gly Gly Gln
    370                 375                 380

Arg Ile Lys Gln Ile Arg His Glu Ser Gly Ala Ser Ile Lys Ile Asp
385                 390                 395                 400

Glu Pro Leu Glu Gly Ser Glu Asp Arg Ile Ile Thr Ile Thr Gly Thr
                405                 410                 415

Gln Asp Gln Ile Gln Asn Ala Gln Tyr Leu Leu Gln Asn Ser Val Lys
            420                 425                 430

Gln Tyr Ala Asp Val Glu Gly Phe
        435                 440

<210> SEQ ID NO 35
<211> LENGTH: 30
<212> TYPE: PRT
<213> ORGANISM: Mus musculus

<400> SEQUENCE: 35

Gly Gly Lys Gly Thr Ala Arg Arg Lys Lys Val Val His Arg Thr
1               5                   10                  15

Ala Thr Ala Asp Asp Lys Lys Leu Gln Phe Ser Leu Lys Lys
            20                  25                  30

<210> SEQ ID NO 36
<211> LENGTH: 30
<212> TYPE: PRT
<213> ORGANISM: Mus musculus

<400> SEQUENCE: 36

Arg Glu Lys Asn Glu Ser Asn Lys Ser Ser Phe Asp Lys Met Ile Asp
1               5                   10                  15

Ala Ile Lys Glu Ser Lys Ser Gly Lys Lys Ile Gly Val Phe
            20                  25                  30

<210> SEQ ID NO 37
<211> LENGTH: 30
<212> TYPE: PRT
<213> ORGANISM: Mus musculus

<400> SEQUENCE: 37

Ser Ala Pro Glu Gly Gln Ala Gln Gln Arg Arg Pro Tyr Arg Arg
1               5                   10                  15

Arg Phe Pro Pro Tyr Tyr Met Arg Arg Pro Tyr Ala Arg Arg
            20                  25                  30

<210> SEQ ID NO 38
<211> LENGTH: 30
<212> TYPE: PRT
<213> ORGANISM: Mus musculus
```

```
<400> SEQUENCE: 38

Gly Glu Gln Gly Arg Pro Val Arg Gln Asn Met Tyr Arg Gly Tyr Arg
1               5                   10                  15

Pro Arg Phe Arg Arg Gly Pro Pro Arg Gln Arg Gln Pro Arg
            20                  25                  30

<210> SEQ ID NO 39
<211> LENGTH: 30
<212> TYPE: PRT
<213> ORGANISM: Mus musculus

<400> SEQUENCE: 39

Gln Pro Pro Gln Arg Arg Tyr Arg Arg Asn Phe Asn Tyr Arg Arg Arg
1               5                   10                  15

Arg Pro Glu Asn Pro Lys Pro Gln Asp Gly Lys Glu Thr Lys
            20                  25                  30

<210> SEQ ID NO 40
<211> LENGTH: 30
<212> TYPE: PRT
<213> ORGANISM: Mus musculus

<400> SEQUENCE: 40

Asn Gly Lys Asp Leu Lys Pro Ser Thr Pro Arg Ser Lys Gly Gln Glu
1               5                   10                  15

Ser Phe Lys Lys Gln Glu Lys Thr Pro Lys Thr Pro Lys Gly
            20                  25                  30

<210> SEQ ID NO 41
<211> LENGTH: 30
<212> TYPE: PRT
<213> ORGANISM: Mus musculus

<400> SEQUENCE: 41

Lys Gly Gln Glu Ser Phe Lys Lys Gln Glu Lys Thr Pro Lys Thr Pro
1               5                   10                  15

Lys Gly Pro Ser Ser Val Glu Asp Ile Lys Ala Lys Met Gln
            20                  25                  30

<210> SEQ ID NO 42
<211> LENGTH: 30
<212> TYPE: PRT
<213> ORGANISM: Mus musculus

<400> SEQUENCE: 42

Val Ser Val Leu Ser Leu Cys Glu Lys Gly Asp Ala Met Ile Met Glu
1               5                   10                  15

Glu Thr Gly Lys Ile Phe Lys Lys Glu Lys Glu Met Lys Lys
            20                  25                  30

<210> SEQ ID NO 43
<211> LENGTH: 30
<212> TYPE: PRT
<213> ORGANISM: Mus musculus

<400> SEQUENCE: 43

Ala Lys Asp Phe Phe Lys Arg Lys Ile Asp Phe Leu Thr Lys Gln Met
1               5                   10                  15

Glu Lys Ile Gln Pro Ala Leu Gln Glu Lys His Ala Met Lys
            20                  25                  30
```

```
<210> SEQ ID NO 44
<211> LENGTH: 30
<212> TYPE: PRT
<213> ORGANISM: Mus musculus

<400> SEQUENCE: 44

Ile Lys Ile Met Lys Ser Glu Val Leu Arg Val Thr His Glu Leu Gln
1               5                   10                  15

Ala Met Lys Asp Lys Ile Lys Glu Asn Ser Glu Lys Ile Lys
            20                  25                  30

<210> SEQ ID NO 45
<211> LENGTH: 30
<212> TYPE: PRT
<213> ORGANISM: Mus musculus

<400> SEQUENCE: 45

Met Phe Asp Asp Arg Arg Gly Arg Pro Val Gly Phe Pro Met Arg Gly
1               5                   10                  15

Arg Gly Gly Phe Asp Arg Met Pro Pro Gly Arg Gly Gly Arg
            20                  25                  30

<210> SEQ ID NO 46
<211> LENGTH: 30
<212> TYPE: PRT
<213> ORGANISM: Homo sapiens

<400> SEQUENCE: 46

Gly Gly Lys Gly Thr Ala Arg Arg Lys Lys Val Val His Arg Thr
1               5                   10                  15

Ala Thr Ala Asp Asp Lys Lys Leu Gln Phe Ser Leu Lys Lys
            20                  25                  30

<210> SEQ ID NO 47
<211> LENGTH: 30
<212> TYPE: PRT
<213> ORGANISM: Homo sapiens

<400> SEQUENCE: 47

Arg Glu Lys Asn Glu Ser Asn Lys Ser Ser Phe Asp Lys Met Ile Glu
1               5                   10                  15

Ala Ile Lys Glu Ser Lys Asn Gly Lys Lys Ile Gly Val Phe
            20                  25                  30

<210> SEQ ID NO 48
<211> LENGTH: 30
<212> TYPE: PRT
<213> ORGANISM: Homo sapiens

<400> SEQUENCE: 48

Ser Ala Pro Glu Gly Gln Ala Gln Arg Arg Pro Tyr Arg Arg Arg
1               5                   10                  15

Arg Phe Pro Pro Tyr Tyr Met Arg Pro Tyr Gly Arg Arg
            20                  25                  30

<210> SEQ ID NO 49
<211> LENGTH: 30
<212> TYPE: PRT
<213> ORGANISM: Homo sapiens

<400> SEQUENCE: 49

Gly Glu Gln Gly Arg Pro Val Arg Gln Asn Met Tyr Arg Gly Tyr Arg
1               5                   10                  15
```

-continued

```
Pro Arg Phe Arg Arg Gly Pro Pro Arg Gln Arg Gln Pro Arg
            20                  25                  30

<210> SEQ ID NO 50
<211> LENGTH: 30
<212> TYPE: PRT
<213> ORGANISM: Homo sapiens

<400> SEQUENCE: 50

Gln Pro Pro Gln Arg Arg Tyr Arg Arg Asn Phe Asn Tyr Arg Arg Arg
1               5                   10                  15

Arg Pro Glu Asn Pro Lys Pro Gln Asp Gly Lys Glu Thr Lys
            20                  25                  30

<210> SEQ ID NO 51
<211> LENGTH: 31
<212> TYPE: PRT
<213> ORGANISM: Homo sapiens

<400> SEQUENCE: 51

Asn Gly Lys Asp Ser Lys Pro Ser Ser Thr Pro Arg Ser Lys Gly Gln
1               5                   10                  15

Glu Ser Phe Lys Lys Gln Glu Lys Thr Pro Lys Thr Pro Lys Gly
            20                  25                  30

<210> SEQ ID NO 52
<211> LENGTH: 30
<212> TYPE: PRT
<213> ORGANISM: Homo sapiens

<400> SEQUENCE: 52

Lys Gly Gln Glu Ser Phe Lys Lys Gln Glu Lys Thr Pro Lys Thr Pro
1               5                   10                  15

Lys Gly Pro Ser Ser Val Glu Asp Ile Lys Ala Lys Met Gln
            20                  25                  30

<210> SEQ ID NO 53
<211> LENGTH: 30
<212> TYPE: PRT
<213> ORGANISM: Homo sapiens

<400> SEQUENCE: 53

Val Ser Val Leu Ser Leu Cys Glu Lys Gly Asp Ala Met Ile Met Glu
1               5                   10                  15

Glu Thr Gly Lys Ile Phe Lys Lys Glu Lys Glu Met Lys Lys
            20                  25                  30

<210> SEQ ID NO 54
<211> LENGTH: 30
<212> TYPE: PRT
<213> ORGANISM: Homo sapiens

<400> SEQUENCE: 54

Ala Lys Asp Phe Phe Lys Arg Lys Ile Asp Phe Leu Thr Lys Gln Met
1               5                   10                  15

Glu Lys Ile Gln Pro Ala Leu Gln Glu Lys His Ala Met Lys
            20                  25                  30

<210> SEQ ID NO 55
<211> LENGTH: 30
<212> TYPE: PRT
<213> ORGANISM: Homo sapiens
```

<400> SEQUENCE: 55

| Ile | Lys | Ile | Met | Lys | Ser | Glu | Val | Leu | Arg | Val | Thr | His | Glu | Leu | Gln |
|---|---|---|---|---|---|---|---|---|---|---|---|---|---|---|---|
| 1 | | | | 5 | | | | | 10 | | | | | 15 | |

| Ala | Met | Lys | Asp | Lys | Ile | Lys | Glu | Asn | Ser | Glu | Lys | Ile | Lys |
|---|---|---|---|---|---|---|---|---|---|---|---|---|---|
| | 20 | | | | | 25 | | | | | 30 | | |

<210> SEQ ID NO 56
<211> LENGTH: 30
<212> TYPE: PRT
<213> ORGANISM: Homo sapiens

<400> SEQUENCE: 56

| Met | Phe | Asp | Asp | Arg | Arg | Gly | Arg | Pro | Val | Gly | Phe | Pro | Met | Arg | Gly |
|---|---|---|---|---|---|---|---|---|---|---|---|---|---|---|---|
| 1 | | | | 5 | | | | | 10 | | | | | 15 | |

| Arg | Gly | Gly | Phe | Asp | Arg | Met | Pro | Pro | Gly | Arg | Gly | Arg |
|---|---|---|---|---|---|---|---|---|---|---|---|---|
| | | 20 | | | | | 25 | | | | | 30 |

<210> SEQ ID NO 57
<211> LENGTH: 615
<212> TYPE: DNA
<213> ORGANISM: Mus musculus

<400> SEQUENCE: 57

```
atgcgacgga cgggcgctcc cacccaggcg gactctcggg ggcgagggcg agccagggcc      60
ggctggcccg gggccgaagc gacgccctct ctccctctcg gcggaagccg aggacgggag     120
tctcagatga agaaacaat catgaaccag gagaaactcg ccaaactgca ggcacaagtg     180
cgcattggtg ggaaaggaac tgctcgtagg aagaagaagg tggttcacag aacggccaca     240
gcagacgata gaaaactgca gttctcctta aagaagttag gggtgaacaa catctctggt     300
attgaagagg tgaacatgtt tacaaaccaa ggaacagtga tccattttaa caaccctaaa     360
gttcaggcat ccctggcagc aaacaccttc accattacag ccacgctga dacaaagcag     420
ctgacagaaa tgcttcccag catcctcaac agcttggtg cagacagcct gactagttta     480
aggagactgg ctgaagctct gcccaaacaa tctgtggatg gaaaagcacc ccttgctact     540
ggagaggatg atgatgatga agttccagat ctggtggaga attttgatga ggcttctaag     600
aatgaggcaa actga                                                     615
```

<210> SEQ ID NO 58
<211> LENGTH: 489
<212> TYPE: DNA
<213> ORGANISM: Mus musculus

<400> SEQUENCE: 58

```
atgaaagaaa caatcatgaa ccaggagaaa ctcgccaaac tgcaggcaca agtgcgcatt      60
ggtgggaaag gaactgctcg taggaagaag aaggtggttc acagaacggc cacagcagac     120
gataagaaac tgcagttctc cttaaagaag ttaggggtga acaacatctc tggtattgaa     180
gaggtgaaca tgtttacaaa ccaaggaaca gtgatccatt ttaacaaccc taaagttcag     240
gcatccctgg cagcaaacac cttcaccatt acaggccacg ctgagacaaa gcagctgaca     300
gaaatgcttc ccagcatcct caaccagctt ggtgcagaca gcctgactag tttaaggaga     360
ctggctgaag ctctgcccaa acaatctgtg gatggaaaag caccccttgc tactggagag     420
gatgatgatg atgaagttcc agatctggtg gagaattttg atgaggcttc taagaatgag     480
gcaaactga                                                            489
```

<210> SEQ ID NO 59
<211> LENGTH: 3144
<212> TYPE: DNA
<213> ORGANISM: Mus musculus

<400> SEQUENCE: 59

| | | | | | | |
|---|---|---|---|---|---|---|
| atggctgtga | ctctggacaa | agacgcgtac | taccggcgag | tgaagagatt | gtacagtaac | 60 |
| tggcggaaag | gagaagatga | gtatgccagt | attgatgcca | ttgttgtatc | ggtgggtgtt | 120 |
| gatgaagaaa | ttgtgtatgc | caagtcaact | gccttacaga | cgtggctctt | tggttatgaa | 180 |
| ctaactgata | caatcatggt | cttctgtgat | gacaaaatca | tcttcatggc | cagcaaaaag | 240 |
| aaggtggagt | ttctgaaaca | gattgccaat | actaaaggca | atgagaatgc | taatggagcc | 300 |
| cctgccatca | cactgcttgt | cagagagaag | aatgaaagta | caagagcag | ctttgacaaa | 360 |
| atgattgacg | ctatcaaaga | aagcaagagc | ggcaagaaga | tcggagtgtt | cagcaaagac | 420 |
| aagttccctg | gagagttcat | gaagagctgg | agtgattgtc | tcaacaagga | gggctttgac | 480 |
| aaagtagaca | tcagcgctgt | tgtggcatac | accattgctg | tgaaagagga | cggtgagctc | 540 |
| aacctgatga | agaaagcagc | cagcatcacc | tctgaggtct | tcaacaagtt | ctttaaggaa | 600 |
| agagtcatgg | aaatagtgga | tgcagatgag | aaagttcggc | atagcaaatt | ggctgagtct | 660 |
| gtggaaaagg | ccattgaaga | aaaaaaatac | ctagctgggg | cagatccttc | tactgtggaa | 720 |
| atgtgttacc | ctcctatcat | tcagagtggt | ggcaactata | atctcaagtt | cagtgtggtg | 780 |
| agtgataaga | atcatatgca | ttttggggcc | attacgtgtg | ccatgggcat | tcgctttaaa | 840 |
| tcttactgct | ccaaccttgt | tcgcactctg | atggttgacc | ccactcagga | agttcaagaa | 900 |
| aattacaact | ttttacttca | acttcaagag | gagttgctaa | aggaattaag | acatggtgtg | 960 |
| aagatatgtg | atgtgtataa | ctctgtcatg | gatgtggtta | agaagcagaa | accagaattg | 1020 |
| ctgaacaaaa | ttacaaagaa | tctaggattt | gggatgggaa | ttgaattccg | tgaaggctct | 1080 |
| ctagtaatca | atagtaaaaa | tcagtacaag | ctaaagaaag | ggatggtttt | tagcatcaat | 1140 |
| ctaggatttt | cagacctgac | taacaaagaa | gggaaaaagc | cagaagagaa | aacctatgcc | 1200 |
| ctgttcattg | gtgacacggt | gcttgtagat | gaggatggtc | cagccactat | tcttacttct | 1260 |
| gtgaaaaaga | aagtaaagaa | tgtggggatt | ttcctgaaga | atgaggatga | tgaagaggag | 1320 |
| gaggaagaga | aagatgaggc | agaggacctt | tgggaagag | gctctagggc | ggcattactt | 1380 |
| actgaaagaa | caaggaatga | gatgactgca | gaagagaagc | gaagagcaca | tcagaaggaa | 1440 |
| ctggcagcac | agctcaacga | ggaagcgaag | aggaggctga | cagagcagaa | aggggaacag | 1500 |
| cagattcaga | agctcgaaa | atctaatgtg | tcctataaaa | acccatctct | gatgcctaag | 1560 |
| gaaccacata | ttcgggagat | gaagatctat | attgataaga | aatatgagac | tgtgataatg | 1620 |
| cctgtgtttg | gcattgccac | acccttccat | attgccacaa | tcaagaacat | aagtatgtct | 1680 |
| gtcgaaggag | actatactta | cttgcgaatc | aacttctatt | gtccaggcag | tgctctgggc | 1740 |
| aggaatgagg | gcaacatctt | tcctaaccct | gaagccactt | ttgtcaagga | aattacatac | 1800 |
| cgagcttcaa | atatgaaagc | acctggagag | cagactgtac | ccgccttaaa | tcttcagaat | 1860 |
| gcgttccgaa | ttataaaaga | agtacaaaaa | cgttacaaga | ccagaagc | tgaagagaaa | 1920 |
| gaaaaagagg | gcattgtaaa | acaagactcg | ctggtgatca | acctaaaccg | gagtaatcca | 1980 |
| aaactgaaag | acctgtacat | tcgtccaaac | attgcccaga | agagaatgca | gggctcactg | 2040 |
| gaggctcatg | tcaatggttt | ccgattcaca | tctgttcgag | agacaaggt | ggatattctg | 2100 |
| tacaataata | tcaagcatgc | gctgttccag | ccctgtgatg | gcgagatgat | tattgttttg | 2160 |

```
cactttcacc tcaagaatgc tatcatgttt gggaagaagc gacacacaga tgtacagttc    2220
tacacagaag ttggagagat cactacagat ttggggaaac atcaacacat gcatgaccga    2280
gatgacctgt atgctgagca gatggaacga gaaatgagac acaaactgaa aacggccttt    2340
aaaaatttca ttgaaaaagt agaggcccta acaaaggagg agctggagtt tgaagtgcca    2400
tttagggacc tggggtttaa tggggctccc tacaggagta cctgcctcct tcagcccact    2460
agtagtgccc tggtaaatgc tacagagtgg ccacccttttg tggtgacact ggatgaagtg    2520
gagctgatcc attttgagag ggtccagttt cacctgaaga actttgatat ggtcattgtc    2580
tacaaggatt acagcaagaa agtcacgatg atcaatgcta ttcctgttgc ctctctagac    2640
cccatcaagg agtggctgaa ttcctgtgac ctaaagtaca cagaaggagt tcagtctctc    2700
aactggacta aaatcatgaa gaccattgtt gatgaccccg agggcttctt tgaacaaggt    2760
ggctggtcct tcctggaacc tgagggtgag gggagtgacg ctgaggacgg agactcggag    2820
tctgaaattg aagatgagac tttcaatcct tctgaagatg actatgaaga ggaagaagag    2880
gacagcgatg aagattactc atcagaagct gaagaatcag actattctaa ggaatctctg    2940
ggaagtgaag aagaaagcgg gaaggactgg gatgagctag aagaagaagc acgaaaagcg    3000
gaccgggaaa gccgttatga ggaggaagaa gaacagagcc gaagtatgag ccggaagagg    3060
aaggcatctg tacatagttc aggccgtggc tctaaccgtg gttccagaca cagctctgca    3120
cccccgaaga aaaagagaaa gtaa                                          3144
```

<210> SEQ ID NO 60
<211> LENGTH: 969
<212> TYPE: DNA
<213> ORGANISM: Mus musculus

<400> SEQUENCE: 60

```
atgagcagcg aggccgagac ccagcagccg cccgccgccc ccgccgccgc cctcagcgcc     60
gccgacacca gcccggctc cacgggcagc ggcgcgggta gtggcggccc gggtggcctc    120
acatcggcgg cgcccgccgg cggggacaag aaggtcatcg caacgaaggt tttgggaaca    180
gtcaaatggt tcaatgtaag gaacggatac ggtttcatca acaggaatga caccaaggaa    240
gacgtatttg tacaccagac tgccataaag aagaataacc ccaggaagta ccttcgcagt    300
gtaggcgatg gagagactgt ggagtttgat gttgttgaag agaaagggg tgcggaggca    360 gcaaatgtta caggccctgg tggagttcca gttcaaggca gtaaatacgc agcagaccgt    420
aaccattata gacgctatcc acgtcgtagg ggtcctccac gcaattacca gcaaaattac    480
cagaatagtg agagtgggga aaagaacgag ggatcggaaa gcgctcctga aggccaggcc    540
caacaacgcc ggcccttacg caggcgaagg ttcccaccctt actacatgcg agaccctat    600 gcgcgtcgac cacagtattc caaccccctt gtgcaaggag aagtgatgga gggtgctgac    660
aaccagggtg caggagagca aggtagacca gtgagacaga atatgtatcg gggttacaga    720
ccacgattcc gaaggggccc tcctcgccaa agacagccta gaggatgg caatgaagag    780 gacaaagaaa atcaaggaga tgagacccaa ggtcagcagc cacctcaacg tcggtatcgc    840
cgaaacttca attaccgacg cagacgccca gagaacccta accacaaga tggcaaagag    900 acaaaagcag ccgatccacc agctgagaat tcgtccgctc ccgaggctga gcagggcggg    960
gctgagtaa                                                           969
```

<210> SEQ ID NO 61

```
<211> LENGTH: 879
<212> TYPE: DNA
<213> ORGANISM: Mus musculus

<400> SEQUENCE: 61
atggaagact cgatggatat ggacatgagt cctcttaggc ctcagaacta ccttttcggc    60
tgtgaactaa aggctgacaa agactatcac tttaaagtgg ataatgatga aaatgagcac   120
cagttgtcat taagaacggt cagtttagga gcagggcaa aagatgagtt acacatcgta   180
gaggcagaag caatgaacta tgaaggcagt ccaattaaag taacactggc aactttgaaa   240
atgtctgtac aaccaacagt ttccctaggg ggctttgaaa ttacaccacc tgtggtctta   300
cggttgaagt gtggttcagg gcctgtgcac attagtggac agcatctagt agctgtagag   360
gaagatgcag agtctgaaga tgaagatgag gaggacgtaa aactcttagg catgtctgga   420
aagcgatctg ctcctggagg tggtaacaag gttccacaga aaaaagtaaa acttgatgaa   480
gatgatgagg acgatgatga ggacgatgag gatgatgagg atgatgatga tgatgatttt   540
gatgaagagg aaactgaaga aaaggtccca gtgaagaaat ctgtacgaga tacccccagcc  600
aaaaatgcac aaaaatcaaa ccaaaatgga aaagacttaa aaccatcaac accgagatca   660
aagggtcaag agtccttcaa aaaacaggaa aagactccta aaacaccaaa aggacctagt   720
tctgtagaag acattaaggc aaaaatgcaa gcaagtatag aaaaaggcgg ttctcttccc   780
aaagtggaag ccaagttcat taattatgtg aagaattgtt tccggatgac tgaccaggag   840
gctattcaag atctctggca gtggaggaaa tctctttaa                           879

<210> SEQ ID NO 62
<211> LENGTH: 840
<212> TYPE: DNA
<213> ORGANISM: Mus musculus

<400> SEQUENCE: 62
atggaagact cgatggatat ggacatgagt cctcttaggc ctcagaacta ccttttcgtg    60
gataatgatg aaaatgagca ccagttgtca ttaagaacgg tcagtttagg agcaggggca   120
aaagatgagt tacacatcgt agaggcagaa gcaatgaact atgaaggcag tccaattaaa   180
gtaacactgg caactttgaa aatgtctgta caaccaacag tttccctagg gggctttgaa   240
attacaccac ctgtggtctt acggttgaag tgtggttcag ggcctgtgca cattagtgga   300
cagcatctag tagctgtaga ggaagatgca gagtctgaag atgaagatga ggaggacgta   360
aaactcttag gcatgtctgg aaagcgatct gctcctggag gtggtaacaa ggttccacag   420
aaaaaagtaa aacttgatga agatgatgag gacgatgatg aggacgatga ggatgatgag   480
gatgatgatg atgatgattt tgatgaagag gaaactgaag aaaaggtccc agtgaagaaa   540
tctgtacgag atacccccagc caaaaatgca caaaaatcaa accaaaatgg aaaagactta   600
aaaccatcaa caccgagatc aaagggtcaa gagtccttca aaaaacagga aaagactcct   660
aaaacaccaa aaggacctag ttctgtagaa gacattaagg caaaaatgca agcaagtata   720
gaaaaaggcg gttctcttcc caaagtggaa gccaagttca ttaattatgt gaagaattgt   780
ttccggatga ctgaccagga ggctattcaa gatctctggc agtggaggaa atctctttaa   840

<210> SEQ ID NO 63
<211> LENGTH: 774
<212> TYPE: DNA
<213> ORGANISM: Mus musculus

<400> SEQUENCE: 63
```

| | | | | |
|---|---|---|---|---|
| atggaagact | cgatggatat | ggacatgagt | cctcttaggc | ctcagaacta | ccttttcggc | 60 |
| tgtgaactaa | aggctgacaa | agactatcac | tttaaagtgg | ataatgatga | aaatgagcac | 120 |
| cagttgtcat | taagaacggt | cagtttagga | gcaggggcaa | agatgagtt | acacatcgta | 180 |
| gaggcagaag | caatgaacta | tgaaggcagt | ccaattaaag | taacactggc | aactttgaaa | 240 |
| atgtctgtac | aaccaacagt | ttccctaggg | ggctttgaaa | ttacaccacc | tgtggtctta | 300 |
| cggttgaagt | gtggttcagg | gcctgtgcac | attagtggac | agcatctagt | agctgtagag | 360 |
| gaagatgcag | agtctgaaga | tgaagatgag | gaggacgtaa | aactcttagg | catgtctgga | 420 |
| aagcgatctg | ctcctggagg | tggtaacaag | gttccacaga | aaaaagtaaa | acttgatgaa | 480 |
| gatgatgagg | acgatgatga | ggacgatgag | gatgatgagg | atgatgatga | tgatgatttt | 540 |
| gatgaagagg | aaactgaaga | aaaggtccca | gtgaagaaat | ctgtacgaga | taccccagcc | 600 |
| aaaaatgcac | aaaaatcaaa | ccaaaatgga | aaagacttaa | aaccatcaac | accgagatca | 660 |
| aagggtcaag | agtccttcaa | aaacaggaa | aagactccta | aaacaccaaa | aggacctagt | 720 |
| tctgtagaag | acattaaggc | aaaaatgcaa | gcaagtatag | aaaaagcgca | ttga | 774 |

<210> SEQ ID NO 64
<211> LENGTH: 1185
<212> TYPE: DNA
<213> ORGANISM: Mus musculus

<400> SEQUENCE: 64

| | | | | |
|---|---|---|---|---|
| atgtcgggcg | aagacgagca | gcaggagcaa | actatcgccg | aggacctggt | cgtgaccaag | 60 |
| tataagatgg | ggggcgacat | cgccaaccgg | gtgcttcgat | ctttggtgga | ggcttccagc | 120 |
| tcaggtgtgt | ctgtgctgag | cttgtgtgag | aaaggtgatg | ccatgattat | ggaagagaca | 180 |
| gggaagatct | tcaagaagga | aaaggagatg | aagaaaggta | ttgccttttcc | taccagcatt | 240 |
| tccgtaaaata | actgtgtgtg | tcacttctcc | cctttgaaga | gtgaccagga | ctatatactc | 300 |
| aaggaaggtg | acttggtaaa | aattgacctt | ggggttcatg | tggatggctt | cattgccaat | 360 |
| gtggctcaca | cttttgtaat | tggtgtagct | caggggaccc | aggtaacagg | gcggaaagca | 420 |
| gatgtcatta | aggccgctca | cctatgtgct | gaagctgcct | tacgactggt | caaacctgga | 480 |
| aaccagaaca | cacaagtgac | tgaagcatgg | aacaaggttg | ctcactcatt | taactgcaca | 540 |
| ccaatagaag | gtatgctgtc | acaccaattg | aagcagcatg | tgattgatgg | agagaagacg | 600 |
| attatccaga | accctacaga | ccagcagaag | aaggaccatg | aaaaggcaga | atttgaggtg | 660 |
| catgaggttt | atgctgtaga | tgtcctcgtc | agctcaggag | aaggcaaggc | caaagatgca | 720 |
| ggacagagaa | ccaccatcta | caagcgagac | ccctctaaac | aatatggcct | gaaaatgaaa | 780 |
| acttcacgtg | ccttttttcag | tgaggtggaa | cggcgttttg | atgccatgcc | gtttacttta | 840 |
| agagcatttg | aagatgagaa | gaaggctcga | atgggtgtgg | tagagtgtgc | caaacatgag | 900 |
| ttactacagc | catttaacgt | tctctatgag | aaggaggggta | aatttgttgc | ccagtttaaa | 960 |
| tttacagttc | tactcatgcc | caacggcccc | atgcggataa | ccagtggtcc | ctttgagcct | 1020 |
| gacctgtaca | agtctgagat | ggaggttcaa | gatgcagagc | tgaaggctct | tctccagagt | 1080 |
| tctgcaagta | gaaaaaccca | gaaaagaag | aaaagaaggg | cctccaagac | tgtagagaat | 1140 |
| gccaccagtg | gagaaaacctt | agaagagaat | ggagctgggg | actga | 1185 |

<210> SEQ ID NO 65
<211> LENGTH: 465
<212> TYPE: DNA

<213> ORGANISM: Mus musculus

<400> SEQUENCE: 65

| | | | | | | |
|---|---|---|---|---|---|---|
| atggcgcagt | cgattaacat | cacggagctg | aatctgccac | aactggaaat | gctcaagaac | 60 |
| cagctggacc | aggaagtgga | gttttttgtcc | acgtccattg | ctcagctcaa | ggtggtccag | 120 |
| accaagtacg | tggaagccaa | ggactgtctg | aacgtgctga | acaagagcaa | cgagggaaaa | 180 |
| gaattactgg | tcccactgac | gagttctatg | tacgtccccg | ggaagctaca | cgatgtggag | 240 |
| catgtgctta | ttgatgtggg | aaccggctac | tacgtggaga | gacagctgga | ggacgccaag | 300 |
| gacttcttca | aaaggaagat | agacttcctc | accaaacaga | tggagaaaat | ccagccagcg | 360 |
| ctgcaggaga | agcatgccat | gaagcaggct | gtcatggaaa | tgatgagcca | gaagattcag | 420 |
| cagctcacag | ccctgggggc | agcgcaggcc | acggtcaaag | cctga | | 465 |

<210> SEQ ID NO 66
<211> LENGTH: 1329
<212> TYPE: DNA
<213> ORGANISM: Mus musculus

<400> SEQUENCE: 66

| | | | | | | |
|---|---|---|---|---|---|---|
| atgcaggaaa | tgaatctgct | gccgacgccc | gagagtccag | tgactcggca | ggagaagatg | 60 |
| gcgaccgtgt | gggatgaagc | tgagcaagat | ggcattgggg | aggaggtgct | caagatgtcc | 120 |
| acggaagaga | ttgtccagcg | cacacggctg | ttagacagcg | agatcaagat | catgaagagt | 180 |
| gaagtattgc | gagtcaccca | tgaactccaa | gccatgaaag | acaaaatcaa | agagaacagt | 240 |
| gagaaaatca | aagtgaacaa | aaccctgccg | taccttgtct | ccaatgtcat | cgagttgctg | 300 |
| gacgttgacc | ccaatgacca | ggaggaggat | ggtgccaaca | ttgacctgga | ctctcagagg | 360 |
| aagggcaagt | gtgcggtgat | caaaacttct | acccgacaga | catacttcct | gccagtgatt | 420 |
| gggttggtgg | atgcagaaaa | gctgaagcca | ggagacctgg | tgggtgtgaa | caaagactcc | 480 |
| tatctgatcc | tggagaccct | gcccactgaa | tatgactctc | gggtgaaggc | catggaggtg | 540 |
| gacgagcggc | ccacggagca | atacagtgac | atcgggggcc | tggacaagca | gatccaggag | 600 |
| ctggtggaag | ccattgtctt | gcctatgaac | acaaagagaa | agtttgagaa | cttgggtatc | 660 |
| cagccccaa | aaggagtgct | gatgtatggg | ccgcctggaa | cagggaagac | tctgcttgcc | 720 |
| cgagcctgtg | ctgctcagac | caaggccacc | ttcttgaagc | tggcaggccc | tcagctggta | 780 |
| cagatgtttta | ttggagatgg | cgccaagctg | gtccgtgatg | cttttgccct | ggccaaggag | 840 |
| aaggcaccat | ctattatttt | catagacgaa | ttggatgcca | ttggtaccaa | acgcttcgac | 900 |
| agtgaaaagg | caggagaccg | agaggtgcag | aggaccatgc | tggagctact | gaaccagctg | 960 |
| gacggctttc | agcccaacac | tcaagtgaag | gtaattgcag | ccactaacag | ggtggacatc | 1020 |
| ctggatccag | ccctgctgcg | ctcaggccgc | ctagaccgca | agattgagtt | tccaatgccc | 1080 |
| aacgaggagg | ccagagccag | aatcatgcag | atccactcac | ggaagatgaa | tgtcagtcct | 1140 |
| gatgtgaact | atgaagagct | ggctcggtgc | actgatgact | tcaatggagc | ccagtgcaag | 1200 |
| gccgtgtgtg | tggaggcggg | tatgatcgca | ttgcgcaggg | gagccacgga | actcactcat | 1260 |
| gaggactaca | tggagggcat | cctggaggtt | caggccaaga | agaaagccaa | cctacaatac | 1320 |
| tatgcctag | | | | | | 1329 |

<210> SEQ ID NO 67
<211> LENGTH: 1395
<212> TYPE: DNA
<213> ORGANISM: Mus musculus

<400> SEQUENCE: 67

```
atggagaccg aacagccaga agaaaccttc cccaacaccg aaaccaatgg tgaatttggt      60
aaacgccctg cagaagatat ggaagaggag caagccttta aagatctag aaatactgat      120
gagatggttg aattgcgcat tttgcttcag agcaagaatg ctggagcagt gattggaaaa      180
ggaggcaaga atattaaggc tctccgtaca gactacaatg ccagtgtttc agtcccagac      240
agcagtggcc ccgagcgcat actgagtatc agtgctgata ttgagacgat ggagaaatt       300
ctgaagaaaa tcatccctac cttggaagag ggcctgcagt tgccatcacc cactgcaacc      360
agccagctcc cgctcgaatc tgatgctgtg aatgcttaa attaccaaca ttataaagga      420
agtgactttg attgcgagtt gagactgttg attcatcaga gtctggcagg aggaataatt      480
ggtgttaaag gtgctaaaat caaagaactt cgagaaaaca ctcagacaac aatcaagctt      540
ttccaggagt gctgccctca ctctactgac agagttgttc ttattggagg aaaacctgat      600
agggttgtag aatgcatcaa gatcatcctt gaccttatat ctgagtctcc catcaaagga      660
cgtgcacaac cttatgatcc caacttttat gatgagacct atgattatgg tggttttaca      720
atgatgtttg atgaccgccg aggacgacct gtgggattcc ccatgagggg aagaggtggt      780
tttgacagaa tgcctcctgg tcggggtggg cgtcccatgc ctccttctag aagagattat      840
gatgatatga gccctcgtcg aggacctcca ccaccaccac ctggtcgagg tggccggggt      900
ggcagcagag cccggaatct gcctcttcct cctccaccac acccagagg gggagatcta      960
atggcttatg acagaagagg aaggcctgga gaccgctatg atggcatggt tgggttcagt      1020
gctgatgaaa cttgggattc tgcaattgac acatggagcc catcagaatg gcaaatggct      1080
tatgaaccac agggtggttc tggatatgac tattcttatg caggggccg tggctcatat      1140
ggtgatcttg gcggacctat tatcactaca caagtaacta ttcccaaaga tttggctgga      1200
tctattattg gcaaaggtgg tcagcggatt aaacaaattc gtcatgaatc tggagcatca      1260
atcaaaattg atgaacctt agaaggatct gaagatcgga tcattaccat tacaggaaca      1320
caggaccaga tacagaacgc acagtatttg ctgcagaaca gtgtgaagca gtatgcagat      1380
gttgaaggat tctaa                                                       1395
```

<210> SEQ ID NO 68
<211> LENGTH: 1392
<212> TYPE: DNA
<213> ORGANISM: Mus musculus

<400> SEQUENCE: 68

```
atggagaccg aacagccaga agaaaccttc cccaacaccg aaaccaatgg tgaatttggt      60
aaacgccctg cagaagatat ggaagaggag caagccttta aagatctag aaatactgat      120
gagatggttg aattgcgcat tttgcttcag agcaagaatg ctggagcagt gattggaaaa      180
ggaggcaaga atattaaggc tctccgtaca gactacaatg ccagtgtttc agtcccagac      240
agcagtggcc ccgagcgcat actgagtatc agtgctgata ttgagacgat ggagaaatt       300
ctgaagaaaa tcatccctac cttggaagag ggcctgcagt tgccatcacc cactgcaacc      360
agccagctcc cgctcgaatc tgatgctgtg aatgcttaa attaccaaca ttataaagga      420
agtgactttg attgcgagtt gagactgttg attcatcaga gtctggcagg aggaataatt      480
ggtgttaaag gtgctaaaat caaagaactt cgagaaaaca ctcagacaac aatcaagctt      540
ttccaggagt gctgccctca ctctactgac agagttgttc ttattggagg aaaacctgat      600
```

```
agggttgtag aatgcatcaa gatcatcctt gaccttatat ctgagtctcc catcaaagga    660
cgtgcacaac ttatgatcc caacttttat gatgagacct atgattatgg tggttttaca    720
atgatgtttg atgaccgccg aggacgacct gtgggattcc ccatgagggg aagaggtggt    780
tttgacagaa tgcctcctgg tcggggtggg cgtcccatgc ctccttctag aagagattat    840
gatgatatga ccctcgtcg aggacctcca ccaccaccac ctggtcgagg tggccggggt    900
ggcagcagag cccggaatct gcctcttcct cctccaccac acccagagg gggagatcta    960 atggcttatg acagaagagg aaggcctgga gaccgctatg atggcatggt tgggttcagt    1020
gctgatgaaa cttgggattc tgcaattgac acatggagcc atcagaatg gcaaatggct    1080 tatgaaccac agggtggttc tggatatgac tattcttatg cagggggccg tggctcatat    1140
ggtgatcttg gcggacctat tatcactaca caagtaacta ttcccaaaga tttggctgga    1200
tctattattg gcaaaggtgg tcagcggatt aaacaaattc gtcatgaatc tggagcatca    1260
atcaaaattg atgaaccttt agaaggatct gaagatcgga tcattaccat tacaggaaca    1320
caggaccaga tacagaacgc acagtatttg ctgcagaaca gtgtgaagca gtattctgga    1380 aagttttct aa    1392
```

<210> SEQ ID NO 69
<211> LENGTH: 1323
<212> TYPE: DNA
<213> ORGANISM: Mus musculus

<400> SEQUENCE: 69

```
atggagaccg aacagccaga agaaaccttc cccaacaccg aaccaatgg tgaatttggt    60 aaacgccctg cagaagatat ggaagaggag caagccttta aagatctag aaatactgat    120 gagatggttg aattgcgcat tttgcttcag agcaagaatg ctggagcagt gattggaaaa    180
ggaggcaaga atattaaggc tctccgtaca gactacaatg ccagtgtttc agtcccagac    240
agcagtggcc ccgagcgcat actgagtatc agtgctgata ttgagacgat ggagaaatt    300 ctgaagaaaa tcatccctac cttggaagag taccaacatt ataaaggaag tgactttgat    360
tgcgagttga gactgttgat tcatcagagt ctggcaggag aataattgg tgttaaaggt    420 gctaaaatca agaacttcg agaaaacact cagacaacaa tcaagctttt ccaggagtgc    480
tgccctcact ctactgacag agttgttctt attggaggaa aacctgatag ggttgtagaa    540
tgcatcaaga tcatccttga ccttatatct gagtctccca tcaaaggacg tgcacaacct    600
tatgatccca actttatga tgagacctat gattatggtg gttttacaat gatgtttgat    660
gaccgccgag gacgacctgt gggattcccc atgaggggaa gaggtggttt tgacagaatg    720
cctcctggtc ggggtgggcg tcccatgcct ccttctagaa gagattatga tgatatgagc    780
cctcgtcgag gacctccacc accaccacct ggtcgaggtg gccggggtgg cagcagagcc    840
cggaatctgc ctcttcctcc tccaccacca cccagagggg gagatctaat ggcttatgac    900
agaagaggaa ggcctggaga ccgctatgat ggcatggttg gttcagtgc tgatgaaact    960 tgggattctg caattgacac atggagccca tcagaatggc aaatggctta tgaaccacag    1020
ggtggttctg gatatgacta ttcttatgca ggggcgtg ctcatatgg tgatcttggc    1080 ggacctatta tcactacaca agtaactatt cccaaagatt ggctggatc tattattggc    1140 aaaggtggtc agcggattaa acaaattcgt catgaatctg gagcatcaat caaaattgat    1200
```

```
gaacctttag aaggatctga agatcggatc attaccatta caggaacaca ggaccagata      1260
cagaacgcac agtatttgct gcagaacagt gtgaagcagt atgcagatgt tgaaggattc      1320
taa                                                                   1323
```

<210> SEQ ID NO 70
<211> LENGTH: 1320
<212> TYPE: DNA
<213> ORGANISM: Mus musculus

<400> SEQUENCE: 70

```
atggagaccg aacagccaga agaaaccttc cccaacaccg aaccaatgg tgaatttggt       60 aaacgccctg cagaagatat ggaagaggag caagccttta aagatctag aaatactgat      120 gagatggttg aattgcgcat tttgcttcag agcaagaatg ctggagcagt gattggaaaa      180
ggaggcaaga atattaaggc tctccgtaca gactacaatg ccagtgtttc agtcccagac      240
agcagtggcc ccgagcgcat actgagtatc agtgctgata ttgagacgat tggagaaatt      300
ctgaagaaaa tcatccctac cttggaagag taccaacatt ataaaggaag tgactttgat      360
tgcgagttga actgttgat tcatcagagt ctggcaggag gaataattgg tgttaaaggt       420
gctaaaatca agaacttcg agaaaacact cagacaacaa tcaagctttt ccaggagtgc      480
tgccctcact ctactgacag agttgttctt attggaggaa acctgatag ggttgtagaa       540 tgcatcaaga tcatccttga cctatatct gagtctccca tcaaaggacg tgcacaacct       600
tatgatccca actttatga tgagacctat gattatggtg ttttacaat gatgtttgat       660 gaccgccgag gacgacctgt gggattcccc atgagggaa gaggtggttt tgacagaatg      720
cctcctggtc gggtgggcg tcccatgcct ccttctagaa gagattatga tgatatgagc      780
cctcgtcgag gacctccacc accaccacct ggtcgaggtg gccggggtgg cagcagagcc      840
cggaatctgc ctcttcctcc tccaccacca cccagagggg gagatctaat ggcttatgac      900
agaagaggaa ggcctggaga ccgctatgat ggcatggttg ggttcagtgc tgatgaaact      960
tgggattctg caattgacac atggagccca tcagaatggc aaatggctta tgaaccacag     1020
ggtggttctg gatatgacta ttcttatgca gggggccgtg gctcatatgg tgatcttggc     1080
ggacctatta tcactacaca agtaactatt cccaaagatt tggctggatc tattattggc     1140
aaaggtggtc agcggattaa acaaattcgt catgaatctg gagcatcaat caaaattgat      1200
gaacctttag aaggatctga agatcggatc attaccatta caggaacaca ggaccagata     1260
cagaacgcac agtatttgct gcagaacagt gtgaagcagt attctggaaa gttttctaa     1320
```

<210> SEQ ID NO 71
<211> LENGTH: 1380
<212> TYPE: DNA
<213> ORGANISM: Mus musculus

<400> SEQUENCE: 71

```
atggagaccg aacagccaga agaaaccttc cccaacaccg aaccaatgg tgaatttggt       60 aaacgccctg cagaagatat ggaagaggag caagccttta aagatctag aaatactgat      120 gagatggttg aattgcgcat tttgcttcag agcaagaatg ctggagcagt gattggaaaa      180
ggaggcaaga atattaaggc tctccgtaca gactacaatg ccagtgtttc agtcccagac      240
agcagtggcc ccgagcgcat actgagtatc agtgctgata ttgagacgat tggagaaatt      300
ctgaagaaaa tcatccctac cttggaagag ggcctgcagt tgccatcacc cactgcaacc      360
```

-continued

```
agccagctcc cgctcgaatc tgatgctgtg gaatgcttaa attaccaaca ttataaagga    420
agtgactttg attgcgagtt gagactgttg attcatcaga gtctggcagg aggaataatt    480
ggtgttaaag gtgctaaaat caaagaactt cgagaaaaca ctcagacaac aatcaagctt    540
ttccaggagt gctgccctca ctctactgac agagttgttc ttattggagg aaaacctgat    600
agggttgtag aatgcatcaa gatcatcctt gaccttatat ctgagtctcc catcaaagga    660
cgtgcacaac cttatgatcc caacttttat gatgagacct atgattatgg tggttttaca    720
atgatgtttg atgaccgccg aggacgacct gtgggattcc ccatgagggg aagaggtggt    780
tttgacagaa tgcctcctgg tcggggtggg cgtcccatgc ctccttctag aagagattat    840
gatgatatga gccctcgtcg aggacctcca ccaccaccac ctggtcgagg tggccggggt    900
ggcagcagag cccggaatct gcctcttcct cctccaccac cacccagagg gggagatcta    960
atggcttatg acagaagagg aaggcctgga gaccgctatg atggcatggt tgggttcagt   1020
gctgatgaaa cttgggattc tgcaattgac acatggagcc catcagaatg gcaaatggct   1080
tatgaaccac agggtggttc tggatatggg ggccgtggct catatggtga tcttggcgga   1140
cctattatca ctacacaagt aactattccc aaagatttgg ctggatctat tattggcaaa   1200
ggtggtcagc ggattaaaca aattcgtcat gaatctggag catcaatcaa aattgatgaa   1260
cctttagaag gatctgaaga tcggatcatt accattacag gaacacagga ccagatacag   1320
aacgcacagt atttgctgca gaacagtgtg aagcagtatg cagatgttga aggattctaa   1380
```

<210> SEQ ID NO 72
<211> LENGTH: 1377
<212> TYPE: DNA
<213> ORGANISM: Mus musculus

<400> SEQUENCE: 72

```
atggagaccg aacagccaga agaaaccttc cccaacaccg aaaccaatgg tgaatttggt     60
aaacgccctg cagaagatat ggaagaggag caagccttta aaagatctag aaatactgat    120
gagatggttg aattgcgcat tttgcttcag agcaagaatg ctggagcagt gattggaaaa    180
ggaggcaaga atattaaggc tctccgtaca gactacaatg ccagtgtttc agtcccagac    240
agcagtggcc ccgagcgcat actgagtatc agtgctgata ttgagacgat tggagaaatt    300
ctgaagaaaa tcatccctac cttggaagag ggcctgcagt tgccatcacc cactgcaacc    360
agccagctcc cgctcgaatc tgatgctgtg gaatgcttaa attaccaaca ttataaagga    420
agtgactttg attgcgagtt gagactgttg attcatcaga gtctggcagg aggaataatt    480
ggtgttaaag gtgctaaaat caaagaactt cgagaaaaca ctcagacaac aatcaagctt    540
ttccaggagt gctgccctca ctctactgac agagttgttc ttattggagg aaaacctgat    600
agggttgtag aatgcatcaa gatcatcctt gaccttatat ctgagtctcc catcaaagga    660
cgtgcacaac cttatgatcc caacttttat gatgagacct atgattatgg tggttttaca    720
atgatgtttg atgaccgccg aggacgacct gtgggattcc ccatgagggg aagaggtggt    780
tttgacagaa tgcctcctgg tcggggtggg cgtcccatgc ctccttctag aagagattat    840
gatgatatga gccctcgtcg aggacctcca ccaccaccac ctggtcgagg tggccggggt    900
ggcagcagag cccggaatct gcctcttcct cctccaccac cacccagagg gggagatcta    960
atggcttatg acagaagagg aaggcctgga gaccgctatg atggcatggt tgggttcagt   1020
gctgatgaaa cttgggattc tgcaattgac acatggagcc catcagaatg gcaaatggct   1080
tatgaaccac agggtggttc tggatatggg ggccgtggct catatggtga tcttggcgga   1140
```

| | |
|---|---|
| cctattatca ctacacaagt aactattccc aaagatttgg ctggatctat tattggcaaa | 1200 |
| ggtggtcagc ggattaaaca aattcgtcat gaatctggag catcaatcaa aattgatgaa | 1260 |
| cctttagaag gatctgaaga tcggatcatt accattacag gaacacagga ccagatacag | 1320 |
| aacgcacagt atttgctgca gaacagtgtg aagcagtatt ctggaaagtt tttctaa | 1377 |

<210> SEQ ID NO 73
<211> LENGTH: 621
<212> TYPE: DNA
<213> ORGANISM: Homo sapiens

<400> SEQUENCE: 73

| | |
|---|---|
| atgcgacgga caggcgcacc cgctcaggct gactctcggg ggcgaggtcg agccaggggc | 60 |
| ggctgccctg ggggcgaggc gacgctgtct caacctccac ctcgcggcgg aacccgagga | 120 |
| caggagcctc agatgaaaga acaatcatg aaccaggaaa aactcgccaa actgcaggca | 180 |
| caagtgcgca ttggtgggaa aggaactgct cgcagaaaga gaaggtggt tcatagaaca | 240 |
| gccacagcag atgacaaaaa acttcagttc tccttaaaga agttaggggt aaacaatatc | 300 |
| tctggtattg aagaggtgaa tatgtttaca aaccaaggaa cagtgatcca ctttaacaac | 360 |
| cctaaagttc aggcatctct ggcagcgaac actttcacca ttacaggcca tgctgagaca | 420 |
| aagcagctga cagaaatgct acccagcatc ttaaaccagc ttggtgcgga tagtctgact | 480 |
| agtttaagga gactggccga agctctgccc aaacaatctg tggatggaaa agcaccactt | 540 |
| gctactggag aggatgatga tgatgaagtt ccagatcttg tggagaattt tgatgaggct | 600 |
| tccaagaatg aggcaaactg a | 621 |

<210> SEQ ID NO 74
<211> LENGTH: 489
<212> TYPE: DNA
<213> ORGANISM: Homo sapiens

<400> SEQUENCE: 74

| | |
|---|---|
| atgaaagaaa caatcatgaa ccaggaaaaa ctcgccaaac tgcaggcaca agtgcgcatt | 60 |
| ggtgggaaag gaactgctcg cagaaagaag aaggtggttc atagaacagc cacagcagat | 120 |
| gacaaaaaac ttcagttctc cttaaagaag ttagggtaa acaatatctc tggtattgaa | 180 |
| gaggtgaata tgtttacaaa ccaaggaaca gtgatccact taacaaccc taaagttcag | 240 |
| gcatctctgg cagcgaacac tttcaccatt acaggccatg ctgagacaaa gcagctgaca | 300 |
| gaaatgctac ccagcatctt aaaccagctt ggtgcggata gtctgactag tttaaggaga | 360 |
| ctggccgaag ctctgcccaa acaatctgtg gatggaaaag caccacttgc tactggagag | 420 |
| gatgatgatg atgaagttcc agatcttgtg gagaattttg atgaggcttc caagaatgag | 480 |
| gcaaactga | 489 |

<210> SEQ ID NO 75
<211> LENGTH: 3144
<212> TYPE: DNA
<213> ORGANISM: Homo sapiens

<400> SEQUENCE: 75

| | |
|---|---|
| atggctgtga ctctggacaa agacgcttat tatcggcgag tgaagagact gtacagcaat | 60 |
| tggcggaaag gagaagatga gtatgccaac gttgatgcca ttgttgtatc agtgggtgtt | 120 |
| gatgaagaaa ttgtttatgc caaatcaact gccttacaga catggctctt tggttatgaa | 180 |

```
ctaactgata ctatcatggt cttttgtgat gacaaaatca tctttatggc cagcaagaaa    240
aaagtggagt tcttgaaaca gattgccaac actaagggca atgagaatgc taatggagcc    300
cctgccatca cactgctaat acgagaaaag aatgaaagta ataagagtag ctttgacaaa    360
atgattgaag ccattaaaga aagcaagaat ggcaagaaga ttggagtgtt cagcaaagac    420
aaattccctg gagagttcat gaagagctgg aatgactgcc tcaacaaaga aggctttgac    480
aaaatagata tcagtgcagt tgtggcatat accatcgctg taaaggagga tggggagctc    540
aacctaatga agaaagcagc cagcatcact tctgaagtct tcaacaaatt cttcaaggaa    600
agagtcatgg aaatagttga tgcagatgag aaagttcgac acagcaaact ggctgagtct    660
gtggaaaagg ccattgaaga gaaaaatac cttgctgggg cagacccttc tactgtggaa     720
atgtgttacc ctcctatcat tcagagtggt ggcaactata atctcaagtt cagtgtggtg    780
agtgacaaga atcatatgca ctttggggct atcacttgtg ccatgggtat tcgcttcaag    840
tcttactgct ccaaccttgt tcgcactttg atggttgatc cttctcaaga agttcaagaa    900
aattataact ttttgctcca gcttcaagag gagctgctga aggaattaag acatggtgtg    960
aagatatgtg acgtgtataa cgctgtcatg gacgtggtta aaaagcagaa gccagaactg   1020
ctgaacaaaa ttaccaaaaa cctagggttt gggatgggaa ttgaattccg tgaaggctcc   1080
ctagtaatca atagcaaaaa tcaatacaaa ctgaagaaag gaatggtttt cagcatcaat   1140
ttaggattct cagacctgac taacaaggag gggaaaaagc cagaagagaa aacctatgcc   1200
ctgttcattg gtgacacagt gcttgtggat gaggatggcc cagctactgt tctcacttct   1260
gtgaagaaga agtgaagaa tgtgggattt ttcctaaaga atgaagatga ggaagaagag   1320
gaggaggaga agatgaggc agaggacctt tgggaagag gttctcgggc agcattactt    1380
acagaaagaa caagaaatga aatgactgca gaagagaagc gaagagcaca tcagaaagaa   1440
ctagcggctc aactcaatga agaagcaaag aggcgattga ctgaacaaaa gggagaacag   1500
cagattcaga aagctcgcaa gtctaatgtg tcctataaaa acccatctct gatgcctaag   1560
gaaccacata ttcgggaaat gaagatctac atcgataaga aatatgagac tgtaataatg   1620
cccgtgtttg gcattgcaac accgtttcac attgccacaa tcaagaatat aagtatgtcc   1680
gtggaaggag attatactta cttgcgaatc aacttttatt gcccaggcag tgctctgggc   1740
aggaatgaag gcaacatctt tcctaaccct gaagcgactt ttgtcaagga aattacatac   1800
cgagcatcaa atattaaggc acccggagaa cagacagtac cagccttgaa ccttcagaat   1860
gctttccgaa ttattaaaga agtacagaaa cgttataaaa ctcgagaagc tgaagagaaa   1920
gagaaggagg ggattgtaaa acaagactca ctggtgatca atctaaaccg gagtaatccg   1980
aaactgaaag atctatacat tcgcccaaat attgcccaaa agaggatgca aggctcactg   2040
gaggcccatg tcaatggctt ccgcttcaca tctgttcgag agacaaagt ggatattttg    2100
tacaataata ttaagcatgc tttgttccag ccctgtgatg agaaatgat tattgtcttg   2160
cactttcacc tcaagaatgc catcatgttt gggaagaagc ggcacacgga tgtgcagttc   2220
tacacagaag tgggagagat aaccacggac ttggggaaac atcagcatat gcatgaccga   2280
gatgacctct atgctgagca gatggaacga gaaatgaggc acaaactgaa aacagccttt   2340
aaaaatttca ttgagaaagt agaggctcta actaaggagg aactggaatt tgaagtgcct   2400
tttagggact tgggatttaa cggagctccc tataggagta cctgcctcct tcagcccact   2460
agtagtcgcg tggtaaatgc tacgaatgg ccacctttg tggtgacatt ggatgaggta    2520
gagctgatcc actttgagcg ggtccagttt cacctgaaga actttgatat ggtaatcgtc   2580
```

```
tacaaggact acagcaagaa agtgaccatg atcaacgcca ttcctgtagc ctctcttgac    2640
cccatcaagg aatggttgaa ttcctgcgac ctgaaataca cagaaggagt acagtccctc    2700
aactggacta aaatcatgaa gaccattgtt gatgaccctg agggcttctt cgaacaaggt    2760
ggctggtctt tcctggagcc tgagggtgag gggagtgatg ctgaagaagg ggattcagag    2820
tctgaaattg aagatgagac ttttaatcct tcagaagatg actatgaaga ggaagaggag    2880
gacagtgatg aagattattc atcagaagca gaagagtcag actattctaa ggagtcattg    2940
ggtagtgaag aagagagtgg aaaggattgg gatgaactgg aggaagaagc ccgaaaagcg    3000
gaccgagaaa gtcgttacga ggaagaagaa aacaaagtc gaagtatgag ccggaagagg     3060
aaggcatctg tgcacagttc gggccgtggc tctaaccgtg gttccagaca cagctctgca    3120 cccccaaga aaagaggaa gtaa                                              3144

<210> SEQ ID NO 76
<211> LENGTH: 975
<212> TYPE: DNA
<213> ORGANISM: Homo sapiens

<400> SEQUENCE: 76
atgagcagcg aggccgagac ccagcagccg cccgccgccc ccccgccgc cccgcccctc       60 agcgccgccg acaccaagcc cggcactacg ggcagcggcg cagggagcgg tggcccgggc     120
ggcctcacat cggcggcgcc tgccggcggg acaagaagg tcatcgcaac gaaggttttg      180
ggaacagtaa aatggttcaa tgtaaggaac ggatatggtt tcatcaacag gaatgacacc    240
aaggaagatg tatttgtaca ccagactgcc ataaagaaga ataaccccag gaagtacctt    300
cgcagtgtag agatggagag gactgtggag tttgatgttg ttgaaggaga aaagggtgcg    360
gaggcagcaa atgttacagg tcctggtggt gttccagttc aaggcagtaa atatgcagca    420
gaccgtaacc attatagacg ctatccacgt cgtaggggtc ctccacgcaa ttaccagcaa    480
aattaccaga atagtgagag tggggaaaag aacgagggat cggagagtgc tcccgaaggc    540
caggcccaac aacgccggcc ctaccgcagg cgaaggttcc caccttacta catgcggaga    600
ccctatgggc gtcgaccaca gtattccaac cctcctgtgc agggagaagt gatggagggt    660
gctgacaacc agggtgcagg agaacaaggt agaccagtga ggcagaatat gtatcgggga    720
tatagaccac gattccgcag gggccctcct cgccaaagac agcctagaga ggacggcaat    780
gaagaagata agaaaaatca aggagatgag acccaaggtc agcagccacc tcaacgtcgg    840
taccgccgca acttcaatta ccgacgcaga cgccagaaaa accctaaacc acaagatggc    900
aaagagacaa aagcagccga tccaccagct gagaattcgt ccgctcccga ggctgagcag    960
ggcggggctg agtaa                                                      975

<210> SEQ ID NO 77
<211> LENGTH: 885
<212> TYPE: DNA
<213> ORGANISM: Homo sapiens

<400> SEQUENCE: 77
atggaagatt cgatggacat ggacatgagc cccctgaggc cccagaacta tcttttcggt      60
tgtgaactaa aggccgacaa agattatcac tttaaggtgg ataatgatga aaatgagcac    120
cagttatctt taagaacggt cagtttaggg gctggtgcaa aggatgagtt gcacattgtt    180
gaagcagagg caatgaatta cgaaggcagt ccaattaaag taacactggc aactttgaaa    240
```

```
atgtctgtac agccaacggt ttcccttggg ggctttgaaa taacaccacc agtggtctta    300
aggttgaagt gtggttcagg gccagtgcat attagtggac agcacttagt agctgtggag    360
gaagatgcag agtcagaaga tgaagaggag gaggatgtga aactcttaag tatatctgga    420
aagcggtctg cccctggagg tggtagcaag gttccacaga aaaaagtaaa acttgctgct    480
gatgaagatg atgacgatga tgatgaagag gatgatgatg aagatgatga tgatgatgat    540
tttgatgatg aggaagctga agaaaaagcg ccagtgaaga aatctatacg agatactcca    600
gccaaaaatg cacaaaagtc aaatcagaat ggaaaagact caaaaccatc atcaacacca    660
agatcaaaag gacaagaatc cttcaagaaa caggaaaaaa ctcctaaaac accaaaagga    720
cctagttctg tagaagacat taaagcaaaa atgcaagcaa gtatagaaaa aggtggttct    780
cttcccaaag tggaagccaa attcatcaat tatgtgaaga attgcttccg gatgactgac    840
caagaggcta ttcaagatct ctggcagtgg aggaagtctc tttaa    885
```

<210> SEQ ID NO 78
<211> LENGTH: 798
<212> TYPE: DNA
<213> ORGANISM: Homo sapiens

<400> SEQUENCE: 78

```
atggaagatt cgatggacat ggacatgagc cccctgaggc cccagaacta tcttttcggt    60
tgtgaactaa aggccgacaa agattatcac tttaaggtgg ataatgatga aaatgagcac    120
cagttatctt taagaacggt cagtttaggg gctggtgcaa aggatgagtt gcacattgtt    180
gaagcagagg caatgaatta cgaaggcagt ccaattaaag taacactggc aactttgaaa    240
atgtctgtac agccaacggt ttcccttggg ggctttgaaa taacaccacc agtggtctta    300
aggttgaagt gtggttcagg gccagtgcat attagtggac agcacttagt agctgtggag    360
gaagatgcag agtcagaaga tgaagaggag gaggatgtga aactcttaag tatatctgga    420
aagcggtctg cccctggagg tggtagcaag gttccacaga aaaaagtaaa acttgctgct    480
gatgaagatg atgacgatga tgatgaagag gatgatgatg aagatgatga tgatgatgat    540
tttgatgatg aggaagctga agaaaaagcg ccagtgaaga aaggacaaga atccttcaag    600
aaacaggaaa aaactcctaa acaccaaaa ggacctagtt ctgtagaaga cattaaagca    660
aaaatgcaag caagtataga aaaggtggt tctcttccca agtggaagc caaattcatc    720 aattatgtga agaattgctt ccggatgact gaccaagagg ctattcaaga tctctggcag    780
tggaggaagt ctctttaa    798
```

<210> SEQ ID NO 79
<211> LENGTH: 780
<212> TYPE: DNA
<213> ORGANISM: Homo sapiens

<400> SEQUENCE: 79

```
atggaagatt cgatggacat ggacatgagc cccctgaggc cccagaacta tcttttcggt    60
tgtgaactaa aggccgacaa agattatcac tttaaggtgg ataatgatga aaatgagcac    120
cagttatctt taagaacggt cagtttaggg gctggtgcaa aggatgagtt gcacattgtt    180
gaagcagagg caatgaatta cgaaggcagt ccaattaaag taacactggc aactttgaaa    240
atgtctgtac agccaacggt ttcccttggg ggctttgaaa taacaccacc agtggtctta    300
aggttgaagt gtggttcagg gccagtgcat attagtggac agcacttagt agctgtggag    360
gaagatgcag agtcagaaga tgaagaggag gaggatgtga aactcttaag tatatctgga    420
```

```
aagcggtctg cccctggagg tggtagcaag gttccacaga aaaagtaaa acttgctgct      480 gatgaagatg atgacgatga tgatgaagag gatgatgatg aagatgatga tgatgatgat      540
tttgatgatg aggaagctga agaaaaagcg ccagtgaaga aatctatacg agatactcca      600
gccaaaaatg cacaaaagtc aaatcagaat ggaaaagact caaaaccatc atcaacacca      660
agatcaaaag gacaagaatc cttcaagaaa caggaaaaaa ctcctaaaac accaaaagga      720
cctagttctg tagaagacat taaagcaaaa atgcaagcaa gtatagaaaa agcgcattga      780
```

<210> SEQ ID NO 80
<211> LENGTH: 693
<212> TYPE: DNA
<213> ORGANISM: Homo sapiens

<400> SEQUENCE: 80

```
atgaattacg aaggcagtcc aattaaagta acactggcaa ctttgaaaat gtctgtacag       60
ccaacggttt cccttggggg ctttgaaata caccaccag tggtcttaag gttgaagtgt      120
ggttcagggc cagtgcatat tagtggacag cacttagtag ctgtggagga agatgcagag      180
tcagaagatg aagaggagga ggatgtgaaa ctcttaagta tatctggaaa gcggtctgcc      240
cctggaggtg gtagcaaggt tccacagaaa aagtaaaac ttgctgctga tgaagatgat      300
gacgatgatg atgaagagga tgatgatgaa gatgatgatg atgatgattt tgatgatgag      360
gaagctgaag aaaaagcgcc agtgaagaaa tctatacgag atactccagc caaaaatgca      420
caaaagtcaa atcagaatgg aaaagactca aaaccatcat caacaccaag atcaaaagga      480
caagaatcct tcaagaaaca ggaaaaaact cctaaaacac caaaaggacc tagttctgta      540
gaagacatta aagcaaaaat gcaagcaagt atagaaaaag tggttctct cccaaagtg      600 gaagccaaat tcatcaatta tgtgaagaat tgcttccgga tgactgacca agaggctatt      660
caagatctct ggcagtggag gaagtctctt taa                                  693
```

<210> SEQ ID NO 81
<211> LENGTH: 693
<212> TYPE: DNA
<213> ORGANISM: Homo sapiens

<400> SEQUENCE: 81

```
atggaagatt cgatggacat ggacatgagc cccctgaggc cccagaacta tcttttcggt       60
tgtgaactaa aggccgacaa agattatcac tttaaggtgg ataatgatga aaatgagcac      120
cagttatctt taagaacggt cagtttaggg gctggtgcaa aggatgagtt gcacattgtt      180
gaagcagagg caatgaatta cgaaggcagt ccaattaaag taacactggc aactttgaaa      240
atgtctgtac agccaacggt ttcccttggg gctttgaaa taacaccacc agtggtctta      300
aggttgaagt gtggttcagg gccagtgcat attagtggac agcacttagt agctgtggag      360
gaagatgcag agtcagaaga tgaagaggag gaggatgtga aactcttaag tatatctgga      420
aagcggtctg cccctggagg tggtagcaag gttccacaga aaaagtaaa acttgctgct      480 gatgaagatg atgacgatga tgatgaagag gatgatgatg aagatgatga tgatgatgat      540
tttgatgatg aggaagctga agaaaaagcg ccagtgaaga aggacaaga atccttcaag      600 aaacaggaaa aaactcctaa aacaccaaaa ggacctagtt ctgtagaaga cattaaagca      660
aaaatgcaag caagtataga aaaagcgcat tga                                   693
```

<210> SEQ ID NO 82

<211> LENGTH: 504
<212> TYPE: DNA
<213> ORGANISM: Homo sapiens

<400> SEQUENCE: 82

| | | | | | |
|---|---|---|---|---|---|
| atggaagatt | cgatggacat | ggacatgagc | cccctgaggc | cccagaacta | tcttttcgct | 60 |
| gtggaggaag | atgcagagtc | agaagatgaa | gaggaggagg | atgtgaaact | cttaagtata | 120 |
| tctggaaagc | ggtctgcccc | tggaggtggt | agcaaggttc | cacagaaaaa | agtaaaactt | 180 |
| gctgctgatg | aagatgatga | cgatgatgat | gaagaggatg | atgatgaaga | tgatgatgat | 240 |
| gatgattttg | atgatgagga | agctgaagaa | aaagcgccag | tgaagaaagg | acaagaatcc | 300 |
| ttcaagaaac | aggaaaaaac | tcctaaaaca | ccaaaaggac | ctagttctgt | agaagacatt | 360 |
| aaagcaaaaa | tgcaagcaag | tatagaaaaa | ggtggttctc | ttcccaaagt | ggaagccaaa | 420 |
| ttcatcaatt | atgtgaagaa | ttgcttccgg | atgactgacc | aagaggctat | tcaagatctc | 480 |
| tggcagtgga | ggaagtctct | ttaa | | | | 504 |

<210> SEQ ID NO 83
<211> LENGTH: 1185
<212> TYPE: DNA
<213> ORGANISM: Homo sapiens

<400> SEQUENCE: 83

| | | | | | |
|---|---|---|---|---|---|
| atgtcgggcg | aggacgagca | acaggagcaa | actatcgctg | aggacctggt | cgtgaccaag | 60 |
| tataagatgg | ggggcgacat | cgccaacagg | gtacttcggt | ccttggtgga | agcatctagc | 120 |
| tcaggtgtgt | cggtactgag | cctgtgtgag | aaaggtgatg | ccatgattat | ggaagaaaca | 180 |
| gggaaaatct | tcaagaaaga | aaaggaaatg | aagaaaggta | ttgcttttcc | caccagcatt | 240 |
| tcggtaaata | actgtgtatg | tcacttctcc | cctttgaaga | gcgaccagga | ttatattctc | 300 |
| aaggaaggtg | acttggtaaa | aattgacctt | ggggtccatg | tggatggctt | catcgctaat | 360 |
| gtagctcaca | cttttgtggt | tgatgtagct | caggggaccc | aagtaacagg | gaggaaagca | 420 |
| gatgttatta | aggcagctca | ccttttgtgct | gaagctgccc | tacgcctggt | caaacctgga | 480 |
| aatcagaaca | cacaagtgac | agaagcctgg | aacaaagttg | cccactcatt | taactgcacg | 540 |
| ccaatagaag | gtatgctgtc | acaccagttg | aagcagcatg | tcatcgatgg | agaaaaaacc | 600 |
| attatccaga | tcccacagaa | ccagcagaag | aaggaccatg | aaaaagctga | atttgaggta | 660 |
| catgaagtat | atgctgtgga | tgttctcgtc | agctcaggag | agggcaaggc | caaggatgca | 720 |
| ggacagagaa | ccactatttta | caaacgagac | ccctctaaac | agtatggact | gaaaatgaaa | 780 |
| acttcacgtg | ccttcttcag | tgaggtggaa | aggcgttttg | atgccatgcc | gtttactttta | 840 |
| agagcatttg | aagatgagaa | gaaggctcgg | atgggtgtgg | tggagtgcgc | caaacatgaa | 900 |
| ctgctgcaac | catttaatgt | tctctatgag | aaggagggtg | aatttgttgc | ccagtttaaa | 960 |
| tttacagttc | tgctcatgcc | caatggcccc | atgcggataa | ccagtggtcc | cttcgagcct | 1020 |
| gacctctaca | gtctgagat | ggaggtccag | gatgcagagc | taaaggccct | cctccagagt | 1080 |
| tctgcaagtc | gaaaaaccca | gaaaaagaaa | aaaagaagg | cctccaagac | tgcagagaat | 1140 |
| gccaccagtg | gggaaacatt | agaagaaaat | gaagctgggg | actga | | 1185 |

<210> SEQ ID NO 84
<211> LENGTH: 465
<212> TYPE: DNA
<213> ORGANISM: Homo sapiens -continued

<400> SEQUENCE: 84

```
atggcgcagt ctattaacat cacggagctg aatctgccgc agctagaaat gctcaagaac      60
cagctggacc aggaagtgga gttcttgtcc acgtccattg ctcagctcaa agtggtacag     120
accaagtatg tggaagccaa ggactgtctg aacgtgctga acaagagcaa cgaggggaaa     180
gaattactcg tcccactgac gagttctatg tatgtccctg ggaagctgca tgatgtggaa     240
cacgtgctca tcgatgtggg aactgggtac tatgtagaga agacagctga ggatgccaag     300
gacttcttca agaggaagat agattttcta accaagcaga tggagaaaat ccaaccagct     360
cttcaggaga agcacgccat gaaacaggcc gtcatggaaa tgatgagtca gaagattcag     420
cagctcacag ccctgggggc agctcaggct actgctaagg cctga                     465
```

<210> SEQ ID NO 85
<211> LENGTH: 330
<212> TYPE: DNA
<213> ORGANISM: Homo sapiens

<400> SEQUENCE: 85

```
atggcgcagt ctattaacat cacggagctg aatctgccgc agctagaaat gctcaagaac      60
cagctggacc agatgtatgt ccctgggaag ctgcatgatg tggaacacgt gctcatcgat     120
gtgggaactg gtactatgt agagaagaca gctgaggatg ccaaggactt cttcaagagg     180
aagatagatt ttctaaccaa gcagatggag aaaatccaac cagctcttca ggagaagcac     240
gccatgaaac aggccgtcat ggaaatgatg agtcagaaga ttcagcagct cacagccctg     300
ggggcagctc aggctactgc taaggcctga                                       330
```

<210> SEQ ID NO 86
<211> LENGTH: 1320
<212> TYPE: DNA
<213> ORGANISM: Homo sapiens

<400> SEQUENCE: 86

```
atgaatctgc tgccgaatat tgagagtcca gtgactcggc aggagaagat ggcgaccgtg      60
tgggatgagg ccgagcaaga tggaattggg gaggaggtgc tcaagatgtc cacggaggag     120
atcatccagc gcacacggct gctggacagt gagatcaaga tcatgaagag tgaagtgttg     180
agagtcaccc atgagctcca agccatgaag acaagataa agagaacag tgagaaaatc     240
aaagtgaaca agaccctgcc gtaccttgtc tccaacgtca tcgagctcct ggatgttgat     300
cctaatgacc aagaggagga tggtgccaat attgacctgg actcccagag aagggcaag     360
tgtgctgtga tcaaaacctc tacacgacag acgtacttcc ttcctgtgat tgggttggtg     420
gatgctgaaa agctaaagcc aggagacctg gtgggtgtga caaagactc ctatctgatc     480
ctggagacgc tgcccacaga gtatgactcg cgggtgaagg ccatggaggt agacgagagg     540
cccacggagc aatacagtga cattgggggt ttggacaagc agatccagga gctggtggag     600
gccattgtct tgccaatgaa ccacaaggag aagtttgaga cttggggat ccaacctcca     660
aaaggggtgc tgatgtatgg gcccccaggg acggggaaga ccctcctggc ccgggcctgt     720
gccgcacaga ctaaggccac cttcctaaag ctggctggcc cccagctggt gcagatgttc     780
attggagatg gtgccaagct agtccgggat gcctttgccc tggccaagga aaagcgccc     840
tctatcatct tcattgatga gttggatgcc atcggcacca gcgctttga cagtgagaag     900
gctggggacc gggaggtgca gaggacaatg ctggagcttc tgaaccagct ggatggcttc     960
```

| | |
|---|---|
| cagcccaaca cccaagttaa ggtaattgca gccacaaaca gggtggacat cctggacccc | 1020 |
| gccctcctcc gctcgggccg ccttgaccgc aagatagagt tcccgatgcc caatgaggag | 1080 |
| gcccgggcca gaatcatgca gatccactcc cgaaagatga atgtcagtcc tgacgtgaac | 1140 |
| tacgaggagc tggcccgctg cacagatgac ttcaatgggg cccagtgcaa ggctgtgtgt | 1200 |
| gtggaggcgg gcatgatcgc actgcgcagg ggtgccacgg agctcaccca cgaggactac | 1260 |
| atggaaggca tcctggaggt gcaggccaag aagaaagcca acctacaata ctacgcctag | 1320 |

<210> SEQ ID NO 87
<211> LENGTH: 1395
<212> TYPE: DNA
<213> ORGANISM: Homo sapiens

<400> SEQUENCE: 87

| | |
|---|---|
| atggaaactg aacagccaga agaaaccttc cctaacactg aaaccaatgg tgaatttggt | 60 |
| aaacgccctg cagaagatat ggaagaggaa caagcattta aagatctag aaacactgat | 120 |
| gagatggttg aattacgcat tctgcttcag agcaagaatg ctggggcagt gattggaaaa | 180 |
| ggaggcaaga atattaaggc tctccgtaca gactacaatg ccagtgtttc agtcccagac | 240 |
| agcagtggcc ccgagcgcat attgagtatc agtgctgata ttgaaacaat ggagaaatt | 300 |
| ctgaagaaaa tcatccctac cttggaagag ggcctgcagt tgccatcacc cactgcaacc | 360 |
| agccagctcc cgctcgaatc tgatgctgtg aatgcttaa attaccaaca ctataaagga | 420 |
| agtgactttg actgcgagtt gaggctgttg attcatcaga gtctagcagg aggaattatt | 480 |
| ggggtcaaag tgctaaaat caagaacttc gagagaaca ctcaaaccac catcaagctt | 540 |
| ttccaggaat gctgtcctca ttccactgac agagttgttc ttattggagg aaaacccgat | 600 |
| agggttgtag agtgcataaa gatcatcctt gatcttatat ctgagtctcc catcaaagga | 660 |
| cgtgcacagc cttatgatcc caattttac gatgaaacct atgattatgg tggttttaca | 720 |
| atgatgtttg atgaccgtcg cggacgccca gtgggatttc ccatgcgggg aagaggtggt | 780 |
| tttgacagaa tgcctcctgg tcggggtggg cgtcccatgc ctccatctag aagagattat | 840 |
| gatgatatga gccctcgtcg aggaccacct cccctcctc ccggacgagg cggccggggt | 900 |
| ggtagcagag ctcggaatct tcctcttcct ccaccaccac cacctagagg gggagacctc | 960 |
| atggcctatg acagaagagg gagacctgga gaccgttacg acggcatggt tggtttcagt | 1020 |
| gctgatgaaa cttgggactc tgcaatagat acatggagcc catcagaatg gcagatggct | 1080 |
| tatgaaccac agggtggctc cggatatgat tattcctatg caggggtcg tggctcatat | 1140 |
| ggtgatcttg gtgacctat tattactaca caagtaacta ttcccaaaga tttggctgga | 1200 |
| tctattattg gcaaaggtgg tcagcggatt aaacaaatcc gtcatgagtc gggagcttcg | 1260 |
| atcaaaattg atgagccttt agaaggatcc gaagatcgga tcattaccat tacaggaaca | 1320 |
| caggaccaga tacagaatgc acagtatttg ctgcagaaca gtgtgaagca gtatgcagat | 1380 |
| gttgaaggat tctaa | 1395 |

<210> SEQ ID NO 88
<211> LENGTH: 1392
<212> TYPE: DNA
<213> ORGANISM: Homo sapiens

<400> SEQUENCE: 88

| | |
|---|---|
| atggaaactg aacagccaga agaaaccttc cctaacactg aaaccaatgg tgaatttggt | 60 |
| aaacgccctg cagaagatat ggaagaggaa caagcattta aagatctag aaacactgat | 120 |

```
gagatggttg aattacgcat tctgcttcag agcaagaatg ctggggcagt gattggaaaa      180
ggaggcaaga atattaaggc tctccgtaca gactacaatg ccagtgtttc agtcccagac      240
agcagtggcc ccgagcgcat attgagtatc agtgctgata ttgaaacaat tggagaaatt      300
ctgaagaaaa tcatccctac cttggaagag ggcctgcagt tgccatcacc cactgcaacc      360
agccagctcc cgctcgaatc tgatgctgtg aatgcttaa attaccaaca ctataaagga      420
agtgactttg actgcgagtt gaggctgttg attcatcaga gtctagcagg aggaattatt      480
ggggtcaaag gtgctaaaat caaagaactt cgagagaaca ctcaaaccac catcaagctt      540
ttccaggaat gctgtcctca ttccactgac agagttgttc ttattggagg aaaacccgat      600
agggttgtag agtgcataaa gatcatcctt gatcttatat ctgagtctcc catcaaagga      660
cgtgcacagc cttatgatcc aattttttac gatgaaacct atgattatgg tggttttaca      720
atgatgtttg atgaccgtcg cggacgccca gtgggatttc ccatgcgggg aagaggtggt      780
tttgacagaa tgcctcctgg tcggggtggg cgtcccatgc ctccatctag aagagattat      840
gatgatatga gccctcgtcg aggaccacct cccctcctc ccggacgagg cggccgggt       900 ggtagcagag ctcggaatct tcctcttcct ccaccaccac cacctagagg gggagacctc      960
atggcctatg acagaagagg gagacctgga gaccgttacg acggcatggt tggtttcagt     1020
gctgatgaaa cttgggactc tgcaatagat acatggagcc catcagaatg gcagatggct     1080
tatgaaccac agggtggctc cggatatgat tattcctatg caggggggtcg tggctcatat    1140 ggtgatcttg gtgacctat tattactaca caagtaacta ttcccaaaga tttggctgga     1200
tctattattg gcaaaggtgg tcagcggatt aaacaaatcc gtcatgagtc gggagcttcg     1260
atcaaaattg atgagccttt agaaggatcc gaagatcgga tcattaccat tacaggaaca     1320
caggaccaga tacagaatgc acagtatttg ctgcagaaca gtgtgaagca gtattctgga     1380
aagtttttct aa                                                         1392

<210> SEQ ID NO 89
<211> LENGTH: 1320
<212> TYPE: DNA
<213> ORGANISM: Homo sapiens

<400> SEQUENCE: 89
atggaaactg aacagccaga agaaaccttc cctaacactg aaaccaatgg tgaatttggt       60
aaacgccctg cagaagatat ggaagaggaa caagcattta aagatctag aaacactgat       120 gagatggttg aattacgcat tctgcttcag agcaagaatg ctggggcagt gattggaaaa      180
ggaggcaaga atattaaggc tctccgtaca gactacaatg ccagtgtttc agtcccagac      240
agcagtggcc ccgagcgcat attgagtatc agtgctgata ttgaaacaat tggagaaatt      300
ctgaagaaaa tcatccctac cttggaagag taccaacact ataaggaag tgactttgac       360 tgcgagttga ggctgttgat tcatcagagt ctagcaggag gaattattgg ggtcaaaggt      420
gctaaaatca agaacttcg agagaacact caaaccacca tcaagctttt ccaggaatgc      480
tgtcctcatt ccactgacag agttgttctt attggaggaa aacccgatag ggttgtagag      540
tgcataaaga tcatccttga tcttatatct gagtctccca tcaaaggacg tgcacagcct      600
tatgatccca atttttacga tgaaacctat gattatggtg ttttacaat gatgtttgat       660 gaccgtcgcg gacgcccagt gggatttccc atgcggggaa gaggtggttt tgacagaatg      720
cctcctggtc ggggtgggcg tcccatgcct ccatctagaa gagattatga tgatatgagc      780
```

| | |
|---|---|
| cctcgtcgag gaccacctcc ccctcctccc ggacgaggcg gccggggtgg tagcagagct | 840 |
| cggaatcttc ctcttcctcc accaccacca cctagagggg gagacctcat ggcctatgac | 900 |
| agaagaggga gacctggaga ccgttacgac ggcatggttg gtttcagtgc tgatgaaact | 960 |
| tgggactctg caatagatac atggagccca tcagaatggc agatggctta tgaaccacag | 1020 |
| ggtggctccg gatatgatta ttcctatgca ggggtcgtg gctcatatgg tgatcttggt | 1080 |
| ggacctatta ttactacaca agtaactatt cccaaagatt tggctggatc tattattggc | 1140 |
| aaaggtggtc agcggattaa acaaatccgt catgagtcgg gagcttcgat caaaattgat | 1200 |
| gagcctttag aaggatccga agatcggatc attaccatta caggaacaca ggaccagata | 1260 |
| cagaatgcac agtatttgct gcagaacagt gtgaagcagt attctggaaa gttttctaa | 1320 |

<210> SEQ ID NO 90
<211> LENGTH: 1323
<212> TYPE: DNA
<213> ORGANISM: Homo sapiens

<400> SEQUENCE: 90

| | |
|---|---|
| atggaaactg aacagccaga agaaaccttc cctaacactg aaaccaatgg tgaatttggt | 60 |
| aaacgccctg cagaagatat ggaagaggaa caagcattta aagatctag aaacactgat | 120 |
| gagatggttg aattacgcat tctgcttcag agcaagaatg ctggggcagt gattggaaaa | 180 |
| ggaggcaaga atattaaggc tctccgtaca gactacaatg ccagtgtttc agtcccagac | 240 |
| agcagtggcc ccgagcgcat attgagtatc agtgctgata ttgaaacaat tggagaaatt | 300 |
| ctgaagaaaa tcatccctac cttggaagag taccaacact ataaaggaag tgactttgac | 360 |
| tgcgagttga ggctgttgat tcatcagagt ctagcaggag gaattattgg ggtcaaaggt | 420 |
| gctaaaatca agaacttcg agagaacact caaaccacca tcaagctttt ccaggaatgc | 480 |
| tgtcctcatt ccactgacag agttgttctt attggaggaa aacccgatag ggttgtagag | 540 |
| tgcataaaga tcatccttga tcttatatct gagtctccca tcaaaggacg tgcacagcct | 600 |
| tatgatccca ttttttacga tgaaacctat gattatggtg gttttacaat gatgtttgat | 660 |
| gaccgtcgcg gacgcccagt gggatttccc atgcggggaa gaggtggttt tgacagaatg | 720 |
| cctcctggtc ggggtgggcg tcccatgcct ccatctagaa gagattatga tgatatgagc | 780 |
| cctcgtcgag gaccacctcc ccctcctccc ggacgaggcg gccggggtgg tagcagagct | 840 |
| cggaatcttc ctcttcctcc accaccacca cctagagggg gagacctcat ggcctatgac | 900 |
| agaagaggga gacctggaga ccgttacgac ggcatggttg gtttcagtgc tgatgaaact | 960 |
| tgggactctg caatagatac atggagccca tcagaatggc agatggctta tgaaccacag | 1020 |
| ggtggctccg gatatgatta ttcctatgca ggggtcgtg gctcatatgg tgatcttggt | 1080 |
| ggacctatta ttactacaca agtaactatt cccaaagatt tggctggatc tattattggc | 1140 |
| aaaggtggtc agcggattaa acaaatccgt catgagtcgg gagcttcgat caaaattgat | 1200 |
| gagcctttag aaggatccga agatcggatc attaccatta caggaacaca ggaccagata | 1260 |
| cagaatgcac agtatttgct gcagaacagt gtgaagcagt atgcagatgt tgaaggattc | 1320 |
| taa | 1323 |

<210> SEQ ID NO 91
<211> LENGTH: 90
<212> TYPE: DNA
<213> ORGANISM: Mus musculus

<400> SEQUENCE: 91
ggtgggaaag gaactgctcg taggaagaag aaggtggttc acagaacggc cacagcagac    60
gataagaaac tgcagttctc cttaaagaag    90

<210> SEQ ID NO 92
<211> LENGTH: 90
<212> TYPE: DNA
<213> ORGANISM: Mus musculus

<400> SEQUENCE: 92
agagagaaga atgaaagtaa caagagcagc tttgacaaaa tgattgacgc tatcaaagaa    60
agcaagagcg gcaagaagat cggagtgttc    90

<210> SEQ ID NO 93
<211> LENGTH: 90
<212> TYPE: DNA
<213> ORGANISM: Mus musculus

<400> SEQUENCE: 93
agcgctcctg aaggccaggc ccaacaacgc cggccctatc gcaggcgaag gttcccacct    60
tactacatgc ggagacccta tgcgcgtcga    90

<210> SEQ ID NO 94
<211> LENGTH: 90
<212> TYPE: DNA
<213> ORGANISM: Mus musculus

<400> SEQUENCE: 94
ggagagcaag gtagaccagt gagacagaat atgtatcggg gttacagacc acgattccga    60
aggggccctc ctcgccaaag acagcctaga    90

<210> SEQ ID NO 95
<211> LENGTH: 90
<212> TYPE: DNA
<213> ORGANISM: Mus musculus

<400> SEQUENCE: 95
cagccacctc aacgtcggta tcgccgaaac ttcaattacc gacgcagacg cccagagaac    60
cctaaaccac aagatggcaa agagacaaaa    90

<210> SEQ ID NO 96
<211> LENGTH: 90
<212> TYPE: DNA
<213> ORGANISM: Mus musculus

<400> SEQUENCE: 96
aatggaaaag acttaaaacc atcaacaccg agatcaaagg gtcaagagtc cttcaaaaaa    60
caggaaaaga ctcctaaaac accaaaagga    90

<210> SEQ ID NO 97
<211> LENGTH: 90
<212> TYPE: DNA
<213> ORGANISM: Mus musculus

<400> SEQUENCE: 97
aagggtcaag agtccttcaa aaacaggaa aagactccta aaacaccaaa aggacctagt    60
tctgtagaag acattaaggc aaaaatgcaa    90

```
<210> SEQ ID NO 98
<211> LENGTH: 90
<212> TYPE: DNA
<213> ORGANISM: Mus musculus

<400> SEQUENCE: 98
gtgtctgtgc tgagcttgtg tgagaaaggt gatgccatga ttatggaaga gacagggaag      60
atcttcaaga aggaaaagga gatgaagaaa                                       90

<210> SEQ ID NO 99
<211> LENGTH: 90
<212> TYPE: DNA
<213> ORGANISM: Mus musculus

<400> SEQUENCE: 99
gccaaggact tcttcaaaag gaagatagac ttcctcacca aacagatgga gaaaatccag      60
ccagcgctgc aggagaagca tgccatgaag                                       90

<210> SEQ ID NO 100
<211> LENGTH: 90
<212> TYPE: DNA
<213> ORGANISM: Mus musculus

<400> SEQUENCE: 100
atcaagatca tgaagagtga agtattgcga gtcacccatg aactccaagc catgaaagac      60
aaaatcaaag agaacagtga gaaaatcaaa                                       90

<210> SEQ ID NO 101
<211> LENGTH: 90
<212> TYPE: DNA
<213> ORGANISM: Mus musculus

<400> SEQUENCE: 101
atgtttgatg accgccgagg acgacctgtg ggattcccca tgaggggaag aggtggtttt      60
gacagaatgc ctcctggtcg gggtgggcgt                                       90

<210> SEQ ID NO 102
<211> LENGTH: 90
<212> TYPE: DNA
<213> ORGANISM: Homo sapiens

<400> SEQUENCE: 102
ggtgggaaag gaactgctcg cagaaagaag aaggtggttc atagaacagc cacagcagat      60
gacaaaaaac ttcagttctc cttaaagaag                                       90

<210> SEQ ID NO 103
<211> LENGTH: 90
<212> TYPE: DNA
<213> ORGANISM: Homo sapiens

<400> SEQUENCE: 103
cgagaaaaga atgaaagtaa taagagtagc tttgacaaaa tgattgaagc cattaaagaa      60
agcaagaatg gcaagaagat tggagtgttc                                       90

<210> SEQ ID NO 104
<211> LENGTH: 90
<212> TYPE: DNA
<213> ORGANISM: Homo sapiens
```

<400> SEQUENCE: 104
agtgctcccg aaggccaggc ccaacaacgc cggccctacc gcaggcgaag gttcccacct    60
tactacatgc ggagacccta tgggcgtcga    90

<210> SEQ ID NO 105
<211> LENGTH: 90
<212> TYPE: DNA
<213> ORGANISM: Homo sapiens

<400> SEQUENCE: 105
ggagaacaag gtagaccagt gaggcagaat atgtatcggg gatatagacc acgattccgc    60
aggggccctc ctcgccaaag acagcctaga    90

<210> SEQ ID NO 106
<211> LENGTH: 90
<212> TYPE: DNA
<213> ORGANISM: Homo sapiens

<400> SEQUENCE: 106
cagccacctc aacgtcggta ccgccgcaac ttcaattacc gacgcagacg cccagaaaac    60
cctaaaccac aagatggcaa agagacaaaa    90

<210> SEQ ID NO 107
<211> LENGTH: 93
<212> TYPE: DNA
<213> ORGANISM: Homo sapiens

<400> SEQUENCE: 107
aatggaaaag actcaaaacc atcatcaaca ccaagatcaa aaggacaaga atccttcaag    60
aaacaggaaa aaactcctaa aacaccaaaa gga    93

<210> SEQ ID NO 108
<211> LENGTH: 90
<212> TYPE: DNA
<213> ORGANISM: Homo sapiens

<400> SEQUENCE: 108
aaaggacaag aatccttcaa gaaacaggaa aaaactccta aacaccaaa aggacctagt    60 tctgtagaag acattaaagc aaaaatgcaa    90

<210> SEQ ID NO 109
<211> LENGTH: 90
<212> TYPE: DNA
<213> ORGANISM: Homo sapiens

<400> SEQUENCE: 109
gtgtcggtac tgagcctgtg tgagaaaggt gatgccatga ttatggaaga aacagggaaa    60
atcttcaaga aagaaaagga aatgaagaaa    90

<210> SEQ ID NO 110
<211> LENGTH: 90
<212> TYPE: DNA
<213> ORGANISM: Homo sapiens

<400> SEQUENCE: 110
gccaaggact tcttcaagag gaagatagat tttctaacca agcagatgga gaaaatccaa    60
ccagctcttc aggagaagca cgccatgaaa    90

<210> SEQ ID NO 111
<211> LENGTH: 90
<212> TYPE: DNA
<213> ORGANISM: Homo sapiens

<400> SEQUENCE: 111
atcaagatca tgaagagtga agtgttgaga gtcacccatg agctccaagc catgaaggac    60
aagataaaag agaacagtga gaaaatcaaa                                    90

<210> SEQ ID NO 112
<211> LENGTH: 90
<212> TYPE: DNA
<213> ORGANISM: Homo sapiens

<400> SEQUENCE: 112
atgtttgatg accgtcgcgg acgcccagtg ggatttccca tgcggggaag aggtggtttt    60
gacagaatgc ctcctggtcg gggtgggcgt                                    90

<210> SEQ ID NO 113
<211> LENGTH: 4
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (2)..(2)
<223> OTHER INFORMATION: Xaa is Lys or Arg
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Lys or Arg

<400> SEQUENCE: 113

Lys Xaa Xaa Xaa
1

<210> SEQ ID NO 114
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 114

Pro Lys Lys Lys Arg Arg Val
1               5

<210> SEQ ID NO 115
<211> LENGTH: 19
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (1)..(2)
<223> OTHER INFORMATION: Xaa is Lys or Arg
<220> FEATURE:
<221> NAME/KEY: MISC_FEATURE
<222> LOCATION: (3)..(12)
<223> OTHER INFORMATION: Xaa can be any amino acid
<220> FEATURE:
<221> NAME/KEY: MISC_FEATURE

```
<222> LOCATION: (13)..(14)
<223> OTHER INFORMATION: Xaa can be any amino acid or absent
<220> FEATURE:
<221> NAME/KEY: MISC_FEATURE
<222> LOCATION: (15)..(19)
<223> OTHER INFORMATION: Xaa is Lys or Arg or other amino acid

<400> SEQUENCE: 115

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 116
<211> LENGTH: 17
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (3)..(12)
<223> OTHER INFORMATION: Xaa can be any amino acid
<220> FEATURE:
<221> NAME/KEY: MISC_FEATURE
<222> LOCATION: (13)..(14)
<223> OTHER INFORMATION: Xaa can be any amino acid or absent
<220> FEATURE:
<221> NAME/KEY: MISC_FEATURE
<222> LOCATION: (16)..(17)
<223> OTHER INFORMATION: Xaa is Lys or Arg

<400> SEQUENCE: 116

Lys Arg Xaa Xaa Xaa Xaa Xaa Xaa Xaa Xaa Xaa Xaa Xaa Xaa Lys Xaa
1               5                   10                  15

Xaa

<210> SEQ ID NO 117
<211> LENGTH: 18
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (3)..(12)
<223> OTHER INFORMATION: Xaa can be any amino acid
<220> FEATURE:
<221> NAME/KEY: MISC_FEATURE
<222> LOCATION: (13)..(14)
<223> OTHER INFORMATION: Xaa can be any amino acid or absent
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MISC_FEATURE
<222> LOCATION: (17)..(17)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa is Lys or Arg

<400> SEQUENCE: 117

Lys Arg Xaa Xaa Xaa Xaa Xaa Xaa Xaa Xaa Xaa Xaa Xaa Xaa Lys Xaa
1               5                   10                  15

Xaa Xaa

<210> SEQ ID NO 118
<211> LENGTH: 16
```

```
<212> TYPE: PRT
<213> ORGANISM: Artificial sequence
<220> FEATURE:
<223> OTHER INFORMATION: An artificially synthesized peptide sequence

<400> SEQUENCE: 118

Lys Arg Pro Ala Ala Thr Lys Lys Ala Gly Gln Ala Lys Lys Lys Lys
1               5                   10                  15

<210> SEQ ID NO 119
<211> LENGTH: 8
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa is Arg, Lys, or His
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(6)
<223> OTHER INFORMATION: Xaa can be any amino acid or absent

<400> SEQUENCE: 119

Xaa Xaa Xaa Xaa Xaa Xaa Pro Tyr
1               5

<210> SEQ ID NO 120
<211> LENGTH: 19
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Xaa can be any amino acid having a hydrophobic
      side chain
<220> FEATURE:
<221> NAME/KEY: MISC_FEATURE
<222> LOCATION: (2)..(2)
<223> OTHER INFORMATION: Xaa is Gly, Ala, or Ser
<220> FEATURE:
<221> NAME/KEY: MISC_FEATURE
<222> LOCATION: (3)..(4)
<223> OTHER INFORMATION: Xaa can be any amino acid having a hydrophobic
      side chain
<220> FEATURE:
<221> NAME/KEY: MISC_FEATURE
<222> LOCATION: (5)..(15)
<223> OTHER INFORMATION: Xaa can be any amino acid
<220> FEATURE:
<221> NAME/KEY: MISC_FEATURE
<222> LOCATION: (16)..(17)
<223> OTHER INFORMATION: Xaa can be any amino acid or absent

<400> SEQUENCE: 120

Xaa Xaa Xaa Xaa Xaa Xaa Xaa Xaa Xaa Xaa Xaa Xaa Xaa Xaa Xaa
1               5                   10                  15

Xaa Pro Tyr

<210> SEQ ID NO 121
<211> LENGTH: 27
<212> TYPE: PRT
<213> ORGANISM: Artificial sequence
<220> FEATURE:
<223> OTHER INFORMATION: An artificially synthesized peptide sequence
```

<400> SEQUENCE: 121

Phe Gly Asn Tyr Asn Asn Gln Ser Ser Asn Phe Gly Pro Met Lys Gly
1               5                   10                  15

Gly Asn Phe Gly Gly Arg Ser Ser Gly Pro Tyr
            20                  25

<210> SEQ ID NO 122
<211> LENGTH: 20
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: MISC_FEATURE
<222> LOCATION: (1)..(5)
<223> OTHER INFORMATION: Xaa can be any amino acid
<220> FEATURE:
<221> NAME/KEY: MISC_FEATURE
<222> LOCATION: (6)..(8)
<223> OTHER INFORMATION: Xaa can be any amino acid or absent
<220> FEATURE:
<221> NAME/KEY: MISC_FEATURE
<222> LOCATION: (9)..(16)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid or absent

<400> SEQUENCE: 122

Xaa Xaa Xaa Xaa Xaa Xaa Xaa Xaa Xaa Xaa Xaa Xaa Xaa Xaa Xaa Xaa
1               5                   10                  15

Xaa Xaa Pro Tyr
            20

<210> SEQ ID NO 123
<211> LENGTH: 27
<212> TYPE: PRT
<213> ORGANISM: Artificial sequence
<220> FEATURE:
<223> OTHER INFORMATION: An artificially synthesized peptide sequence

<400> SEQUENCE: 123

Gly Glu Gly Glu Arg Pro Ala Gln Asn Glu Lys Arg Lys Glu Lys Asn
1               5                   10                  15

Ile Lys Arg Gly Gly Asn Arg Phe Glu Pro Tyr
            20                  25

<210> SEQ ID NO 124
<211> LENGTH: 43
<212> TYPE: PRT
<213> ORGANISM: Artificial sequence
<220> FEATURE:
<223> OTHER INFORMATION: An artificially synthesized peptide sequence

<400> SEQUENCE: 124

Val His Ser His Lys Lys Lys Lys Ile Arg Thr Ser Pro Thr Phe Arg
1               5                   10                  15

Arg Pro Lys Thr Leu Arg Leu Arg Arg Gln Pro Lys Tyr Pro Arg Lys
            20                  25                  30

Ser Ala Pro Arg Arg Asn Lys Leu Asp His Tyr
            35                  40

<210> SEQ ID NO 125
<211> LENGTH: 37

```
<212> TYPE: PRT
<213> ORGANISM: Artificial sequence
<220> FEATURE:
<223> OTHER INFORMATION: An artificially synthesized peptide sequence

<400> SEQUENCE: 125

Met Ser His Arg Lys Phe Ser Ala Pro Arg His Gly Ser Leu Gly Phe
1               5                   10                  15

Leu Pro Arg Lys Arg Ser Ser Arg His Arg Gly Lys Val Lys Ser Phe
            20                  25                  30

Pro Lys Asp Asp Pro
        35

<210> SEQ ID NO 126
<211> LENGTH: 50
<212> TYPE: PRT
<213> ORGANISM: Artificial sequence
<220> FEATURE:
<223> OTHER INFORMATION: An artificially synthesized peptide sequence

<400> SEQUENCE: 126

Glu Val Thr Asn Asp Phe Val Met Leu Lys Gly Cys Val Val Gly Thr
1               5                   10                  15

Lys Lys Arg Val Leu Thr Leu Arg Lys Ser Leu Leu Val Gln Thr Lys
            20                  25                  30

Arg Arg Ala Leu Glu Lys Ile Asp Leu Lys Phe Ile Asp Thr Thr Ser
        35                  40                  45

Lys Phe
    50

<210> SEQ ID NO 127
<211> LENGTH: 50
<212> TYPE: PRT
<213> ORGANISM: Artificial sequence
<220> FEATURE:
<223> OTHER INFORMATION: An artificially synthesized peptide sequence

<400> SEQUENCE: 127

Ser Leu Gly Gln Ser Ala Ser Glu Thr Glu Glu Asp Thr Val Ser Val
1               5                   10                  15

Ser Lys Lys Glu Lys Asn Arg Lys Arg Asn Arg Lys Lys Lys
            20                  25                  30

Lys Pro Gln Arg Val Arg Gly Val Ser Ser Glu Ser Ser Gly Asp Arg
        35                  40                  45

Glu Lys
    50

<210> SEQ ID NO 128
<211> LENGTH: 50
<212> TYPE: PRT
<213> ORGANISM: Artificial sequence
<220> FEATURE:
<223> OTHER INFORMATION: An artificially synthesized peptide sequence

<400> SEQUENCE: 128

Pro Thr Arg Tyr Ser Val Asp Ile Pro Leu Asp Lys Thr Val Val Asn
1               5                   10                  15

Lys Asp Val Phe Arg Asp Pro Ala Leu Lys Arg Lys Ala Arg Arg Glu
            20                  25                  30
```

```
Ala Lys Val Lys Phe Glu Glu Arg Tyr Lys Thr Gly Lys Asn Lys Trp
        35                  40                  45

Phe Phe
    50

<210> SEQ ID NO 129
<211> LENGTH: 50
<212> TYPE: PRT
<213> ORGANISM: Artificial sequence
<220> FEATURE:
<223> OTHER INFORMATION: An artificially synthesized peptide sequence

<400> SEQUENCE: 129

Lys Met Phe Lys Gly Lys Arg Gly Ala Gln Leu Ala Lys Asp Ile Ala
1               5                   10                  15

Arg Arg Ser Lys Thr Phe Asn Pro Gly Ala Gly Leu Pro Thr Asp Lys
            20                  25                  30

Lys Lys Gly Gly Pro Ser Pro Gly Asp Val Glu Ala Ile Lys Asn Ala
        35                  40                  45

Ile Ala
    50

<210> SEQ ID NO 130
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 130

Lys Lys Glu Lys
1
```